United States Patent
Jablonski et al.

(10) Patent No.: US 8,012,998 B2
(45) Date of Patent: Sep. 6, 2011

(54) PYRROLIDINE ARYL-ETHER AS NK-3 RECEPTOR ANTAGONISTS

(75) Inventors: Philippe Jablonski, Steinbrunn-le-Haut (FR); Kenichi Kawasaki, Fujisawa (JP); Henner Knust, Rheinfelden (DE); Anja Limberg, Basel (CH); Matthias Nettekoven, Grenzach-Wyhlen (DE); Hasane Ratni, Habsheim (FR); Claus Riemer, Freiburg (DE); Xihan Wu, Shanghai (CN)

(73) Assignee: Hoffmann—LA Roche Inc., Nutley, NJ (US)

( * ) Notice: Subject to any disclaimer, the term of this patent is extended or adjusted under 35 U.S.C. 154(b) by 534 days.

(21) Appl. No.: 12/185,157

(22) Filed: Aug. 4, 2008

(65) Prior Publication Data
US 2009/0042896 A1  Feb. 12, 2009

(30) Foreign Application Priority Data
Aug. 7, 2007 (EP) .................... 07113942

(51) Int. Cl.
A61K 31/4439 (2006.01)
C07D 401/14 (2006.01)
(52) U.S. Cl. ........... 514/333; 546/256
(58) Field of Classification Search ........... 546/256; 514/333
See application file for complete search history.

(56) References Cited

U.S. PATENT DOCUMENTS

| 4,143,061 A | 3/1979 | Kubo et al. |
| 5,576,333 A | 11/1996 | Miller et al. |
| 5,972,938 A | 10/1999 | Rupniak et al. |

FOREIGN PATENT DOCUMENTS

| DE | 2659404 | 7/1977 |
| EP | 1192952 | 4/2002 |
| GB | 2000136 | 1/1979 |
| WO | WO 95/16679 | 6/1995 |
| WO | WO 95/18124 | 7/1995 |
| WO | WO 95/23798 | 9/1995 |
| WO | WO 99/01451 | 1/1999 |
| WO | WO 02/079134 | 10/2002 |
| WO | WO 2005/002577 | 1/2005 |
| WO | WO 2007/011162 | 1/2007 |

OTHER PUBLICATIONS

Kamali et al., Current Opinion in Investigational Drugs (2001) 2(7) pp. 950-956.
Giardina et al., Exp. Opinion Ther. Patents (2000) 10(6) pp. 939-960.
Barker, R., Neurosci. Res. (1996) vol. 7, pp. 187-214.
Longmore et al., Can. J. Phys. (1997) vol. 75 pp. 612-621.
Kramer et al., Science (1998) vol. 281 pp. 1640-1645.
Maggi, et al., Auton. Pharmacol. vol. 13, pp. 23-93 (1993).
Navari et al., The New England Journal of Medicine vol. 340 No. 3, pp. 190-195 (1999).
Fujima et al., Tetrahedron Asymmetry (2003) vol. 14(10) pp. 1385-1391.
Alajarin et al., J. Med. Chem. (1995) vol. 38(15) pp. 2830-2841.
Takahata et al., J. Org. Chem. (1989) vol. 54(20) pp. 4812-4822.
Tooney et al., Neurosci. Letters, vol. 283 pp. 185-188 (2000).
Giardina et al., Exp. Opin. Ther. Patents vol. 10 pp. 939-960 (2000).
Jung et al., Neuroscience vol. 74 pp. 403-414 (1996).
Marco et al., Neuropeptides vol. 32, pp. 481-488 (1998).
Kamali, F., Current Opinion in Investigational Drugs vol. 2(7) pp. 950-956 (2001).
Dega-Szafran et al., J. Molecular Structure, vol. 560 p. 261 (2001).

*Primary Examiner* — Patricia Morris
(74) *Attorney, Agent, or Firm* — George W. Johnston; Patricia S. Rocha-Tramaloni; Kimberly J. Prior

(57) ABSTRACT

The invention relates to a compound of formula I

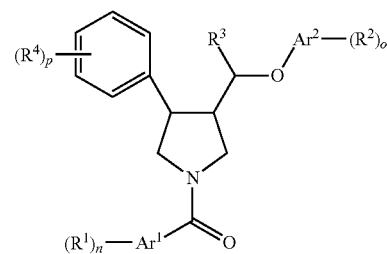

wherein
$Ar^1$,
$Ar^2$,
$R^1$,
$R^2$, $R^3$, $R^4$, n, o, p, and q are as defined herein and to a pharmaceutically active salt thereof, including all stereoisomeric forms, individual diastereoisomers and enantiomers of the compound of formula (I) as well as racemic and non-racemic mixtures thereof. The compounds are high potential NK-3 receptor antagonists for the treatment of depression, pain, psychosis, Parkinson's disease, schizophrenia, anxiety and attention deficit hyperactivity disorder (ADHD).

8 Claims, No Drawings

PYRROLIDINE ARYL-ETHER AS NK-3 RECEPTOR ANTAGONISTS

PRIORITY TO RELATED APPLICATION(S)

This application claims the benefit of European Patent Application No. 07113942.2 filed Aug. 7, 2007, which is hereby incorporated by reference in its entirety.

BACKGROUND OF THE INVENTION

The three main mammalian tachykinins, substance P (SP), neurokinin A (NKA) and neurokinin B (NKB) belong to the family of neuropeptides sharing the common COOH-terminal pentapeptide sequence of Phe-X-Gly-Leu-Met-NH$_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters,* 2000, 283, 185-188; *Exp. Opin. Ther. Patents* 2000, 10, 939-960; *Neuroscience,* 1996, 74, 403-414; *Neuropeptides,* 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs,* 2001, 2(7), 950-956 and *Psychiatric Disorders Study* 4, *Schizophrenia,* June 2003, Decision Recources, Inc., Waltham, Mass.). The proposed drug SR 142,801 has been shown in a phase II trial as active on positive symptoms of schizophrenia, such as altered behaviour, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs,* 2001, 2(7), 950-956 956 and *Psychiatric Disorders Study* 4, *Schizophrenia,* June 2003, Decision Recources, Inc., Waltham, Mass.).

SUMMARY OF THE INVENTION

The invention provides a compound of formula I

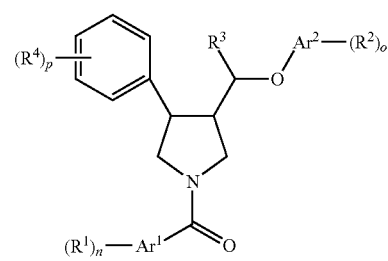

wherein
Ar$^1$ is aryl or a five or six membered heteroaryl;
Ar$^2$ is aryl or a five or six membered heteroaryl;
R$^1$ is hydrogen, halogen, lower alkyl, lower alkoxy, lower alkyl substituted by halogen, lower alkoxy substituted by halogen, S-lower alkyl, —S(O)$_2$-lower alkyl, —S(O)$_2$-di-lower alkyl amino, —(CH$_2$)$_q$R, cyano, amino, mono or di-lower alkyl amino, NHC(O)-lower alkyl, cycloalkyl or a five membered heteroaryl, optionally substituted by lower alkyl; wherein R is cyano, di-lower alkyl amino or pyrrolidin-1-yl;
R$^2$ is hydrogen, halogen, lower alkyl, lower alkyl substituted by halogen or cyano;
R$^3$ is hydrogen or lower alkyl or CH$_2$OH;
R$^4$ is hydrogen, halogen, lower alkyl, lower alkyl substituted by halogen or cyano;
n is 1, 2 or 3; in case n is 2 or 3, each R$^1$ is the same or different;
o is 1, 2 or 3; in case o is 2 or 3, each R$^2$ is the same or different;
p is 1, 2 or 3; in case p is 2 or 3, each R$^4$ is the same or different;
q is 1 or 2;
and a pharmaceutically active salt thereof.

The invention includes all stereoisomeric forms, including individual diastereoisomers and enantiomers of the compound of formula (I) as well as racemic and non-racemic mixtures thereof.

The present invention also provides pharmaceutical compositions comprising a therapeutically effective amount of a compound of the invention and a pharmaceutically acceptable carrier. The invention further provides processes for the manufacture of the compounds and compositions of the invention.

Compounds are high potential NK-3 receptor antagonists for the treatment of depression, pain, psychosis, Parkinson's disease, schizophrenia, anxiety and attention deficit hyperactivity disorder (ADHD).

The preferred indications using the compounds of the present invention are depression, psychosis, Parkinson's disease, schizophrenia, anxiety and attention deficit hyperactivity disorder (ADHD).

THE DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-8 carbon atoms, for example, methyl, ethyl, propyl, isopropyl, n-butyl, i-butyl, t-butyl and the like. Preferred lower alkyl groups are groups with 1-4 carbon atoms.

The term "halogen" denotes chlorine, iodine, fluorine and bromine.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "lower alkoxy" denotes a group containing a lower alkyl residue as defined above that is attached via an oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes a lower alkoxy group as defined above wherein at least one hydrogen atom is replaced by halogen. Preferred lower alkoxy substituted by halogen groups are groups having 1-4 carbon atoms.

The term "cycloalkyl" denotes a saturated carbon ring containing from 3-7 carbon atoms, for example, cyclopropyl, cyclobutyl, cyclpentyl, cyclohexyl, cycloheptyl, and the like.

The term "aryl" denotes a cyclic aromatic hydrocarbon radical consisting of one or more fused rings containing 6-14 ring carbon atoms in which at least one ring is aromatic in nature, for example phenyl, naphthyl or indanyl. The term aryl includes groups that are attached through a linker, such as —O— or —$CH_2$—, for example benzyl. Preferred is the phenyl group.

The term "five or six membered heteroaryl" denotes a cyclic aromatic radical consisting of one or more fused rings containing 6-14 carbon atoms, which contains at least one heteroatom selected from N, O and S. Where the heteroaryl group contains two or more fused rings, at least one ring contains a heteroatom and is aromatic in nature. The other rings may be carbocyclic, aromatic, heteroaromatic, or heterocyclic. Examples of five or six membered heteroaryl include quinoxalinyl, pyrazinyl, pyridazinyl, pyrazolyl, pyridine-2, 3 or [4]-yl, pyrimidinyl, oxazolyl, [1.2.4]oxadiazolyl, [1.3.4]oxadiazolyl, triazolyl, tetrazolyl, thiazolyl, thiadiazolyl, thiophenyl, isoxazolyl, pyrrolyl, furanyl or imidazolyl. Preferred heteroaryl groups are pyrimidinyl, pyridazinil, thiophenyl, furanyl, isoxazolyl, pyrrolyl, thiazolyl and pyridinyl "Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The following groups of compounds of formula I are preferred:

A compound of formula I, wherein $Ar^1$ is phenyl, for example the following compounds 4-[(3SR,4RS)-3-[(RS)-1-(5-chloro-pyridin-2-yloxy)-ethyl]-4-(3,4-dichloro-phenyl)-pyrrolidine-1-carbonyl]-benzonitrile, 6-{(SR)-1-[(3RS,4SR)-4-(3,4-dichloro-phenyl)-1-(4-oxadiazol-5-yl-benzoyl)-pyrrolidin-3-yl]-ethoxy}-nicotinonitrile, 6-((SR)-1-{(3RS,4SR)-4-(3,4-dichloro-phenyl)-1-[4-(3-methyl-[1,2,4]oxadiazol-5-yl)-benzoyl]-pyrrolidin-3-yl}-ethoxy)-nicotinonitrile, 6-((SR)-1-{(3RS,4SR)-4-(3,4-dichloro-phenyl)-1-[4-(5-methyl-[1,2,4]oxadiazol-3-yl)-benzoyl]-pyrrolidin-3-yl}-ethoxy)-nicotinonitrile, 6-{(SR)-1-[(3RS,4SR)-4-(3,4-dichloro-phenyl)-1-(4-[1,3,4]oxadiazol-2-yl-benzoyl)-pyrrolidin-3-yl]-ethoxy}-nicotinonitrile, 6-{(SR)-1-[(3RS,4SR)-1-(4-cyano-2-fluoro-benzoyl)-4-(3,4-dichloro-phenyl)-pyrrolidin-3-yl]-ethoxy}-nicotinonitrile, or {(3SR,4RS)-3-(3,4-dichloro-phenyl)-4-[(SR)-1-(5-trifluoromethyl-pyridin-2-yloxy)-ethyl]-pyrrolidin-1-yl}-[4-(3-methyl-[1,2,4]oxadiazol-5-yl)-phenyl]-methanone.

A compound of formula I, wherein $Ar^1$ is pyridine-4-yl, for example the following compounds

[(3SR,4RS)-3-[(RS)-1-(5-chloro-pyridin-2-yloxy)-ethyl]-4-(3,4-dichloro-phenyl)-pyrrolidin-1-yl]-(2-methyl-pyridin-4-yl)-methanone or (2-chloro-pyridin-4-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone.

A compound of formula I, wherein $Ar^1$ is pyridine-3-yl, for example the following compounds

[(3SR,4RS)-3-[(RS)-1-(5-chloro-pyridin-2-yloxy)-ethyl]-4-(3,4-dichloro-phenyl)-pyrrolidin-1-yl]-(6-methyl-pyridin-3-yl)-methanone,

[(3SR,4RS)-3-[(RS)-1-(5-chloro-pyridin-2-yloxy)-ethyl]-4-(3,4-dichloro-phenyl)-pyrrolidin-1-yl]-(6-dimethylamino-pyridin-3-yl)-methanone,

[(3S,4R)-3-[(R)-1-(5-chloro-pyridin-2-yloxy)-ethyl]-4-(3,4-dichloro-phenyl)-pyrrolidin-1-yl]-(6-methoxy-pyridin-3-yl)-methanone,

[(3R,4S)-3-[(S)-1-(5-chloro-pyridin-2-yloxy)-ethyl]-4-(3,4-dichloro-phenyl)-pyrrolidin-1-yl]-(6-methoxy-pyridin-3-yl)-methanone, 5-[(3SR,4RS)-3-[(RS)-1-(5-chloro-pyridin-2-yloxy)-ethyl]-4-(3,4-dichloro-phenyl)-pyrrolidine-1-carbonyl]-pyridine-2-carbonitrile,

[(3SR,4RS)-3-[(RS)-1-(5-chloro-pyridin-2-yloxy)-ethyl]-4-(3,4-dichloro-phenyl)-pyrrolidin-1-yl]-(6-dimethylaminomethyl-pyridin-3-yl)-methanone,
[(3SR,4RS)-3-[(RS)-1-(5-chloro-pyridin-2-yloxy)-ethyl]-4-(3,4-dichloro-phenyl)-pyrrolidin-1-yl]-(6-methylsulfanyl-pyridin-3-yl)-methanone,
6-{(SR)-1-[(3RS,4SR)-4-(3,4-dichloro-phenyl)-1-(6-cyano-pyridine-3-carbonyl)-pyrrolidin-3-yl]-ethoxy}-nicotinonitrile,
5-[(3S,4R)-3-[(R)-1-(5-chloro-pyridin-2-yloxy)-ethyl]-4-(3,4-dichloro-phenyl)-pyrrolidine-1-carbonyl]-pyridine-2-carbonitrile,
5-{(3SR,4RS)-3-(3,4-dichloro-phenyl)-4-[(SR)-1-(5-trifluoromethyl-pyridin-2-yloxy)-ethyl]-pyrrolidine-1-carbonyl}-pyridine-2-carbonitrile,
5-[(3RS,4SR)-3-[(SR)-1-(5-cyano-pyridin-2-yloxy)-ethyl]-4-(3,4-dichloro-phenyl)-pyrrolidine-1-carbonyl]-pyridine-2-sulfonic acid dimethylamide,
6-{(SR)-1-[(3RS,4SR)-4-(3,4-dichloro-phenyl)-1-(6-pyrazol-1-yl-pyridine-3-carbonyl)-pyrrolidin-3-yl]-ethoxy}-nicotinonitrile,
6-{(SR)-1-[(3RS,4SR)-4-(3,4-dichloro-phenyl)-1-(6-methanesulfonyl-pyridine-3-carbonyl)-pyrrolidin-3-yl]-ethoxy}-nicotinonitrile,
6-{(SR)-1-[(3RS,4SR)-4-(3,4-dichloro-phenyl)-1-(6-imidazol-1-yl-pyridine-3-carbonyl)-pyrrolidin-3-yl]-ethoxy}-nicotinonitrile,
6-{(SR)-1-[(3RS,4SR)-4-(3,4-dichloro-phenyl)-1-(5-methyl-pyridine-3-carbonyl)-pyrrolidin-3-yl]-ethoxy}-nicotinonitrile,
6-((SR)-1-{(3RS,4SR)-4-(3,4-dichloro-phenyl)-1-[6-(2,2,2-trifluoro-ethoxy)-pyridine-3-carbonyl]-pyrrolidin-3-yl}-ethoxy)-nicotinonitrile,
{(3SR,4RS)-3-(3,4-dichloro-phenyl)-4-[(SR)-1-(5-trifluoromethyl-pyridin-2-yloxy)-ethyl]-pyrrolidin-1-yl}-(6-pyrazol-1-yl-pyridin-3-yl)-methanone,
(6-chloro-pyridin-3-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone, or,
6-{(SR)-1-[(3RS,4SR)-4-(3,4-dichloro-phenyl)-1-(6-ethyl-5-methyl-pyridine-3-carbonyl)-pyrrolidin-3-yl]-ethoxy}-nicotinonitrile.

A compound of formula I, wherein Ar¹ is a five membered heteroaryl, for example the following compound
[(3SR,4RS)-3-[(RS)-1-(5-chloro-pyridin-2-yloxy)-ethyl]-4-(3,4-dichloro-phenyl)-pyrrolidin-1-yl]-(1-cyclopropyl-2,5-dimethyl-1 H-pyrrol-3-yl)-methanone.

A compound of formula I, wherein Ar¹ is pyrimidin, for example the following compounds
[(3R,4S)-3-[(S)-1-(5-chloro-pyridin-2-yloxy)-ethyl]-4-(3,4-dichloro-phenyl)-pyrrolidin-1-yl]-(2-methyl-pyrimidin-5-yl)-methanone,
5-[(3S,4R)-3-[(R)-1-(5-chloro-pyridin-2-yloxy)-ethyl]-4-(3,4-dichloro-phenyl)-pyrrolidine-1-carbonyl]-pyrimidine-2-carbonitrile, or
(2-cyclopropyl-pyrimidin-5-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone.

A compound of formula I, wherein Ar¹ is pyridazinyl, for example the following compounds
6-{(SR)-1-[(3RS,4SR)-4-(3,4-dichloro-phenyl)-1-(6-methyl-pyridazine-4-carbonyl)-pyrrolidin-3-yl]-ethoxy}-nicotinonitrile,
[(3R,4S)-3-[(S)-1-(5-chloro-pyridin-2-yloxy)-ethyl]-4-(3,4-difluoro-phenyl)-pyrrolidin-1-yl]-(6-methyl-pyridazin-4-yl)-methanone,
{(3S,4R)-3-(4-chloro-3-fluoro-phenyl)-4-[(S)-1-(5-chloro-pyridin-2-yloxy)-ethyl]-pyrrolidin-1-yl}-(6-methyl-pyridazin-4-yl)-methanone,
6-{(S)-1-[(3R,4S)-4-(4-chloro-phenyl)-1-(6-methyl-pyridazine-4-carbonyl)-pyrrolidin-3-yl]-ethoxy}-nicotinonitrile,
[(3R,4S)-3-[(R)-1-(5-chloro-pyridin-2-yloxy)-2-hydroxy-ethyl]-4-(3,4-dichloro-phenyl)-pyrrolidin-1-yl]-(6-methyl-pyridazin-4-yl)-methanone,
[(3R,4S)-3-[(S)-1-(5-chloro-pyridin-2-yloxy)-ethyl]-4-(4-fluoro-phenyl)-pyrrolidin-1-yl]-(6-methyl-pyridazin-4-yl)-methanone, or
{(3S,4R)-3-(4-chloro-phenyl)-4-[(S)-1-(5-trifluoromethyl-pyridin-2-yloxy)-ethyl]-pyrrolidin-1-yl}-(6-methyl-pyridazin-4-yl)-methanone.

The present invention further provides compounds of formula I

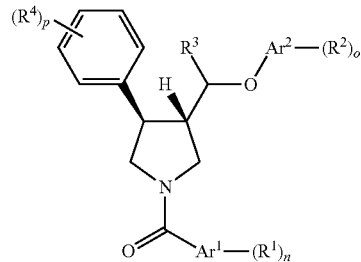

wherein
Ar¹ is aryl or a five or six membered heteroaryl;
Ar² is aryl or a five or six membered heteroaryl;
R¹ is hydrogen, halogen, lower alkyl, lower alkoxy, cyano, amino, mono or di-lower alkyl amino, cycloalkyl or is lower alkyl substituted by halogen, cyano or amino;
R² is hydrogen, halogen, lower alkyl, cyano or is lower alkyl substituted by halogen or cyano;
R³ is hydrogen or lower alkyl;
R⁴ is hydrogen, lower alkyl or halogen;
n is 1, 2 or 3; in case n is 2 or 3, each R¹ is the same or different;
o is 1, 2 or 3; in case o is 2 or 3, each R² is the same or different;
p is 1, 2 or 3; in case p is 2 or 3, each R⁴ is the same or different;
or to a pharmaceutically active salt thereof.

The preparation of compounds of formula I of the present invention can be carried out in sequential or convergent synthetic routes. Syntheses of the compounds of the invention are shown in the following schemes 1 to 7. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by processes described below, which process comprises a) reacting a compound of formula

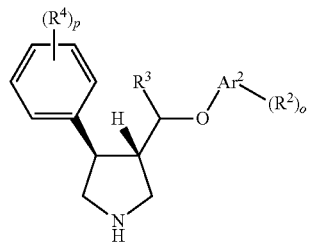

with a compound of formula

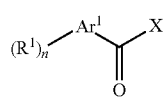

to obtain a compound of formula

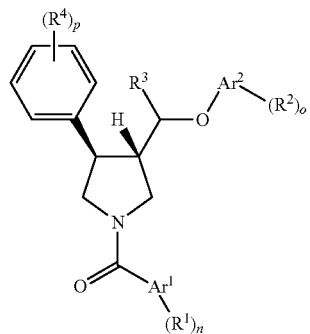

wherein the definitions have same meanings as described above and X is halogen, preferably chloro or hydroxy, or b) reacting a compound of formula

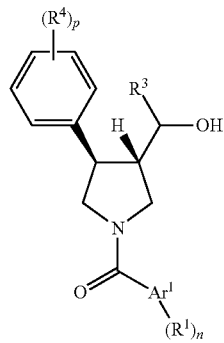

with a compound of formula

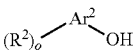

to obtain a compound of formula

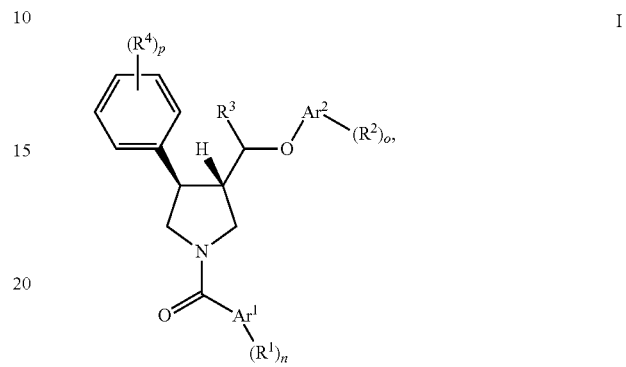

and
if desired, converting the compounds obtained into pharmaceutically acceptable acid addition salts.

The processes are described in the following schemes in more detail.

Scheme 1

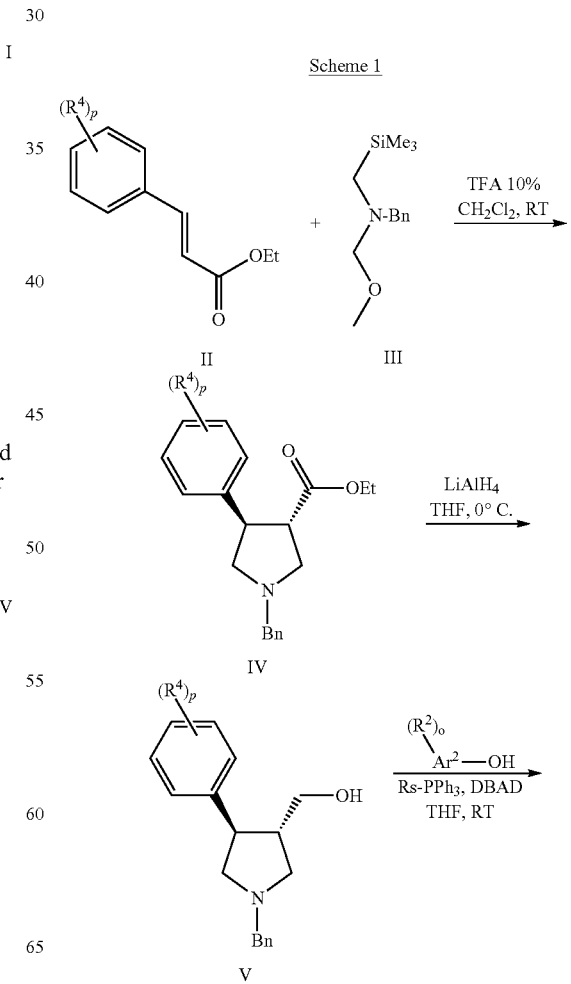

-continued

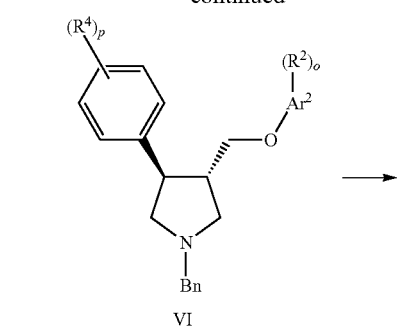

VI

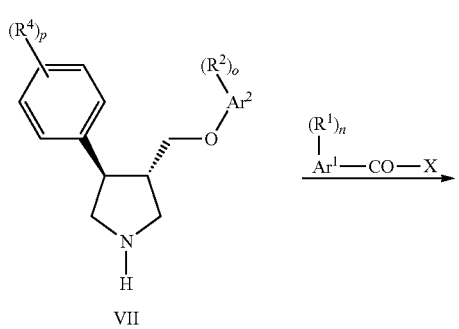

VII

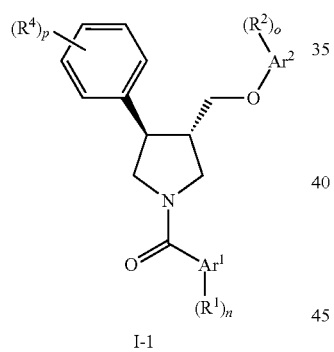

I-1

Scheme 2

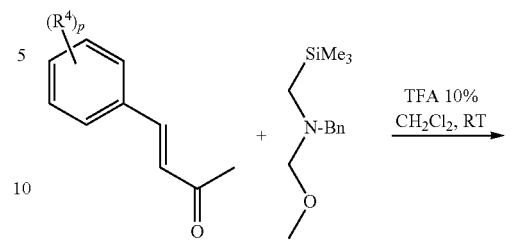

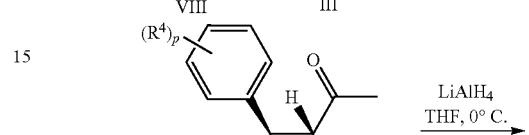

IX

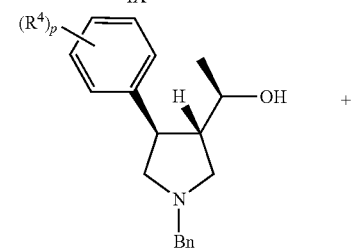

X-A +

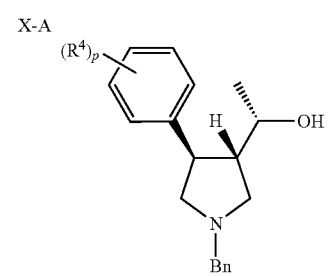

X-B

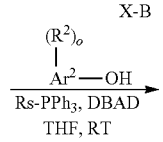

X-B

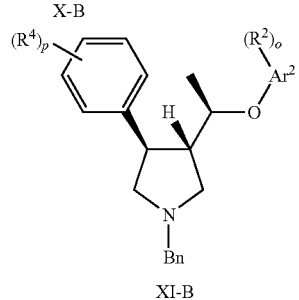

XI-B

The 3,4-disubstituted pyrrolidines IV were prepared via a stereo specific 1,3-dipolar cycloaddition between the (E)-3-substituted phenyl-acrylic acid ethyl ester derivatives II and the azomethine ylide generated in situ from the N-(methoxymethyl)-N-(phenylmethyl)-N-(trimethylsilyl)methylamine III in the presence of a catalytic amount of acid, such as TFA. Reduction of the ester moiety using standard conditions for example LiAlH₄ yielded the alcohol V. Standard Mitsunobu reaction with for example a phenol, pyridin-ol, pyrimidin-ol gave the aryl-ether VI. Selective N-debenzylation was then carried out using several known procedures which are compatible with the substitution patterns of the aromatic rings to afford VII. Final derivatives I-1 were obtained via a coupling with a suitable acid chloride or carboxylic acide using known methods.

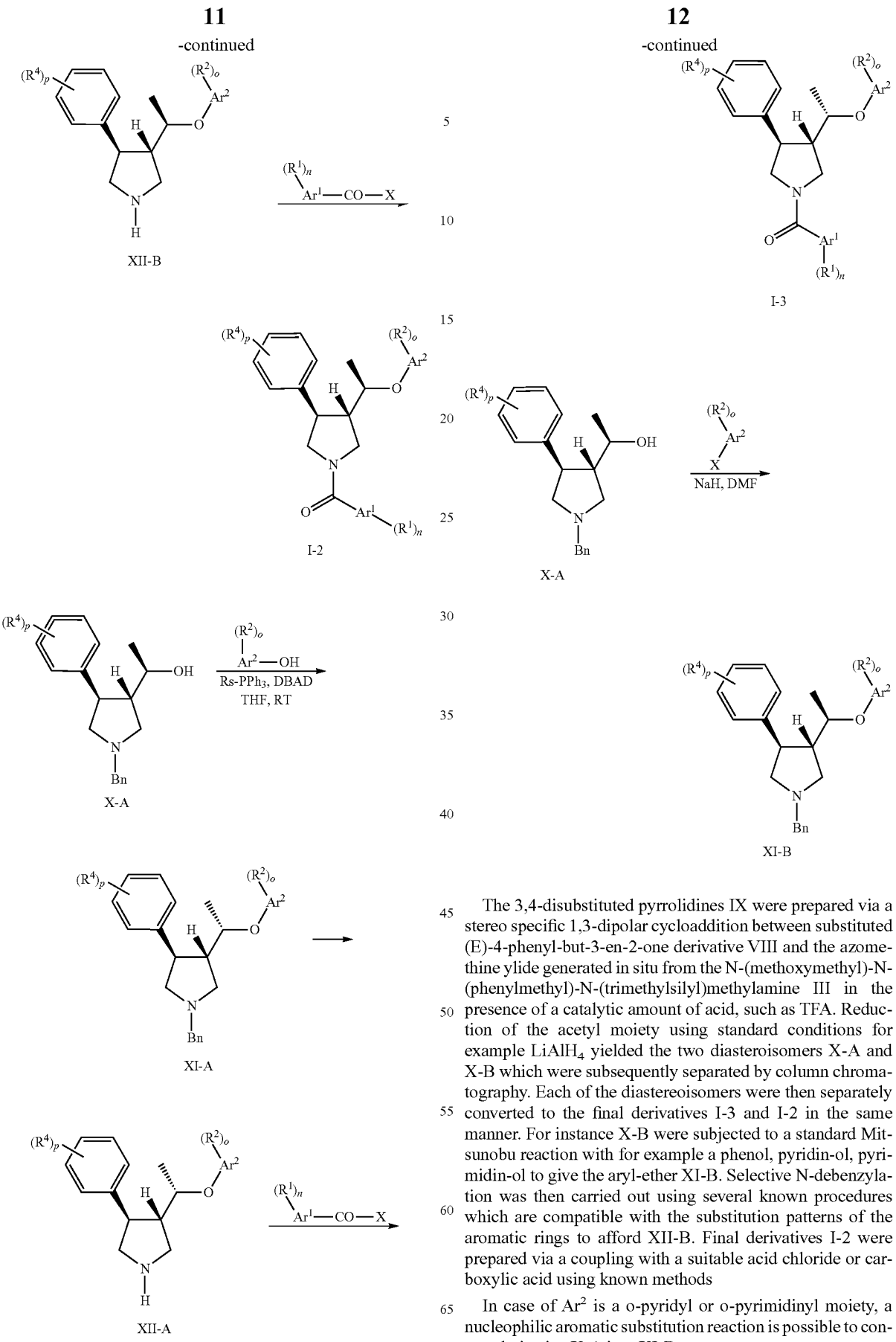

The 3,4-disubstituted pyrrolidines IX were prepared via a stereo specific 1,3-dipolar cycloaddition between substituted (E)-4-phenyl-but-3-en-2-one derivative VIII and the azomethine ylide generated in situ from the N-(methoxymethyl)-N-(phenylmethyl)-N-(trimethylsilyl)methylamine III in the presence of a catalytic amount of acid, such as TFA. Reduction of the acetyl moiety using standard conditions for example LiAlH$_4$ yielded the two diastereoisomers X-A and X-B which were subsequently separated by column chromatography. Each of the diastereoisomers were then separately converted to the final derivatives I-3 and I-2 in the same manner. For instance X-B were subjected to a standard Mitsunobu reaction with for example a phenol, pyridin-ol, pyrimidin-ol to give the aryl-ether XI-B. Selective N-debenzylation was then carried out using several known procedures which are compatible with the substitution patterns of the aromatic rings to afford XII-B. Final derivatives I-2 were prepared via a coupling with a suitable acid chloride or carboxylic acid using known methods In case of Ar$^2$ is a o-pyridyl or o-pyrimidinyl moiety, a nucleophilic aromatic substitution reaction is possible to convert derivative X-A into XI-B.

Scheme 3

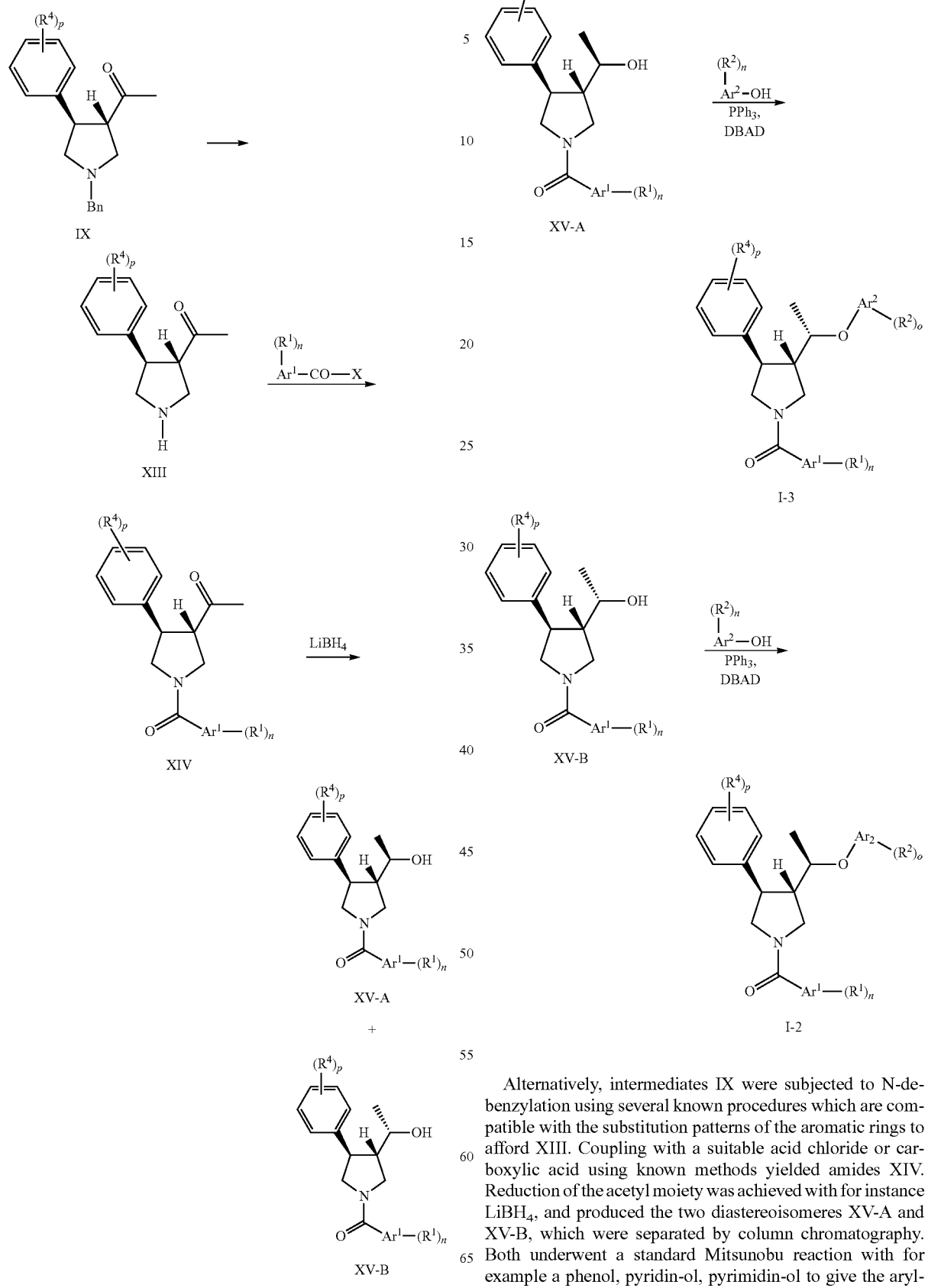

Alternatively, intermediates IX were subjected to N-debenzylation using several known procedures which are compatible with the substitution patterns of the aromatic rings to afford XIII. Coupling with a suitable acid chloride or carboxylic acid using known methods yielded amides XIV. Reduction of the acetyl moiety was achieved with for instance LiBH$_4$, and produced the two diastereoisomeres XV-A and XV-B, which were separated by column chromatography. Both underwent a standard Mitsunobu reaction with for example a phenol, pyridin-ol, pyrimidin-ol to give the aryl-ether derivatives I-3 and I-2.

Scheme 4

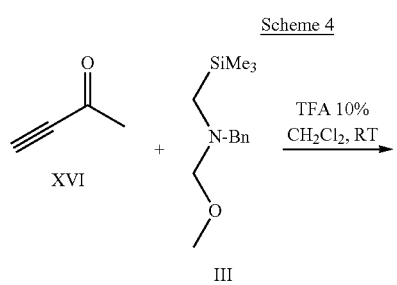

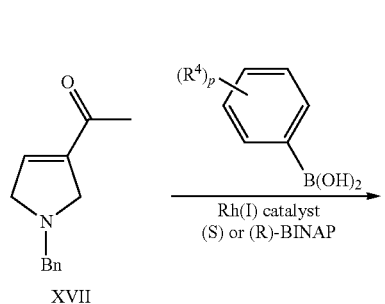

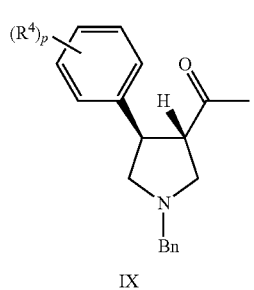

An alternative method for the preparation of intermediates IX is highlighted scheme 4. A 1,3-dipolar cycloaddition between the commercially available but-3-yn-2-one XVI and the azomethine ylide generated in situ from the N-(methoxymethyl)-N-(phenylmethyl)-N-(trimethylsilyl)methylamine III in the presence of a catalytic amount of acid, such as TFA afforded the dihydropyrrole derivative XVII. A 1,4-addition of a boronic acid catalysed by a Rh(I) catalyst such as the Rhacetylacetonatbis(ethylene) in a presence of of a chiral phosphine ligand such as the (R) or (S)-BINAP afforded the optically enriched disubstituted pyrrolidine IX. Similar Rh-catalysed asymmetric 1,4-arylation have been reported earlier (*Tet. Lett.*, 2004, 45(16), 3265)

Scheme 5

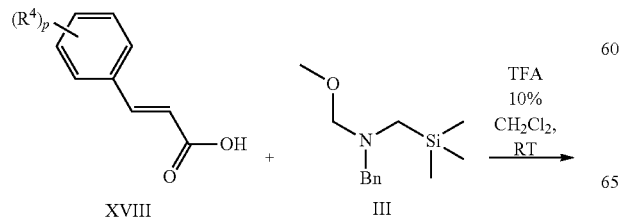

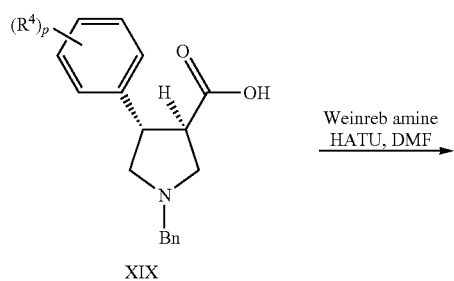

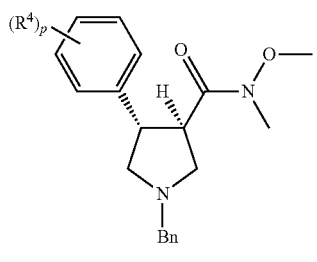

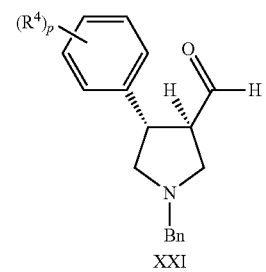

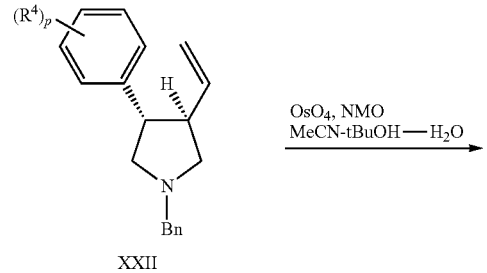

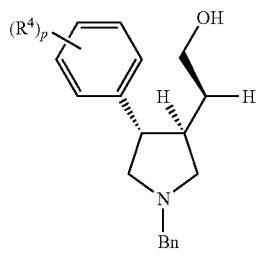

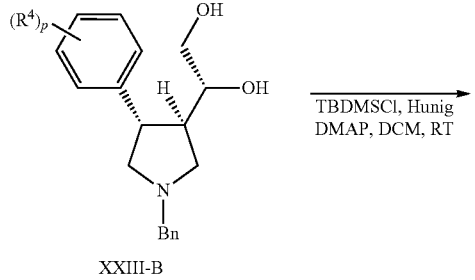

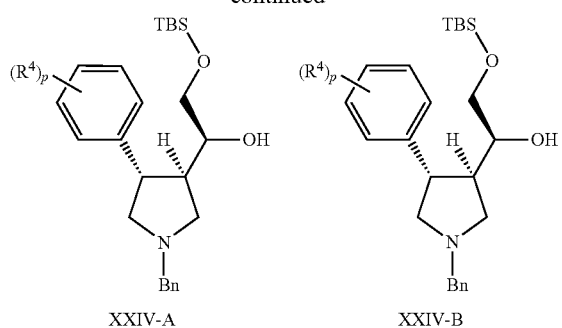

XXIV-A            XXIV-B

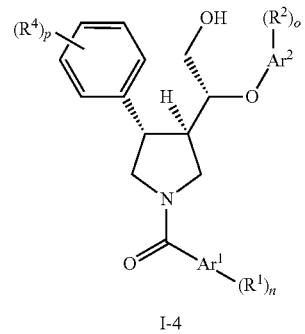

I-4

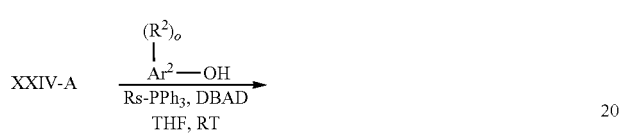

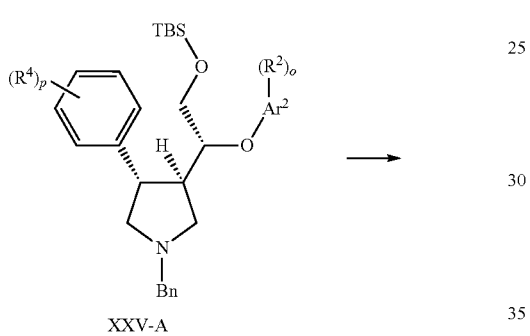

XXV-A

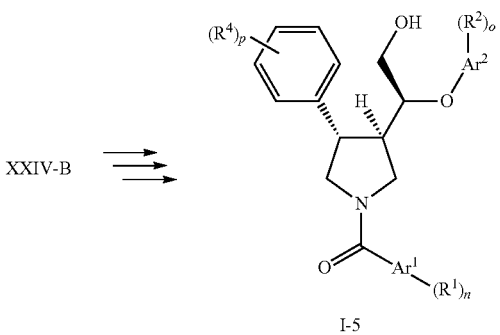

I-5

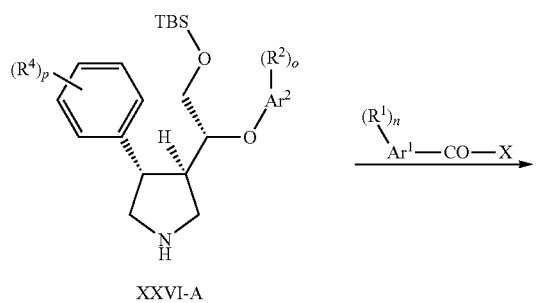

XXVI-A

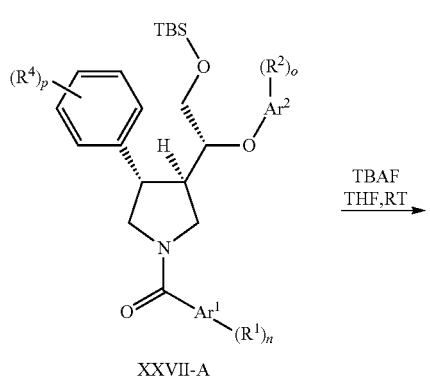

XXVII-A

The scheme 5 describe the preparation of derivatives of the type I with $R^3$ is a hydromethyl moiety. The 3,4-disubstituted pyrrolidines XIX were prepared via a stereo specific 1,3-dipolar cycloaddition between the (E)-3-substituted phenyl-acrylic acid derivatives XVIII and the azomethine ylide generated in situ from the N-(methoxymethyl)-N-(phenylmethyl)-N-(trimethylsilyl)methylamine III in the presence of a catalytic amount of acid, such as TFA. Amide derivatives XX were obtained using known methods. Reduction of the amide moiety using standard conditions for example LiAlH$_4$ yielded the aldehyde XXI. Standard Wittig reaction gave the vinyl derivative XXII. Two diastereomeric diols XXIII-A and XXIII-B were obtained using catalytic amount of OsO$_4$ with a combination of co-oxidant such as NMO. The primary hydroxyl group of these diols were selectively silylated by using DMAP as a catalyst to provide respectively XXIV-A and XXIV-B.

A standard Mitsunobu reaction with XXIV-A gave the aryl-ether XXV-A. Selective N-debenzylation was then carried out using known procedures afforded XXVI-A. Amide derivatives were obtained via a coupling with a suitable acid chloride or carboxylic acide using known methods. Deprotection of silyl group provided final derivatives of the type I-4 using known methods such as TBAF. Finally, the diasteromer XXIV-B was converted into I-5 using the same synthetic route (as XXIV into I-4)

Scheme 6

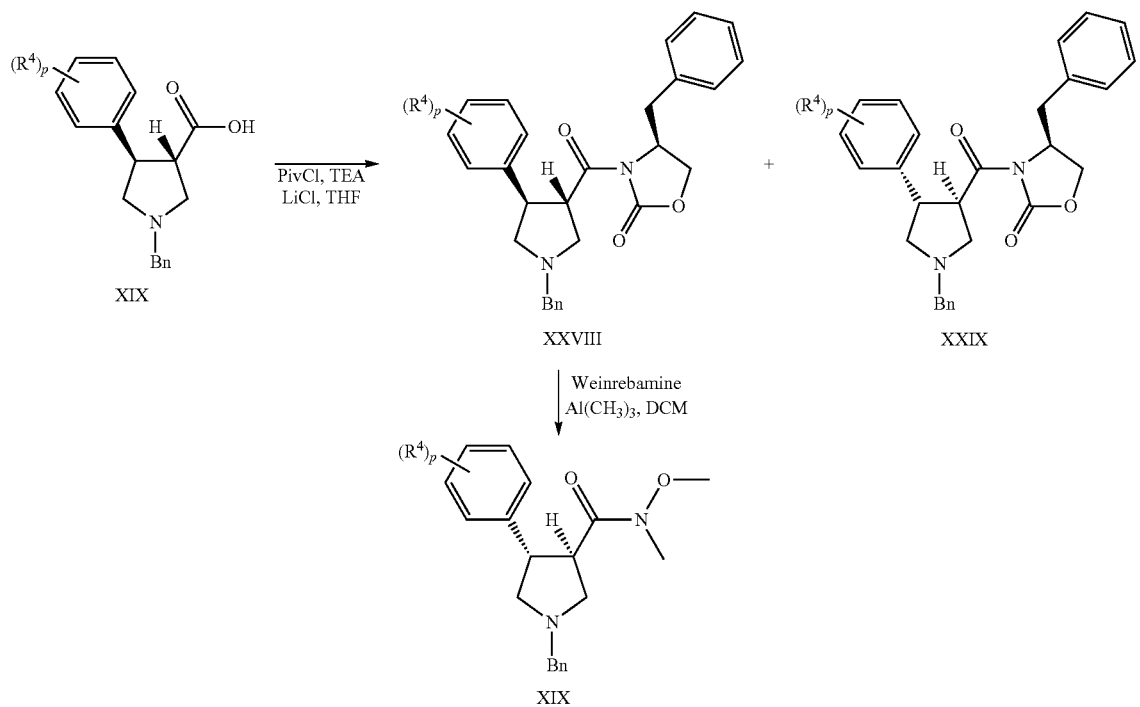

An preparation of the optically pure amide XX is described scheme 6. The racemic carboxylic acid derivatives XIX were converted into the two diastereomerics oxazolidinone derivatives XXVIII and XXIX, which were readily separated using chromatography on silica gel. XXVIII was converted into the corresponding amide XX using a known condition, such as a combination of trimethylaliminum and amine.

Scheme 7

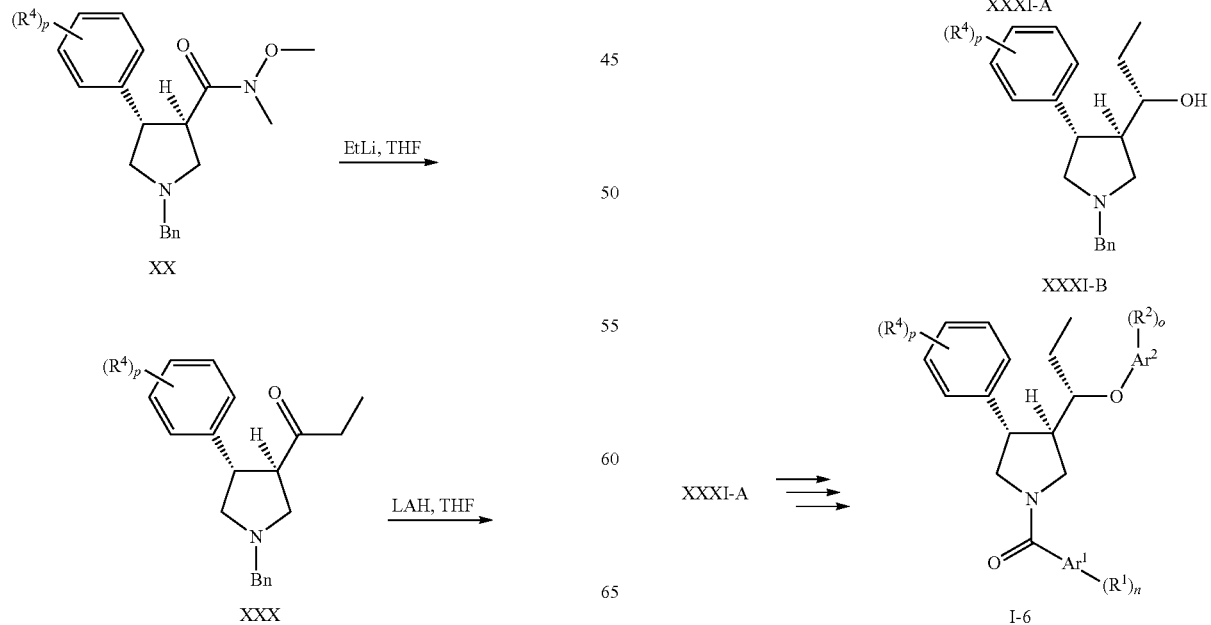

-continued

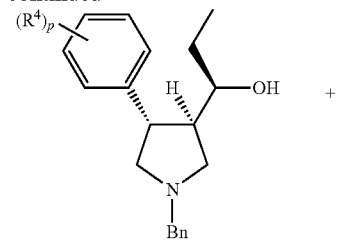
XXXI-A

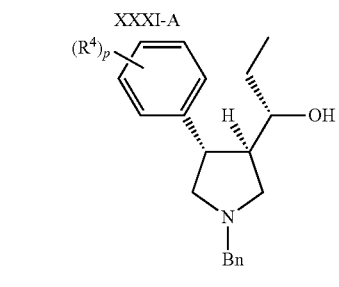
XXXI-B

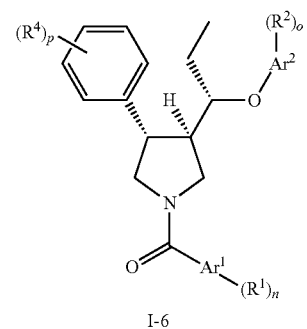
I-6

XXXI-B 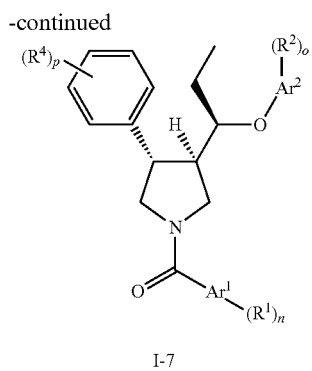

I-7

The scheme 7 described the synthesis of derivatives of the type I with $R^3$ is an ethyl moiety. Treatment of the amide derivatives XX with ethyl lithium provided the ketone derivatives XXX. Reduction of the carbonyl moiety using standard conditions for example $LiAlH_4$ yielded the alcohol XXXI-A and XXXI-B which were then converted respectively into I-6 and I-7 using the same synthetic route described scheme 2.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

As mentioned earlier, the compounds of formula I and their pharmaceutically usable addition salts possess valuable pharmacological properties. Compounds of the present invention are antagonists of neurokinin 3 (NK-3) receptors. The compounds were investigated in accordance with the tests given hereinafter.

Experimental Procedure

The compounds were investigated in accordance with the tests given hereinafter.

[$^3$H]SR$^{142801}$ Competition Binding Assay hNK3 receptor binding experiment were performed using [$^3$H]SR$^{142801}$ (Catalog No. TRK1035, specific activity: 74.0 Ci/mmol, Amersham, GE Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM $MnCl_2$, 1 µM phosphoramidon, 0.1% BSA binding buffer at pH 7.4 to a final assay concentration of 5 µg protein/well. For inhibition experiments, membranes were incubated with [$^3$H]SR$^{142801}$ at a concentration equal to $K_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI +0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Canberra Packard S.A., Zutrich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). $IC_{50}$ values were derived from the inhibition curve and the affinity constant ($K_i$) values were calculated using the Cheng-Prussoff equation $K_i=IC_{50}/(1+[L]/K_D)$ where [L] is the concentration of radioligand and $K_D$ is its dissociation constant at the receptor, derived from the saturation isotherm. All experiments were performed in duplicate and the mean ± standard error (SEM) of the individual $K_i$ values was calculated.

Some results of representative compounds of the hNK-3 receptor affinity are shown in the following Table 1.

TABLE 1

| Example No. | $K_i$NK3 h (µM) |
|---|---|
| 2 | 0.0355 |
| 6 | 0.0636 |
| 9 | 0.0798 |
| 10 | 0.0032 |
| 11 | 0.0118 |
| 12 | 0.0194 |
| 13 | 0.05 |
| 14 | 0.0278 |
| 15 | 0.0063 |
| 16 | 0.0092 |
| 17 | 0.0118 |
| 18 | 0.0227 |
| 19 | 0.0058 |
| 20 | 0.017 |
| 21 | 0.0056 |
| 25 | 0.0633 |
| 26 | 0.066 |
| 28 | 0.059 |
| 30 | 0.08 |
| 31 | 0.005 |
| 34 | 0.047 |
| 35 | 0.002 |
| 36 | 0.084 |
| 37 | 0.0316 |
| 38 | 0.0156 |
| 39 | 0.0093 |
| 40 | 0.0068 |
| 41 | 0.0664 |
| 42 | 0.0255 |
| 43 | 0.0246 |
| 44 | 0.0118 |
| 45 | 0.0073 |
| 46 | 0.0019 |
| 47 | 0.0125 |
| 48 | 0.0426 |
| 49 | 0.0223 |
| 50 | 0.0046 |
| 51 | 0.0787 |
| 52 | 0.0054 |
| 54 | 0.002 |
| 55 | 0.0065 |
| 56 | 0.0043 |
| 57 | 0.0234 |
| 58 | 0.0005 |
| 59 | 0.0021 |
| 60 | 0.0011 |
| 61 | 0.0014 |
| 62 | 0.0594 |
| 63 | 0.0021 |
| 64 | 0.0357 |
| 65 | 0.0026 |
| 66 | 0.0038 |
| 67 | 0.0058 |
| 68 | 0.0147 |
| 69 | 0.0289 |
| 70 | 0.0349 |
| 71 | 0.0061 |
| 72 | 0.0209 |
| 73 | 0.0068 |
| 74 | 0.0186 |
| 75 | 0.0336 |
| 76 | 0.0035 |
| 77 | 0.0328 |

TABLE 1-continued

| Example No. | $K_iNK3\ h\ (\mu M)$ |
|---|---|
| 78 | 0.0272 |
| 79 | 0.0272 |
| 80 | 0.0015 |
| 81 | 0.0048 |
| 82 | 0.0032 |
| 83 | 0.0006 |
| 84 | 0.022 |
| 85 | 0.0075 |
| 86 | 0.0043 |
| 87 | 0.0562 |
| 89 | 0.0091 |
| 90 | 0.011 |
| 91 | 0.0184 |
| 92 | 0.0338 |
| 93 | 0.0646 |
| 95 | 0.0524 |
| 97 | 0.0675 |
| 98 | 0.0457 |
| 101 | 0.046 |
| 102 | 0.0914 |
| 103 | 0.0257 |
| 104 | 0.004 |
| 106 | 0.0309 |
| 107 | 0.0026 |
| 108 | 0.0028 |
| 109 | 0.0241 |
| 110 | 0.0177 |
| 111 | 0.0037 |
| 112 | 0.005 |
| 113 | 0.0177 |
| 114 | 0.0854 |
| 115 | 0.004 |
| 116 | 0.028 |
| 117 | 0.027 |
| 119 | 0.003 |

The present invention also provides pharmaceutical compositions containing compounds of the invention, or pharmaceutically acceptable salts thereof, and a pharmaceutically acceptable carrier. Such pharmaceutical compositions can be in the form of tablets, coated tablets, dragees, hard and soft gelatin capsules, solutions, emulsions or suspensions. The pharmaceutical compositions can also be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. gelatinLactose, corn starch or derivatives thereof, talc, stearic acid or its salts etc can be used as such excipients e.g. for tablets, dragees and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions, or suspensions. The pharmaceutical compositions also can be administered rectally, for example, in the form of suppositories or parenterally, for example, in the form of injection solutions.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch firstly can be mixed in a mixer and then in a comminuting machine. The mixture then can be returned to the mixer; the talc can be added thereto and mixed thoroughly. The mixture can be filled by machine into hard gelatin capsules.

EXAMPLE C

Suppositories of the following composition are manufactured:

|  | mg/supp. |
|---|---|
| Active substance | 15 |
| Suppository mass | 1285 |
| Total | 1300 |

The suppository mass can be melted in a glass or steel vessel, mixed thoroughly and cooled to 45° C. Thereupon, the finely powdered active substance can be added thereto and stirred until it has dispersed completely. The mixture then can be poured into suppository moulds of suitable size, left to cool, the suppositories then can be removed from the moulds and packed individually in wax paper or metal foil.

The following Examples illustrate the present invention without limiting it. All temperatures are given in degrees Celsius.

Experimental Procedures

Abbreviations:

$CH_2Cl_2$ dichloromethane;

DMAP dimethylaminopyridine;

HOBt=1-hydroxy-benzotriazol hydrat;

EDC=1-(3-dimethylaminopropyl)-3-ethylcarbodiimide hydrochloride;

$Et_3N$=triethylamine;

EtOAc=ethyl acetate;

H=hexane;

RT=room temperature;

$PPh_3$=triphenylphosphine;

DBAD=di-tert-butyl azodicarboxylate.

General Procedure I: Amid Coupling (Pyrrolidine XII and Carboxylic Acid)

To a stirred solution of a carboxylic acid derivative (commercially available or known in the literature) (1 mmol) in 10 mL of $CH_2Cl_2$ was added (1.3 mmol) of EDC, (1.3 mmol) of HOBt and $Et_3N$ (1.3 mmol). After one hour at RT, was added a pyrrolidine intermediate of general formula (XII). The mixture was stirred at RT over night and then poured onto water and extracted with $CH_2Cl_2$. The combined organic phases were dried over $Na_2SO_4$ and concentrated under vacuo. Flash chromatography or preparative HPLC afforded the title compound.

General Procedure II: Coupling Between a Compound of Formula XII and an Acid Chloride A solution of the pyrrolidine (1 mmol) of formula (XII) in $CH_2Cl_2$ (10 mL) was treated with $Et_3N$ (1.2 mmol) and an acid chloride (1.2 mmol) and stirred at RT overnight. Purification by preparative HPLC yielded the title compound.

General procedure III: Mitsunobu Reaction $PPh_3$ bound on resin (2.2 mmol) was put in suspension in THF (50 mL). Then the DBAD (1.6 mmol) and the phenol, pyridin-ol or pyrimidin-ol (1.5 mmol) were added. After 5 min at RT, the alcohol of formula V, XI or XV was added and stirring was continued at RT overnight. The reaction mixture was filtered on celite and then concentrated under vacuo. The crude residue was dissolved in EtOAc, washed with aq. NaOH (1M) and the organic phase was dried over $Na_2SO_4$. Column chromatography or preparative HPLC yielded the title compound.

Description of Pyrrolidine Intermediates of Formula XII-B, XV-A and XV-B

Pyrrolidine Intermediates of Formula XII-B

Pyrrolidine XII-B-1

(3RS,4SR)-3-(3,4-Dichloro-phenyl)-4-[(RS)-1-(4-trifluoromethyl-phenoxy)-ethyl]-pyrrolidine

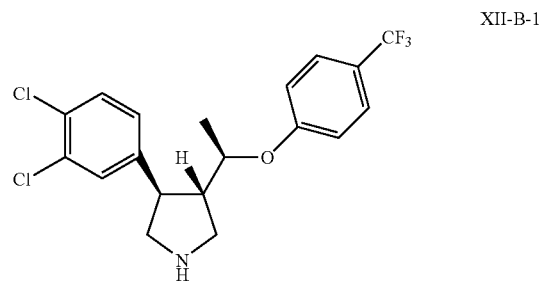

XII-B-1 a) 1-[(3SR,4RS)-1-Benzyl-4-(3,4-dichloro-phenyl)-pyrrolidin-3-yl]-ethanone (IX-1)

A solution of N-(methoxymethyl)-N-(phenylmethyl)-N-(trimethylsilyl)methylamine (32.78 g, 0.138 mol) in $CH_2Cl_2$ (50 mL) was added dropwise, over a 30 minutes period, to a stirred solution of (E)-4-(3,4-dichloro-phenyl)-but-3-en-2-one (19.80 g, 0.092 mol) and trifluoroacetic acid (1.05 mL, 0.009 mol) in $CH_2Cl_2$ (100 mL) at 0° C. The ice bath was removed, and the solution was stirred at 25° C. for an additional 48 h. It was then concentrated and purification by flash chromatography ($SiO_2$, $CH_2Cl_2$/MeOH 98:2) afforded 28.3 g (88%) of the title compound as a yellow oil. ES-MS m/e: 348.2 (M+H$^+$).

b) (RS)-1-[(3SR,4RS)-1-benzyl-4-(3,4-Dichloro-phenyl)-pyrrolidin-3-yl]-ethanol (X-A-1) and (SR)-1-[(3SR,4RS)-1-benzyl-4-(3,4-Dichloro-phenyl)-pyrrolidin-3-yl]-ethanol (X-B-1)

To a solution of 1-[(3SR,4RS)-1-benzyl-4-(3,4-dichloro-phenyl)-pyrrolidin-3-yl]-ethanone (IX-1) (14.90 g, 0.043 mol) in THF (300 mL) at 0° C. were added portion wise $LiAlH_4$ (2.05 g, 0.051 mol). Stirring was continued for one hour, and the reaction mixture was carefully quenched by addition of aq. $NH_4Cl$, concentrated under vacuo and the product extracted with EtOAC. The combined organic phases were dried on $Na_2SO_4$ and concentrated under vacuo. The two diastereoisomeres were separated by column chromatography ($SiO_2$, EtOAc/H, 1:1) to yield (SR)-1-[(3SR,4RS)-1-benzyl-4-(3,4-dichloro-phenyl)-pyrrolidin-3-yl]-ethanol (X-B-1) 4.69 g (31%) as awhite solid ES-MS m/e: 350.2 (M+H$^+$) and (RS)-1-[(3SR,4RS)-1-benzyl-4-(3,4-dichloro-phenyl)-pyrrolidin-3-yl]-ethanol (X-A-1) 5.30 g (35%) as awhite solid ES-MS m/e: 350.2 (M+H$^+$).

c) (3RS,4SR)-1-Benzyl-3-(3,4-dichloro-phenyl)-4-[(RS)-1-(4-trifluoromethyl-phenoxy)-ethyl]-pyrrolidine (XI-B-1)

To a suspension of $PPh_3$ ($PPh_3$ polymer bound, 3 mmol $PPh_3$/g resin) (1.80 g, 5.59 mmol) in THF (40 mL) at 0° C.

were added 4-trifluoromethyl-phenol(0.618 g, 3.81 mmol) and then DBAD (0.936 g, 4.07 mmol). After 5 minutes was added (SR)-1-[(3SR,4RS)-1-benzyl-4-(3,4dichloro-phenyl)-pyrrolidin-3-yl]-ethanol (X-B-1) (0.89 g, 2.54 mmol). The reaction mixture was stirred over night at RT, filtered on celite and concentrated under vacuo. Extraction with EtOAc/aq.NaOH 1M, followed by column chromatography (SiO$_2$, EtOAc/H, 1:6) yielded 0.990 g (79%) of the title compound as a colorless oil. ES-MS m/e: 493.0 (M+H$^+$).

d) (3RS,4SR)-3-(3,4-Dichloro-phenyl)-4-[(RS)-1-(4-trifluoromethyl-phenoxy)-ethyl]-pyrrolidine (XII-B-1)

To a solution of (3RS,4SR)-1-benzyl-3-(3,4-dichloro-phenyl)-4-[(RS)-1-(4-trifluoromethyl-phenoxy)-ethyl]-pyrrolidine (XI-B-1) 0.99 g (2.00 mmol) dissolved in CH$_3$CN (25 mL) was added 0.40 mL (3.00 mmol) of 2,2,2-trichloroethyl chloroformate and stirring was continued for 4 hours at RT. Volatiles were removed under vacuo, and the crude was dissolved in AcOH (20 mL) before a total of 800 mg of Zn dust was added portion wise. After three hours at RT, the reaction mixture was filtered on celite, the solvent removed under vacuo, followed by extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.54 g (67%) of the title compound as a colorless oil. ES-MS m/e: 404.2 (M+H$^+$).

Pyrrolidine XII-B-2

5-Chloro-2-{(RS)-1-[(3SR,4RS)-4-(3,4-dichloro-phenyl)-pyrrolidin-3-yl]-ethoxy}-pyridine

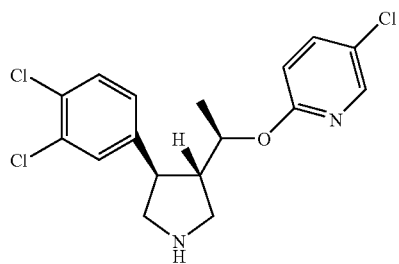

XII-B-2 a) 2-{(RS)-1-[(3SR,4RS)-1-Benzyl-4-(3,4-dichloro-phenyl)-pyrrolidin-3-yl]-ethoxy}-5-chloro-pyridine (XI-B-2)

To a suspension of PPh$_3$ (PPh$_3$ polymer bound, 3 mmol PPh$_3$/g resin) (3.14 g, 9.4 mmol) in THF (70 mL) at 0° C. were added 5-chloro-pyridin-2-ol (0.832 g, 6.42 mmol) and then DBAD (1.578 g, 6.85 mmol). After 5 minutes was added (SR)-1-[(3SR,4RS)-1-benzyl-4-(3,4-dichloro-phenyl)-pyrrolidin-3-yl]-ethanol (X-B-1) (1.50 g, 4.28 mmol). The reaction mixture was stirred over night at RT, filtered on celite and concentrated under vacuo. Extraction with EtOAc/aq.NaOH 1M, followed by column chromatography (SiO$_2$, EtOAc/H, 1:6) yielded 1.71 g (87%) of the title compound as a colorless oil. ES-MS m/e: 461.2 (M+H$^+$).

b) 5-Chloro-2-{(RS)-1-[(3SR,4RS)-4-(3,4-dichloro-phenyl)-pyrrolidin-3-yl]-ethoxy}-pyridine (XII-B-2)

To a solution of 2-{(RS)-1-[(3SR,4RS)-1-benzyl-4-(3,4-dichloro-phenyl)-pyrrolidin-3-yl]-ethoxy}-5-chloro-pyridine-(XI-B-2) 1.71 g (3.71 mmol) dissolved in CH$_3$CN (50 mL) was added 0.75 mL (5.57 mmol) of 2,2,2-trichloroethyl chloroformate and stirring was continued for 4 hours at RT. Volatiles were removed under vacuo, and the crude was dissolved in AcOH (30 mL) before a total of 1.0 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.74g (54%) of the title compound as a colorless oil. ES-MS m/e: 373.1 (M+H$^+$).

Pyrrolidine XII-B-3

6-{(SR)-1-[(3RS,4SR)-4-(3,4-Dichloro-phenyl)-pyrrolidin-3-yl]-ethoxy}-nicotinonitrile

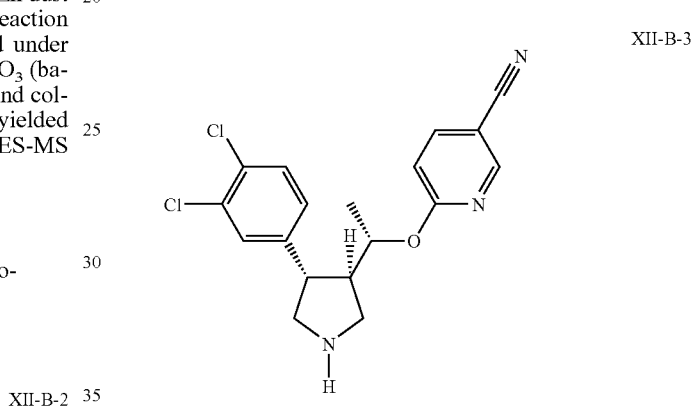

XII-B-3 a) 6-{(SR)-1-[(3RS,4SR)-1-Benzyl-4-(3,4-dichloro-phenyl)-pyrrolidin-3-yl]-ethoxy}-nicotinonitrile (XI-B-3)

To a suspension of PPh$_3$ (PPh$_3$ polymer bound, 3 mmol PPh$_3$/g resin) (1.97 g) in THF (300 mL) at 0° C. were added 6-hydroxy-nicotinonitrile (0.61 g, 5.1 mmol) and then DBAD (1.10 g). After 5 minutes was added (RS)-1-[(3RS,4SR)-1-benzyl-4-(3,4-dichloro-phenyl)-pyrrolidin-3-yl]-ethanol (1.20 g, 3.4 mmol, described herein above). The reaction mixture was stirred over night at RT, filtered on celite and concentrated under vacuo. Extraction with EtOAc/aq.NaOH 1M, followed by column chromatography (SiO$_2$, EtOAc/H, 1:4) yielded 1.02 g (66%) of the title compound as a colorless oil. ES-MS m/e: 452.0 (M+H$^+$).

b) 6-{(SR)-1-[(3RS,4SR)-4-(3,4-Dichloro-phenyl)-pyrrolidin-3-yl]-ethoxy}-nicotinonitrile (XII-B-3)

To a solution of 6-{(SR)-1-[(3RS,4SR)-1-benzyl-4-(3,4-dichloro-phenyl)-pyrrolidin-3-yl]-ethoxy}-nicotinonitrile 0.75 g (1.70 mmol) dissolved in CH$_3$CN (50 mL) was added 0.56 mL (4.14 mmol) of 2,2,2-trichloroethyl chloroformate and stirring was continued for 4 hours at RT. Volatiles were removed under vacuo, and the crude was dissolved in AcOH (30 mL) before a total of 0.45 g of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1) yielded 0.36 g (60%) of the title compound as a colorless oil. ES-MS m/e: 362.3 (M+H$^+$).

Pyrrolidine XII-B-4

2-{(SR)-1-[(3RS,4SR)-4-(3,4-Dichloro-phenyl)-pyrrolidin-3-yl]-ethoxy}-5-trifluoromethyl-pyridine

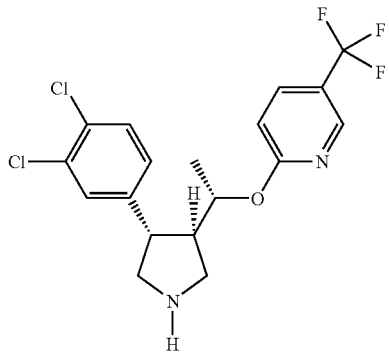

XII-B-4 a) 2-{(SR)-1-[(3RS,4SR)-1-Benzyl-4-(3,4-dichloro-phenyl)-pyrrolidin-3-yl]-ethoxy}-5-trifluoromethyl-pyridine (XI-B-4)

To a suspension of PPh$_3$ (PPh$_3$ polymer bound, 3 mmol PPh$_3$/g resin) (0.77 g) in THF (25 mL) at 0° C. were added 5-trifluoromethyl-pyridin-2-ol (0.28 g, 1.75 mmol) and then DBAD (0.43 g). After 5 minutes was added (RS)-1-[(3RS, 4SR)-1-benzyl-4-(3,4-dichloro-phenyl)-pyrrolidin-3-yl]-ethanol (0.41 g, 1.17 mmol, described herein above). The reaction mixture was stirred over night at RT, filtered on celite and concentrated under vacuo. Extraction with EtOAc/aq.NaOH 1M, followed by column chromatography (SiO$_2$, EtOAc/H, 1:4) yielded 0.45 g (78%) of the title compound as a colorless oil. ES-MS m/e: 495.8 (M+H$^+$).

b) 2-{(SR)-1-[(3RS,4SR)-4-(3,4-Dichloro-phenyl)-pyrrolidin-3-yl]-ethoxy}-5-trifluoromethyl-pyridine (XII-B-4)

To a solution of 2-{(SR)-1-[(3RS,4SR)-1-benzyl-4-(3,4-dichloro-phenyl)-pyrrolidin-3-yl]-ethoxy}-5-trifluoromethyl-pyridine 0.45 g (0.91 mmol) dissolved in toluene (5 mL) were added 0.30 mL (2.7 mmol) of 1-chloroethyl chloroformate and 0.46 mL of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 0.32 g (87%) of the title compound as a light yellow oil. ES-MS m/e: 405.9 (M+H$^+$).

Pyrrolidine XII-B-5

5-Chloro-2-{(S)-1-[(3R,4S)-4-(3-chloro-4-fluoro-phenyl)-pyrrolidin-3-yl]-ethoxy}-pyridine

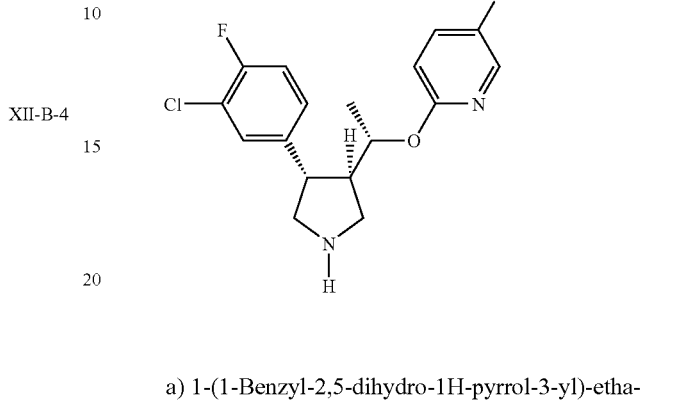

XII-B-5 a) 1-(1-Benzyl-2,5-dihydro-1H-pyrrol-3-yl)-ethanone (XVII)

To a solution of N-(methoxymethyl)-N-(phenylmethyl)-N-(trimethylsilyl)methylamine (9.76 g, 0.041 mol) in CH$_2$Cl$_2$ (40 mL) at 0° C., was added dropwise over a 5 minutes period but-3-yn-2-one (2.0 g, 0.029 mol) followed by trifluoroacetic acid (0.22 mL, 0.003 mol) (very exothermic reaction). The ice bath was removed after 30 minutes, and the solution was stirred at 25° C. for an additional 2 h. It was then concentrated and purification by flash chromatography (SiO$_2$, EtOAc/Heptane 1:1) afforded 2.90 g (49%) of the title compound as a yellow oil. ES-MS m/e: 202.2 (M+H$^+$).

b) 1-[(3R,4S)-1-Benzyl-4-(3-chloro-4-fluoro-phenyl)-pyrrolidin-3-yl]-ethanone (IX-5)

A two necked flask was charged under argon with rhodium (acac)bis ethylene (31 mg, 0.05 eq.), (R)-BINAP (76 mg, 0.05 eq.) and 3-chloro-4-fluoro-phenylboronic acid (850 mg, 2.0 eq.). 60 mL of MeOH and 6.0 mL of H$_2$O were added followed by 1-(1-benzyl-2,5-dihydro-1H-pyrrol-3-yl)-ethanone. The reaction mixture was heated at 60° C. for 2 hours, cooled down to RT and concentrated under vacuo. Purification by flash chromatography (SiO$_2$, EtOAc/Heptane 2/1) afforded 180 mg (22%) of the title product as a light yellow oil.

c) (S)-1-[(3R,4S)-1-Benzyl-4-(3-chloro-4-fluoro-phenyl)-pyrrolidin-3-yl]-ethanol (X-A-5) and (R)-1-[(3R,4S)-1-Benzyl-4-(3-chloro-4-fluoro-phenyl)-pyrrolidin-3-yl]-ethanol (X-B-5)

To a solution of 1-[(3R,4S)-1-benzyl-4-(3-chloro-4-fluoro-phenyl)-pyrrolidin-3-yl]-ethanone (191 mg, 0.57 mmol) in THF (7 mL) at 0° C. were added portion wise LiAlH$_4$ (19 mg, 0.50 mmol). Stirring was continued for one hour, and the reaction mixture was carefully quenched by addition of aq. NH$_4$Cl, concentrated under vacuo and the product extracted with EtOAC. The combined organic phases were dried on Na$_2$SO$_4$ and concentrated under vacuo. The two diastereoisomeres were separated by column chromatography (SiO$_2$, EtOAc/H, 1:1) to yield (R)-1-[(3R,4S)-1-benzyl-4-(3-chloro-4-fluoro-phenyl)-pyrrolidin-3-yl]-ethanol (X-B-5) 81 mg (42%) as a white solid ES-MS m/e: 334.2 (M+H$^+$) and (S)-1-[(3R,4S)-1-benzyl-4-(3-chloro-4-fluoro-phenyl)-pyrrolidin-3-yl]-ethanol (X-A-5) 43 mg (22%) as a white solid ES-MS m/e: 334.2 (M+H$^+$).

d) 2-{(S)-1-[(3R,4S)-1-Benzyl-4-(3-chloro-4-fluoro-phenyl)-pyrrolidin-3-yl]-ethoxy}-5-chloro-pyridine (XI-B-5)

To a suspension of PPh$_3$ (PPh$_3$ polymer bound, 3 mmol PPh$_3$/g resin) (141 mg, 0.53 mmol) in THF (8 mL) at 0° C. were added 5-chloro-pyridin-2-ol (47 mg, 0.36 mmol) and then DBAD (90 mg, 0.39 mmol). After 5 minutes was added (R)-1-[(3R,4S)-1-benzyl-4-(3-chloro-4-fluoro-phenyl)-pyrrolidin-3-yl]-ethanol (81 mg, 0.24 mmol). The reaction mixture was stirred over night at RT, filtered on celite and concentrated under vacuo. Extraction with EtOAc/aq.NaOH 1M, followed by column chromatography (SiO$_2$, EtOAc/H, 1:3) yielded 88 mg (81%) of the title compound as a colorless oil. ES-MS m/e: 446.2 (M+H$^+$).

e) 5-Chloro-2-{(S)-1-[(3R,4S)-4-(3-chloro-4-fluoro-phenyl)-pyrrolidin-3-yl]-ethoxy}-pyridine (XII-B-5)

To a solution of 2-{(S)-1-[(3R,4S)-1-benzyl-4-(3-chloro-4-fluoro-phenyl)-pyrrolidin-3-yl]-ethoxy}-5-chloro-pyridine 88 mg (0.19 mmol) dissolved in toluene (2 mL) were added 0.06 mL (0.57 mmol) of 1-chloroethyl chloroformate and 0.10 mL of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 43 mg (61%) of the title compound as a light yellow oil. ES-MS m/e: 355.1 (M+H$^+$).

Pyrrolidine XII-B-6

6-{(S)-1-[(3R,4S)-4-(3-Chloro-4-fluoro-phenyl)-pyrrolidin-3-yl]-ethoxy}-nicotinonitrile

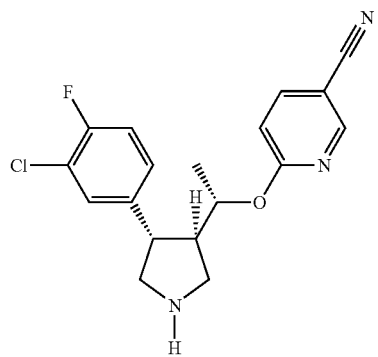

a) 6-{(S)-1-[(3R,4S)-1-Benzyl-4-(3-chloro-4-fluoro-phenyl)-pyrrolidin-3-yl]-ethoxy}-nicotinonitrile (XI-B-6)

To a stirred solution of 43 mg (0.13 mmol) of (S)-1-[(3R,4S)-1-benzyl-4-(3-chloro-4-fluoro-phenyl)-pyrrolidin-3-yl]-ethanol in DMF (5 mL) was added NaH (9 mg, 0.18 mmol). The reaction mixture was stirred at RT for 30 minutes, and then at 50° C. for 20 minutes. A solution of 6-chloro-nicotinonitrile (22 mg, 0.16 mmol) in DMF (1 mL) was added dropwise and stirring was continued 3 hours at 50° C. The reaction mixture was concentrated under vacuo. Extraction with EtOAc/H$_2$O, followed by column chromatography (SiO$_2$, EtOAc/H, 1:3) yielded 48 mg (86%) of the title compound as a colorless oil. ES-MS m/e: 436.1 (M+H$^+$).

b) 6-{(S)-1-[(3R,4S)-4-(3-Chloro-4-fluoro-phenyl)-pyrrolidin-3-yl]-ethoxy}-nicotinonitrile (XII-B-6)

To a solution of 6-{(S)-1-[(3R,4S)-1-benzyl-4-(3-chloro-4-fluoro-phenyl)-pyrrolidin-3-yl]-ethoxy}-nicotinonitrile 48 mg (0.11 mmol) dissolved in toluene (1 mL) were added 47 mg (0.33 mmol) of 1-chloroethyl chloroformate and 43 mg (0.33 mmol) of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 28 mg (72%) of the title compound as a light yellow oil. ES-MS m/e: 346.1 (M+H$^+$).

Pyrrolidine XII-B-7

5-Chloro-2-{(S)-1-[(3R,4S)-4-(3,4-difluoro-phenyl)-pyrrolidin-3-yl]-ethoxy}-pyridine

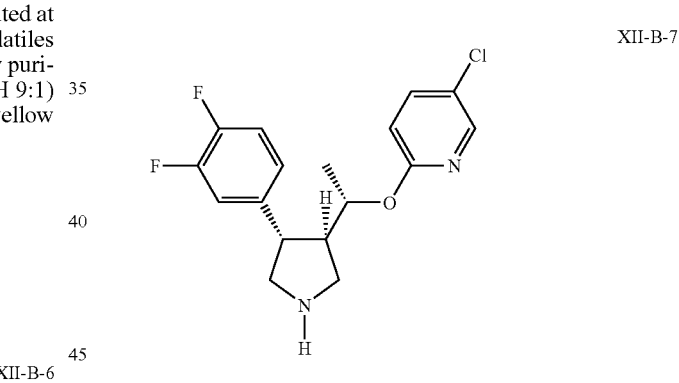

a) 1-[(3R,4S)-1-Benzyl-4-(3,4-difluoro-phenyl)-pyrrolidin-3-yl]-ethanone (IX-7)

A two necked flask was charged under argon with rhodium (acac)bis ethylene (0.239 g, 0.05 eq.), (R)-BINAP (0.575 g, 0.05 eq.) and 3,4-difluoro-phenylboronic acid (7.3 g, 2.5 eq.). 400 mL of MeOH and 40 mL of H$_2$O were added followed by 1-(1-benzyl-2,5-dihydro-1H-pyrrol-3-yl)-ethanone (3.72 g). The reaction mixture was heated at 55° C. for 8 hours, cooled down to RT and concentrated under vacuo. Purification by flash chromatography (SiO$_2$, EtOAc/Heptane 2/1) afforded 2.31 g (40%) of the title product as a light yellow oil. ES-MS m/e: 316.1 (M+H$^+$).

b) (S)-1-[(3R,4S)-1-Benzyl-4-(3,4-difluoro-phenyl)-pyrrolidin-3-yl]-ethanol (X-A-7) and (R)-1-[(3R,4S)-1-Benzyl-4-(3,4-difluoro-phenyl)-pyrrolidin-3-yl]-ethanol (X-B-7)

To a solution of 1-[(3R,4S)-1-benzyl-4-(3,4-difluoro-phenyl)-pyrrolidin-3-yl]-ethanone (2.31 g, 7.32 mmol) in THF (80 mL) at 0° C. were added portion wise LiAlH₄ (0.245 g, 6.44 mmol). Stirring was continued for one hour, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomeres were separated by column chromatography (SiO₂, EtOAc/H, 1:1) to yield (R)-1-[(3R,4S)-1-benzyl-4-(3,4-difluoro-phenyl)-pyrrolidin-3-yl]-ethanol (X-B-7) 0.98 g (42%) as a white solid ES-MS m/e: 318.1(M+H⁺) and (S)-1-[(3R,4S)-1-benzyl-4-(3,4-difluoro-phenyl)-pyrrolidin-3-yl]-ethanol (X-A-7) 0.86 g (37%) as a white solid ES-MS m/e: 318.1 (M+H⁺).

c) 2-{(S)-1-[(3R,4S)-1-Benzyl-4-(3,4-difluoro-phenyl)-pyrrolidin-3-yl]-ethoxy}-5-chloro-pyridine (XI-B-7)

To a suspension of PPh₃ (PPh₃ polymer bound, 3 mmol PPh₃/g resin) (1.78 g, 6.79 mmol) in THF (20 mL) at 0° C. were added 5-chloro-pyridin-2-ol (0.60 g, 4.63 mmol) and then DBAD (1.14 g, 4.95 mmol). After 5 minutes was added (R)-1-[(3R,4S)-1-benzyl-4-(3,4-difluoro-phenyl)-pyrrolidin-3-yl]-ethanol (0.98 g, 3.09 mmol). The reaction mixture was stirred over night at RT, filtered on celite and concentrated under vacuo. Extraction with EtOAc/aq.NaOH 1M, followed by column chromatography (SiO₂, EtOAc/H, 1:3) yielded 0.917 g (69%) of the title compound as a colorless oil. ES-MS m/e: 429.2 (M+H⁺).

d) 5-Chloro-2-{(S)-1-[(3R,4S)-4-(3,4-difluoro-phenyl)-pyrrolidin-3-yl]-ethoxy}-pyridine (XII-B-7)

To a solution of 2-{(S)-1-[(3R,4S)-1-benzyl-4-(3,4-difluoro-phenyl)-pyrrolidin-3-yl]ethoxy}-5-chloro-pyridine 917 mg (2.13 mmol) dissolved in toluene (20 mL) were added 0.69 mL (6.39 mmol) of 1-chloroethyl chloroformate and 1.09 mL (6.39 mL) of Hunig's base. The reaction mixture was heated at 100° C. for one hour. After cooling down to RT, volatiles were removed under vacuo and the crude was dissolved in MeOH (20 mL). The reaction mixture was heated at 85° C. for 30 minutes and after cooling down to RT, volatiles were removed under vacuo and the residue was directly purified on column-chromatography (SiO₂, CH₂Cl₂/MeOH 9:1) yielded 464 mg (64%) of the title compound as a light yellow oil. ES-MS m/e: 339.1 (M+H⁺).

Pyrrolidine XII-B-8

6-{(S)-1-[(3R,4S)-4-(3,4-Difluoro-phenyl)-pyrrolidin-3-yl]-ethoxy}-nicotinonitrile

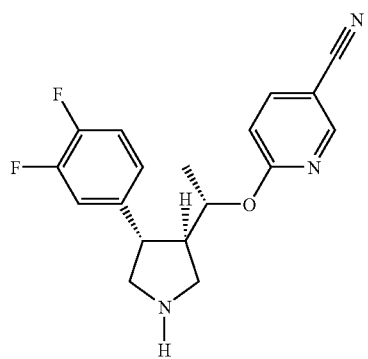

XII-B-8 a) 6-{(S)-1-[(3R,4S)-1-Benzyl-4-(3,4-difluoro-phenyl)-pyrrolidin-3-yl]-ethoxy}-nicotinonitrile (XI-B-8)

To a stirred solution of 84 mg (0.26 mmol) of (S)-1-[(3R,4S)-1-benzyl-4-(3,4-difluoro-phenyl)-pyrrolidin-3-yl]-ethanol in DMF (10 mL) was added NaH (19 mg, 0.40 mmol). The reaction mixture was stirred at RT for 30 minutes, and then at 50° C. for 20 minutes. A solution of 6-chloro-nicotinonitrile (45 mg, 0.32 mmol) in DMF (2 mL) was added dropwise and stirring was continued 3 hours at 50° C. The reaction mixture was concentrated under vacuo. Extraction with EtOAc/H₂O, followed by column chromatography (SiO₂, EtOAc/H, 1:3) yielded 66 mg (60%) of the title compound as a colorless oil. ES-MS m/e: 420.3 (M+H⁺).

b) 6-{(S)-1-[(3R,4S)-4-(3,4-Difluoro-phenyl)-pyrrolidin-3-yl]-ethoxy}-nicotinonitrile (XII-B-8)

To a solution of 6-{(S)-1-[(3R,4S)-1-benzyl-4-(3,4-difluoro-phenyl)-pyrrolidin-3-yl]-ethoxy}-nicotinonitrile 66 mg (0.16 mmol) dissolved in toluene (2 mL) were added 67 mg (0.47 mmol) of 1-chloroethyl chloroformate and 61 mg (0.47 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 45 mg (85%) of the title compound as a light yellow oil. ES-MS m/e: 330.3 (M+H⁺).

Pyrrolidine XII-B-9

5-Chloro-2-{(S)-1-[(3R,4S)-4-(4-chloro-3-fluoro-phenyl)-pyrrolidin-3-yl]-ethoxy}-pyridine

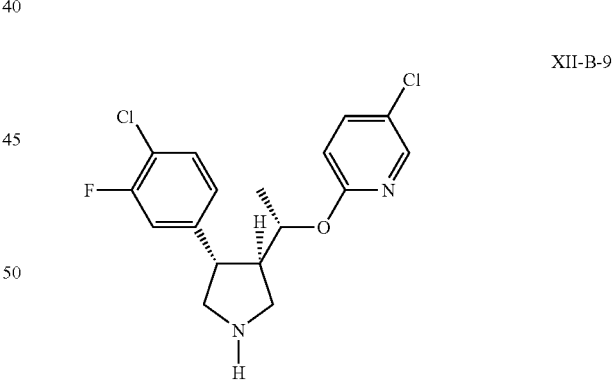

XII-B-9 a) 1-[(3R,4S)-1-Benzyl-4-(4-chloro-3-fluoro-phenyl)-pyrrolidin-3-yl]-ethanone (IX-9)

A two necked flask was charged under argon with rhodium (acac)bis ethylene (31 mg, 0.05 eq.), (R)-BINAP (74 mg, 0.05 eq.) and 4-chloro-3-fluoro-phenylboronic acid (825 mg, 2.5 eq.). 30 mL of MeOH and 3 mL of H₂O were added followed by 1-(1-benzyl-2,5-dihydro-1H-pyrrol-3-yl)-ethanone (480 mg). The reaction mixture was heated at 55° C. for 3 hours, cooled down to RT and concentrated under vacuo. Purification by flash chromatography (SiO₂, EtOAc/Heptane 2/1)

afforded 261 mg (33%) of the title product as a light yellow oil. ES-MS m/e: 332.1 (M+H⁺).

b) (S)-1-[(3R,4S)-1-Benzyl-4-(4-chloro-3-fluoro-phenyl)1-pyrrolidin-3-yl]-ethanol (X-A-9) and (R)-1-[(3R,4S)-1-Benzyl-4-(4-chloro-3-fluoro-phenyl)-pyrrolidin-3-yl]-ethanol (X-B-9)

To a solution of 1-[(3R,4S)-1-benzyl-4-(4-chloro-3-fluoro-phenyl)-pyrrolidin-3-yl]-ethanone (260 mg, 0.78 mmol) in THF (10 mL) at 0° C. were added portion wise LiAlH₄ (26 mg, 0.68 mmol). Stirring was continued for one hour, and the reaction mixture was carefully quenched by addition of aq. NH₄Cl, concentrated under vacuo and the product extracted with EtOAC. The combined organic phases were dried on Na₂SO₄ and concentrated under vacuo. The two diastereoisomeres were separated by column chromatography (SiO₂, EtOAc/H, 1:1) to yield (R)-1-[(3R,4S)-1-benzyl-4-(4-chloro-3-fluoro-phenyl)-pyrrolidin-3-yl]-ethanol (X-B-9) 101 mg (38%) as a white solid ES-MS m/e: 334.2(M+H⁺) and (S)-1-[(3R,4S)-1-benzyl-4-(4-chloro-3-fluoro-phenyl)-pyrrolidin-3-yl]-ethanol (X-A-9) 80 mg (30%) as a white solid ES-MS m/e: 334.2 (M+H⁺).

c) 2-{(S)-1-[(3R,4S)-1-Benzyl-4-(4-chloro-3-fluoro-phenyl)-pyrrolidin-3yl]-ethoxy}-5-chloro-pyridine (XI-B-9)

To a suspension of PPh₃ (PPh₃ polymer bound, 3 mmol PPh₃/g resin) (216 mg, 0.65 mmol) in THF (10 mL) at 0° C. were added 5-chloro-pyridin-2-ol (58 mg, 0.45 mmol) and then DBAD (110 mg, 0.48 mmol). After 5 minutes was added (R)-1-[(3R,4S)-1-benzyl-4-(4-chloro-3-fluoro-phenyl)-pyrrolidin-3-yl]-ethanol (100 mg, 0.30 mmol). The reaction mixture was stirred over night at RT, filtered on celite and concentrated under vacuo. Extraction with EtOAc/aq.NaOH 1M, followed by column chromatography (SiO₂, EtOAc/H, 1:3) yielded 100 mg (75%) of the title compound as a colorless oil. ES-MS m/e: 445.1 (M+H⁺).

d) 5-Chloro-2-{(S)-1-[(3R,4S)-4-(4-chloro-3-fluoro-phenyl)-pyrrolidin-3-yl]-ethoxy}-pyridine (XII-B-9)

To a solution of 2-{(S)-1-[(3R,4S)-1-benzyl-4-(4-chloro-3-fluoro-phenyl)-pyrrolidin-3-yl]-ethoxy}-5-chloro-pyridine 98 mg (0.22 mmol) dissolved in toluene (5 mL) were added 0.072 mL (0.66 mmol) of 1-chloroethyl chloroformate and 0.11 mL (0.66 mL) of Hunig's base. The reaction mixture was heated at 100° C. for one hour. After cooling down to RT, volatiles were removed under vacuo and the crude was dissolved in MeOH (5 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 75 mg (95%) of the title compound as a light yellow oil. ES-MS m/e: 355.1 (M+H⁺).

Pyrrolidine XII-B-10

6-{(S)-1-[(3R,4S)-4-(4-Chloro-3-fluoro-phenyl)-pyrrolidin-3-yl]-ethoxy}-nicotinonitrile

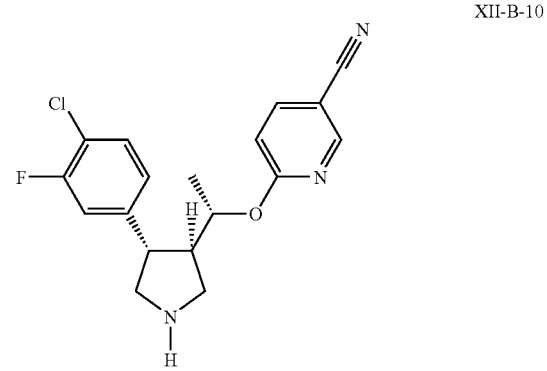

XII-B-10 a) 6-{(S)-1-[(3R,4S)-1-Benzyl-4-(4-chloro-3-fluoro-phenyl)-pyrrolidin-3-yl]-ethoxy}-nicotinonitrile (XI-B-10)

To a stirred solution of 88 mg (0.26 mmol) of (S)-1-[(3R,4S)-1-benzyl-4-(4-chloro-3-fluoro-phenyl)-pyrrolidin-3-yl]-ethanol in DMF (6 mL) was added NaH (19 mg, 0.40 mmol). The reaction mixture was stirred at RT for 30 minutes, and then at 50° C. for 20 minutes. A solution of 6-chloro-nicotinonitrile (45 mg, 0.32 mmol) in DMF (2 mL) was added dropwise and stirring was continued 3 hours at 50° C. The reaction mixture was concentrated under vacuo. Extraction with EtOAc/H₂O, followed by column chromatography (SiO₂, EtOAc/H, 1:3) yielded 100 mg (87%) of the title compound as a colorless oil. ES-MS m/e: 436.2 (M+H⁺).

b) 6-{(S)-1-[(3R,4S)-4-(4-chloro-3-fluoro-phenyl)-pyrrolidin-3-yl]-ethoxy}-nicotinonitrile (XII-B-10)

To a solution of 6-{(S)-1-[(3R,4S)-1-benzyl-4-(4-chloro-3-fluoro-phenyl)-pyrrolidin-3-yl]-ethoxy}-nicotinonitrile_ 100 mg (0.23 mmol) dissolved in toluene (2 mL) were added 98 mg (0.69 mmol) of 1-chloroethyl chloroformate and 89 mg (0.69 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO₂, CH₂Cl₂/MeOH 9:1) yielded 60 mg (76%) of the title compound as a light yellow oil. ES-MS m/e: 346.1 (M+H⁺).

Pyrrolidine XII-B-11

5-Chloro-2-{(S)-1-[(3R,4S)-4-(4-chloro-phenyl)-pyrrolidin-3-yl]-ethoxy}-pyridine

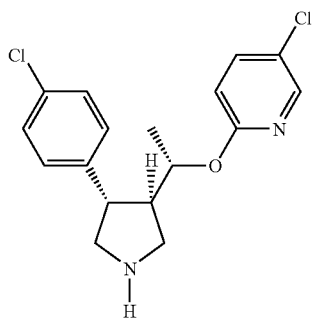

XII-B-11 a) 1-[(3R,4S)-1-Benzyl-4-(4-chloro-phenyl)-pyrrolidin-3-yl]-ethanone (IX-11)

A two necked flask was charged under argon with rhodium (acac)bis ethylene (45 mg, 0.05 eq.), (R)-BINAP (110 mg, 0.05 eq.) and 4-chloro-phenylboronic acid (1.20 g, 2.2 eq.). 100 mL of MeOH and 10 mL of $H_2O$ were added followed by 1-(1-benzyl-2,5-dihydro-1H-pyrrol-3-yl)-ethanone (0.70 g). The reaction mixture was heated at 55° C. for 8 hours, cooled down to RT and concentrated under vacuo. Purification by flash chromatography ($SiO_2$, EtOAc/Heptane 2/1) afforded 0.36 g (33%) of the title product as a light yellow oil. ES-MS m/e: 314.0 (M+H$^+$).

b) (S)-1-[(3R,4S)-1-Benzyl-4-(4-chloro-phenyl)-pyrrolidin-3-yl]-ethanol (X-A-11) and (R)-1-[(3R,4S)-1-Benzyl-4-(4-chloro-phenyl)-pyrrolidin-3-yl]-ethanol (X-B-11)

To a solution of 1-[(3R,4S)-1-benzyl-4-(4-chloro-phenyl)-pyrrolidin-3-yl]-ethanone (0.52 g, 1.65 mmol) in THF (20 mL) at 0° C. were added portion wise $LiAlH_4$ (55 mg, 1.45 mmol). Stirring was continued for one hour, and the reaction mixture was carefully quenched by addition of aq. $NH_4Cl$, concentrated under vacuo and the product extracted with EtOAC. The combined organic phases were dried on $Na_2SO_4$ and concentrated under vacuo. The two diastereoisomers were separated by column chromatography ($SiO_2$, EtOAc/H, 1:1) to yield (R)-1-[(3R,4S)-1-benzyl-4-(4-chloro-phenyl)-pyrrolidin-3-yl]-ethanol (X-B-11) 0.24 g (46%) as a white solid ES-MS m/e: 316.1 (M+H$^+$) and (S)-1-[(3R,4S)-1-benzyl-4-(4-chloro-phenyl)-pyrrolidin-3-yl]-ethanol (X-A-11) 0.25 g (47%) as a white solid ES-MS m/e: 316.1 (M+H$^+$).

c) 2-{(S)-1-[(3R,4S)-1-Benzyl-4-(4-chloro-phenyl)-pyrrolidin-3-yl]-ethoxy}-5-chloro-pyridine (XI-B-11)

To a suspension of $PPh_3$ ($PPh_3$ polymer bound, 3 mmol $PPh_3$/g resin) (0.44 g, 1.69 mmol) in THF (50 mL) at 0° C. were added 5-chloro-pyridin-2-ol (0.15 g, 1.15 mmol) and then DBAD (0.28 g, 1.23 mmol). After 5 minutes was added (R)-1-[(3R,4S)-1-benzyl-4-(4-chloro-phenyl)-pyrrolidin-3-yl]-ethanol (0.25 g, 0.79 mmol). The reaction mixture was stirred over night at RT, filtered on celite and concentrated under vacuo. Extraction with EtOAc/aq.NaOH 1M, followed by column chromatography ($SiO_2$, EtOAc/H, 1:3) yielded 0.22 g (65%) of the title compound as a colorless oil. ES-MS m/e: 427.8 (M+H$^+$).

d) 5-Chloro-2-{(S)-1-[(3R,4S)-4-(4-chloro-phenyl)-pyrrolidin-3-yl]-ethoxy}-pyridine (XII-B-11)

To a solution of 2-{(S)-1-[(3R,4S)-1-benzyl-4-(4-chloro-phenyl)-pyrrolidin-3yl]-ethoxy}-5-chloro-pyridine 220 mg (0.51 mmol) dissolved in toluene (5 mL) were added 0.17 mL (1.53 mmol) of 1-chloroethyl chloroformate and 0.27 mL (1.53 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography ($SiO_2$, $CH_2Cl_2$/MeOH 9:1) yielded 110 mg (62%) of the title compound as a light yellow oil. ES-MS m/e: 337.1 (M+H$^+$).

Pyrrolidine XII-B-12

6-{(S)-1-[(3R,4S)-4-(4-Chloro-phenyl)-pyrrolidin-3-yl]-ethoxy}-nicotinonitrile

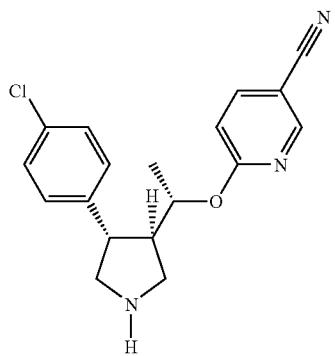

XII-B-12 a) 6-{(S)-1-[(3R,4S)-1-Benzyl-4-(4-chloro-phenyl)-pyrrolidin-3-yl]-ethoxy}-nicotinonitrile (XI-B-12)

To a stirred solution of 250 mg (0.79 mmol) of (S)-1-[(3R,4S)-1-benzyl-4-(4-chloro-phenyl)-pyrrolidin-3-yl]-ethanol in DMF (10 mL) was added NaH (57 mg, 1.18 mmol). The reaction mixture was stirred at RT for 30 minutes, and then at 50° C. for 20 minutes. A solution of 6-chloro-nicotinonitrile (132 mg, 0.95 mmol) in DMF (2 mL) was added dropwise and stirring was continued 3 hours at 50° C. The reaction mixture was concentrated under vacuo. Extraction with EtOAc/$H_2O$, followed by column chromatography ($SiO_2$, EtOAc/H, 1:3) yielded 265 mg (80%) of the title compound as a colorless oil. ES-MS m/e: 418.3 (M+H$^+$).

b) 6-{(S)-1-[(3R,4S)-4-(4-chloro-phenyl)1-pyrrolidin-3-yl]-ethoxy}-nicotinonitrile (XII-B-12)

To a solution of 6-{(S)-1-[(3R,4S)-1-benzyl-4-(4-chloro-phenyl)-pyrrolidin-3-yl]-ethoxy}-nicotinonitrile 265 mg (0.63 mmol) dissolved in toluene (4 mL) were added 0.20 mL (1.89 mmol) of 1-chloroethyl chloroformate and 0.32 mL (1.89 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 148 mg (67%) of the title compound as a light yellow oil. ES-MS m/e: 328.2 (M+H$^+$).

Pyrrolidine XII-B-13

5-Chloro-2-{(S)-1-[(3R,4S)-4-(4-fluoro-phenyl)-pyrrolidin-3-yl]-ethoxy}-pyridine

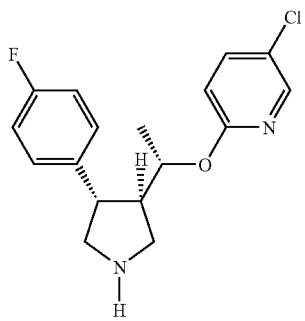

XII-B-13 a) 1-[(3R,4S)-1-Benzyl-4-(4-fluoro-phenyl)-pyrrolidin-3-yl]-ethanone (IX-13)

A two necked flask was charged under argon with rhodium (acac)bis ethylene (185 mg, 0.05 eq.), (R)-BINAP (442 mg, 0.05 eq.) and 4-fluoro-phenylboronic acid (4.87 g, 2.5 eq.). 300 mL of MeOH and 30 mL of H$_2$O were added followed by 1-(1-benzyl-2,5-dihydro-1H-pyrrol-3-yl)-ethanone (2.8 g). The reaction mixture was heated at 60° C. for 8 hours, cooled down to RT and concentrated under vacuo. Purification by flash chromatography (SiO$_2$, EtOAc/Heptane 2/1) afforded 0.40 g (10%) of the title product as a light yellow oil. ES-MS m/e: 298.2 (M+H$^+$).

b) (S)-1-[(3R,4S)-1-Benzyl-4-(4-fluoro-phenyl)-pyrrolidin-3-yl]-ethanol (X-A-13) and (R)-1-[(3R,4S)-1-Benzyl-4-(4-fluoro-phenyl)-pyrrolidin-3-yl]-ethanol (X-B-13)

To a solution of 1-[(3R,4S)-1-benzyl-4-(4-fluoro-phenyl)-pyrrolidin-3-yl]-ethanone (0.38 g, 1.27 mmol) in THF (15 mL) at 0° C. were added portion wise LiAlH$_4$ (43 mg, 1.13 mmol). Stirring was continued for one hour, and the reaction mixture was carefully quenched by addition of aq. NH$_4$Cl, concentrated under vacuo and the product extracted with EtOAC. The combined organic phases were dried on Na$_2$SO$_4$ and concentrated under vacuo. The two diastereoisomeres were separated by column chromatography (SiO$_2$, EtOAc/H, 1:1) to yield (R)-1-[(3R,4S)-1-benzyl-4-(4-fluoro-phenyl)-pyrrolidin-3-yl]-ethanol (X-B-13) 0.16 g (41%) as a white solid ES-MS m/e: 300.2 (M+H$^+$) and (S)-1-[(3R,4S)-1-benzyl-4-(4-fluoro-phenyl)-pyrrolidin-3-yl]-ethanol (X-A-13) 0.15 g (39%) as a white solid ES-MS m/e: 300.2 (M+H$^+$).

c) 2-{(S)-1-[(3R,4S)-1-Benzyl-4-(4-fluoro-phenyl)-pyrrolidin-3-yl]-ethoxy}-5-chloro-pyridine (XI-B-13)

To a suspension of PPh$_3$ (PPh$_3$ polymer bound, 3 mmol PPh$_3$/g resin) (0.36 g, 1.1 mmol) in THF (40 mL) at 0° C. were added 5-chloro-pyridin-2-ol (97 mg, 0.75 mmol) and then DBAD (0.18 g, 0.80 mmol). After 5 minutes was added (R)-1-[(3R,4S)-1-benzyl-4-(4-fluoro-phenyl)-pyrrolidin-3-yl]-ethanol (0.15 g, 0.50 mmol). The reaction mixture was stirred over night at RT, filtered on celite and concentrated under vacuo. Extraction with EtOAc/aq.NaOH 1M, followed by column chromatography (SiO$_2$, EtOAc/H, 1:3) yielded 0.15 g (73%) of the title compound as a colorless oil. ES-MS m/e: 411.2 (M+H$^+$).

d) 5-Chloro-2-{(S)-1-[(3R,4S)-4-(4-fluoro-phenyl)-pyrrolidin-3-yl]-ethoxy}-pyridine (XII-B-13)

To a solution of 2-{(S)-1-[(3R,4S)-1-benzyl-4-(4-fluoro-phenyl)-pyrrolidin-3-yl]-ethoxy}-5-chloro-pyridine 285 mg (0.69 mmol) dissolved in toluene (5 mL) were added 0.22 mL (2.07 mmol) of 1-chloroethyl chloroformate and 0.35 mL (2.07 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography (SiO$_2$, CH$_2$Cl$_2$/MeOH 9:1) yielded 152 mg (68%) of the title compound as a light yellow oil. ES-MS m/e: 321.1 (M+H$^+$).

Pyrrolidine XII-B-14

5-Chloro-2-{(RS)-1-[(3SR,4RS)-4-(2,4-difluoro-phenyl)-pyrrolidin-3-yl]-ethoxy}-pyridine

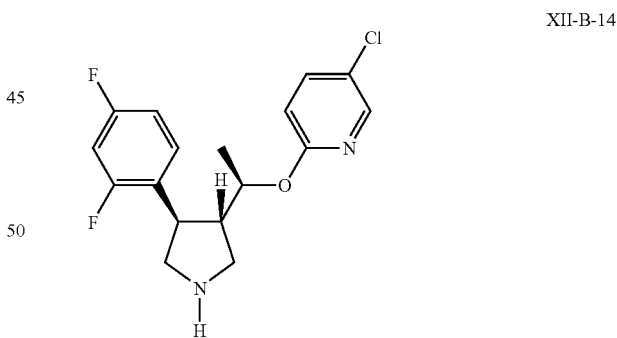

XII-B-14 a) (E)-4-(2,4-Difluoro-phenyl)-but-3-en-2-one

A two necked flask was charged with 2,4-difluorobenzaldehyde (4.0 g, 28.1 mmol) and (2-oxo-propyl)-phosphonic acid dimethyl ester (5.78 g, 33.0 mmol) and cooled down at at 0° C. K$_2$CO$_3$ (7.62 g, 55.1 mmol) in H$_2$O (14 mL) was added dropwise. Stirring was continued over night at RT. The product was extracted with EtOAc, and the organic phase was dried over Na$_2$SO$_4$. Flash chromatography (SiO$_2$, Heptane/EtOAc 1:3) afforded 4.0 g (79%) of the title compound as alight yellow oil.

b) 1-[(3SR,4RS)-1-Benzyl-4-(2,4-difluoro-phenyl)-pyrrolidin-3-yl]-ethanone (IX-14)

A solution of N-(methoxymethyl)-N-(phenylmethyl)-N-(trimethylsilyl)methylamine (7.82 g, 32.9 mmol) in $CH_2Cl_2$ (40 mL) was added dropwise, over a 30 minutes period, to a stirred solution of (E)-4-(2,4-difluoro-phenyl)-but-3-en-2-one (4.0 g, 21.9 mmol) and trifluoroacetic acid (0.17 mL, 0.21 mmol) in $CH_2Cl_2$ (10 mL) at 0° C. The ice bath was removed, and the solution was stirred at 25° C. for an additional 48 h. It was then concentrated and purification by flash chromatography ($SiO_2$, $CH_2Cl_2$/MeOH 98:2) afforded 6.2 g (89%) of the title compound as a yellow oil. ES-MS m/e: 316.1 (M+H$^+$).

c) (RS)-1-[(3SR,4RS)-4-(2,4-Difluoro-phenyl)-pyrrolidin-3-yl]-ethanol (X-A-14) and (SR)-1-[(3SR,4RS)-4-(2,4-Dichloro-phenyl)-pyrrolidin-3-yl]-ethanol (X-B-14)

To a solution of 1-[(3SR,4RS)-1-benzyl-4-(2,4-difluoro-phenyl)-pyrrolidin-3-yl]-ethanone (IX-14) (1.87 g, 5.92 mmol) in THF (30 mL) at 0° C. were added portion wise $LiAlH_4$ (0.19 g, 5.21 mol). Stirring was continued for one hour, and the reaction mixture was carefully quenched by addition of aq. $NH_4Cl$, concentrated under vacuo and the product extracted with EtOAC. The combined organic phases were dried on $Na_2SO_4$ and concentrated under vacuo. The two diastereoisomeres were separated by column chromatography ($SiO_2$, EtOAc/H, 1:1) to yield (SR)-1-[(3SR,4RS)-4-(2,4-difluoro-phenyl)-pyrrolidin-3-yl]-ethanol (X-B-14) 0.72 g (38%) as a white solid ES-MS m/e: 318.1 (M+H$^+$) and (RS)-1-[(3SR,4RS)-4-(2,4-difluoro-phenyl)-pyrrolidin-3-yl]-ethanol (X-A-14) 0.374 g (19%) as a white solid ES-MS m/e: 318.1 (M+H$^+$).

d) 2-{(RS)-1-[(3SR,4RS)-1-Benzyl-4-(2,4-difluoro-phenyl)-pyrrolidin-3-yl]-ethoxy}-5-chloro-pyridine (XI-B-14)

To a suspension of $PPh_3$ ($PPh_3$ polymer bound, 3 mmol $PPh_3$/g resin) (1.27 g, 4.85 mmol) in THF (25 mL) at 0° C. were added 5-chloro-pyridin-2-ol (0.429 g, 3.31 mmol) and then DBAD (0.81 g, 3.51 mmol). After 5 minutes was added (SR)-1-[(3SR,4RS)-4-(2,4-difluoro-phenyl)-pyrrolidin-3-yl]-ethanol (X-B-14) (0.70 g, 2.20 mmol). The reaction mixture was stirred over night at RT, filtered on celite and concentrated under vacuo. Extraction with EtOAc/aq.NaOH 1M, followed by column chromatography ($SiO_2$, EtOAc/H, 1:6) yielded 0.69 g (73%) of the title compound as a colorless oil. ES-MS m/e: 429.2 (M+H$^+$).

e) 5-Chloro-2-{(RS)-1-[(3SR,4RS)-4-(2,4-difluoro-phenyl)-pyrrolidin-3-yl]-ethoxy}-pyridine (XII-B-14)

To a solution of 2-{(RS)-1-[(3SR,4RS)-1-benzyl-4-(2,4-difluoro-phenyl)-pyrrolidin-3-yl]-ethoxy}-5-chloro-pyridine 570 mg (1.32 mmol) dissolved in toluene (12 mL) were added 0.43 mL (3.96 mmol) of 1-chloroethyl chloroformate and 0.68 mL (3.96 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography ($SiO_2$, $CH_2Cl_2$/MeOH 9:1) yielded 350 mg (78%) of the title compound as a light yellow oil. ES-MS m/e: 339.1 (M+H$^+$).

Pyrrolidine XII-B-15

2-{(S)-1-[(3R,4S)-4-(4-Chloro-phenyl)-pyrrolidin-3-yl]-ethoxy}-5-trifluoromethyl-pyridine

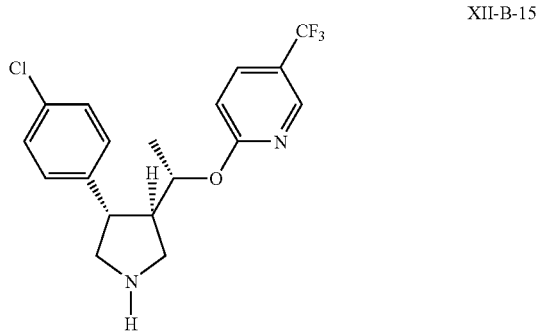

XII-B-15 a) 2-{(S)-1-[(3R,4S)-1-Benzyl-4-(4-chloro-phenyl)-pyrrolidin-3-yl]-ethoxy}-5-trifluoromethyl-pyridine (XI-B-12)

To a stirred solution of 250 mg (0.79 mmol) of (S)-1-[(3R,4S)-1-Benzyl-4-(4-chloro-phenyl)-pyrrolidin-3-yl]-ethanol in DMF (10 mL) was added NaH (57 mg, 1.18 mmol). The reaction mixture was stirred at RT for 30 minutes, and then at 50° C. for 20 minutes. A solution of 2-chloro-5-trifluoromethyl-pyridine (172 mg, 0.95 mmol) in DMF (2 mL) was added dropwise and stirring was continued 3 hours at 50° C. The reaction mixture was concentrated under vacuo. Extraction with EtOAc/$H_2O$, followed by column chromatography ($SiO_2$, EtOAc/H, 1:4) yielded 350 mg (96%) of the title compound as a colorless oil. ES-MS m/e: 461.3 (M+H$^+$).

b) 2-{(S)-1-[(3R,4S)-4-(4-Chloro-phenyl)-pyrrolidin-3-yl]-ethoxy}-5-trifluoromethyl-pyridine (XII-B-15)

To a solution of 6-{(S)-1-[(3R,4S)-1-benzyl-4-(4-chloro-phenyl)-pyrrolidin-3-yl]-ethoxy}-nicotinonitrile 340 mg (0.74 mmol) dissolved in toluene (6 mL) were added 0.24 mL (2.21 mmol) of 1-chloroethyl chloroformate and 0.38 mL (2.21 mmol) of Hunig's base. The reaction mixture was heated at 100° C. for one hour. After cooling down to RT, volatiles were removed under vacuo and the crude was dissolved in MeOH (10 mL). The reaction mixture was heated at 85° C. for 30 minutes and after cooling down to RT, volatiles were removed under vacuo and the residue was directly purified on column chromatography ($SiO_2$, $CH_2Cl_2$/MeOH 9:1) yielded 150 mg (55%) of the title compound as a light yellow oil. ES-MS m/e: 371.2 (M+H$^+$).

Pyrrolidine Intermediates of Formula XV-A and XV-B

Pyrrolidine XV-A-1/XV-B-1

[(3RS,4SR)-3-(3,4-Dichloro-phenyl)-4-((RS)-1-hydroxy-ethyl)-pyrrolidin-1-yl]-(6-methoxy-pyridin-3-yl)-methanone (XV-A-1) and

[(3RS,4SR)-3-(3,4-Dichloro-phenyl)-4-((SR)-1-hydroxy-ethyl)-pyrrolidin-1-yl]-(6-methoxy-pyridin-3-yl)-methanone (XV-B-1)

XV-A-1

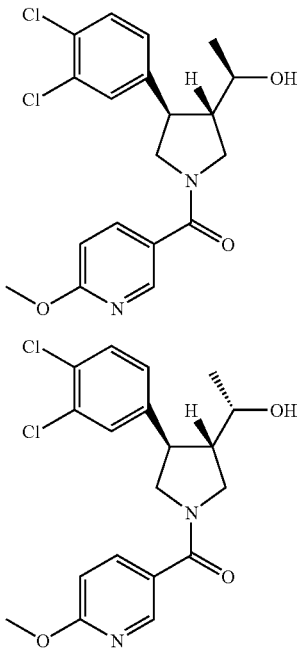

XB-B-1

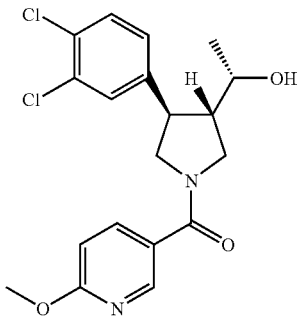

a) 1-[(3SR,4RS)-4-(3,4-Dichloro-phenyl)-pyrrolidin-3-yl]-ethanone (XIII-1)

To a solution of 1-[(3SR,4RS)-1-benzyl-4-(3,4-dichloro-phenyl)-pyrrolidin-3-yl]-ethanone (IX-1) 4.00 g (9.20 mmol) dissolved in CH$_3$CN (50 mL) was added 2.48 mL (18.40 mmol) of 2,2,2-trichloroethyl chloroformate and stirring was continued for 3 hours at RT. Volatiles were removed under vacuo, and the crude residue was dissolved in AcOH (30 mL) before a total of 1.5 g of Zn dust was added portionwise. After three hours at RT, the reaction mixture was filtered on celite, the solvent removed under vacuo, followed by extraction with EtOAc/aq. NaHCO$_3$ (basic pH). The organic phases were dried on Na$_2$SO$_4$ and column chromatography (SiO$_2$, CH$_2$Cl$_2$/MeOH 9:1 to 8:2) yielded 1.50 g (63%) of the title compound as a colorless oil. ES-MS m/e: 258.0 (M+H$^+$).

b) 1-[(3SR,4RS)-4-(3,4-Dichloro-phenyl)-1-(6-methoxy-pyridine-3-carbonyl)-pyrrolidin-3-yl]-ethanone (XIV-1)

To a stirred solution of 6-methoxy-nicotinic acid (0.53 g, 3.40 mmol) in CH$_2$Cl$_2$ (15 mL) were added EDC (0.659 g, 3.40 mmol), HOBt (0.465 g, 3.40 mmol) and Et$_3$N (0.59 mL, 4.3 mmol). After one hour at RT was added 1-[(3SR,4RS)-4-(3,4-dichloro-phenyl)-pyrrolidin-3-yl]-ethanone (XIII-1) (0.74 g, 2.90 mmol) and stirring was continued over night. The reaction mixture was then poured onto water and extracted with CH$_2$Cl$_2$. The combined organic phases were dried over Na$_2$SO$_4$ and concentrate under vacuo. Flash chromatography (SiO$_2$, EtOAc/H, 1:1) afforded 0.64 g (57%) of the title product as a white solid. ES-MS m/e: 393.1 (M+H$^+$).

c) [(3RS,4SR)-3-(3,4-dichloro-phenyl)-4-((RS)-1-hydroxy-ethyl)-pyrrolidin-1-yl]-(6-methoxy-pyridin-3-yl)-methanone (XV-A-1) and [(3RS,4SR)-3-(3,4-dichloro-phenyl)-4-((SR)-1-hydroxy-ethyl)-pyrrolidin-1-yl]-(6-methoxy-pyridin-3-yl)-methanone (XV-B-1)

To a stirred solution of 1-[(3SR,4RS)-4-(3,4-dichloro-phenyl)-1-(6-methoxy-pyridine-3-carbonyl)-pyrrolidin-3-yl]-ethanone (XIV-1) (0.64 g, 1.60 mmol) in MeOH (10 mL) at −78° C. was added LiBH$_4$ (0.047 g, 1.70 mmol). The temperature was slowly raised to RT (over 1 hour), and the reaction mixture was quenched by addition of H$_2$O. The product was extracted with EtOAc, the combined organic phases were dried over Na$_2$SO4. The two diastereoisomers were separated by column chromatography (SiO$_2$) to yield 0.15 g (23%) of [(3RS,4SR)-3-(3,4-dichloro-phenyl)-4-((RS)-1-hydroxy-ethyl)-pyrrolidin-1-yl]-(6-methoxy-pyridin-3-yl)-methanone (XV-A-1) as a white solid ES-MS m/e: 395.3 (M+H$^+$) and 0.48 g (75%) of [(3RS,4SR)-3-(3,4-dichloro-phenyl)-4-((SR)-1-hydroxy-ethyl)-pyrrolidin-1-yl]-(6-methoxy-pyridin-3-yl)-methanone (XV-B-1) as a white solid ES-MS m/e: 395.3 (M+H$^+$).

EXAMPLE 1

4-[(3SR,4RS)-3-(4-Chloro-phenoxymethyl)-4-(3,4-dichloro-phenyl)-pyrrolidine-1-carbonyl]-benzonitrile

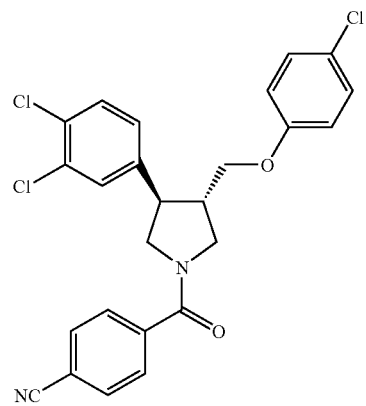

a) (3SR,4RS)-1-Benzyl-4-(3,4-dichloro-phenyl)-pyrrolidine-3-carboxylic acid ethyl ester A solution of N-(methoxymethyl)-N-(phenylmethyl)-N-(trimethylsilyl)methylamine (2.46 g, 10.4 mmol) in CH$_2$Cl$_2$ (15 mL) was added dropwise, over a 30 minutes period, to a stirred solution of (E)-3-(3,4-dichloro-phenyl)-acrylic acid ethyl ester (2.40 g, 10.4 mmol) and trifluoroacetic acid (0.08 mL, 1 mmol) in CH$_2$Cl$_2$ (10 mL) at 0° C. The ice bath was removed, and the solution was stirred at 25° C. for an additional 48 h. It was then concentrated and purification by flash chromatography (SiO$_2$, EtOAc/H 1:4) afforded 2.48 g (66%) of the title compound as a yellow oil. ES-MS m/e: 379.3 (M+H$^+$).

b) [(3SR,4RS)-1-Benzyl-4-(3,4-dichloro-phenyl)-pyrrolidin-3-yl]-methanol

To a solution of (3SR,4RS)-1-benzyl-4-(3,4-dichloro-phenyl)-pyrrolidine-3-carboxylic acid ethyl ester (1.00 g, 2.64 mmol) in THF (15 mL) at 0° C. were added portion wise LiAlH$_4$ (211 mg, 5.56 mmol). Stirring was continued for 2 hours, and the reaction mixture was quenched by addition of aq. NH$_4$Cl, concentrated under vacuo and the product extracted with EtOAC. The combined organic phases were dried on Na$_2$SO$_4$ and concentrated under vacuo. Flash chromatography (SiO$_2$, EtOAc) to yield 0.70 g (79%) of the title product as a white solid ES-MS m/e: 336.3 (M+H$^+$).

c) (3SR,4RS)-1-Benzyl-3-(4-chloro-phenoxymethyl)-4-(3,4-dichloro-phenyl)-pyrrolidine Using the standard procedure for a Mitsunobu reaction (general procedure III), the coupling between [(3SR,4RS)-1-benzyl-4-(3,4-dichloro-phenyl)-pyrrolidin-3-yl]-methanol (700 mg, 2.08 mmol) and 4-chloro-phenol (294 mg, 2.28 mmol) yielded the title product (360 mg, 39%) as a colorless oil. ES-MS m/e: 446.1 (M+H$^+$).

d) (3SR,4RS)-3-(4-Chloro-phenoxymethyl)-4-(3,4-dichloro-phenyl)-pyrrolidine

To a solution of (3SR,4RS)-1-benzyl-3-(4-chloro-phenoxymethyl)-4-(3,4-dichloro-phenyl)-pyrrolidine 350 mg (0.78 mmol) dissolved in CH$_3$CN (8 mL) was added 0.12 mL (0.86 mmol) of 2,2,2-trichloroethyl chloroformate and stirring was continued for 2 hours at RT. Volatiles were removed under vacuo, and the crude residue was dissolved in AcOH (5 mL) before a total of 200 mg of Zn dust was added portion wise. After three hours at RT, the reaction mixture was filtered on celite, the solvent removed under vacuo, followed by an extraction with EtOAc/aq. NaHCO$_3$ (basic pH). The organic phases were dried on Na$_2$SO$_4$ and column chromatography (SiO$_2$, CH$_2$Cl$_2$/MeOH 9:1 to 8:2) yielded 210 mg (75%) of the title compound as a colorless oil. ES-MS m/e: 357.1 (M+H$^+$).

e) 4-[(3SR,4RS)-3-(4-Chloro-phenoxymethyl)-4-(3,4-dichloro-phenyl)-pyrrolidine-1-carbonyl]-benzonitrile Using the general procedure II, the coupling between (3SR,4RS)-3-(4-chloro-phenoxymethyl)-4-(3,4-dichloro-phenyl)-pyrrolidine (105 mg, 0.29 mmol) and 4-cyano-benzoyl chloride (58 mg, 0.35 mmol) afforded 55 mg (39%) of the title compound as a white solid. ES-MS m/e: 486.9 (M+H$^+$).

EXAMPLE 2

4-{(3RS,4SR)-3-(3,4-Dichloro-phenyl)-4-[(RS)-1-(4-trifluoromethyl-phenoxy)-ethyl]-pyrrolidine-1-carbonyl}-benzonitrile

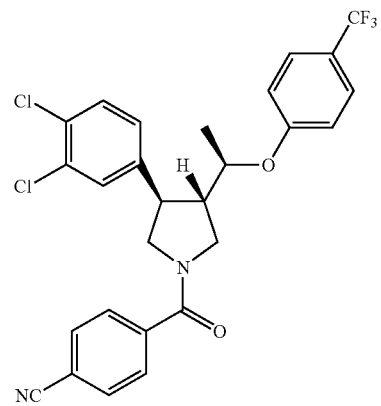

Coupling according to general procedure II:

Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1), Acid chloride: 4-Cyano-benzoyl chloride (commercially available), ES-MS m/e: 534.6 (M+H$^+$).

EXAMPLE 3

{(3RS,4SR)-3-(3,4-Dichloro-phenyl)-4-[(RS)-1-(4-trifluoromethyl-phenoxy)-ethyl]-pyrrolidin-1-yl}-pyridin-3-yl-methanone

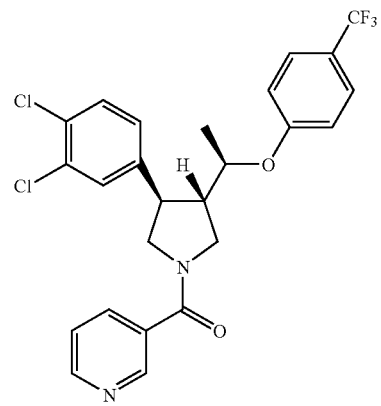

Coupling according to general procedure I:

Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1), Carboxylic acid: Nicotinic acid (commercially available), ES-MS m/e: 509.0 (M+H$^+$).

EXAMPLE 4

{(3RS,4SR)-3-(3,4-Dichloro-phenyl)-4-[(RS)-1-(4-trifluoromethyl-phenoxy)-ethyl]-pyrrolidin-1-yl}-pyridin-4-yl-methanone

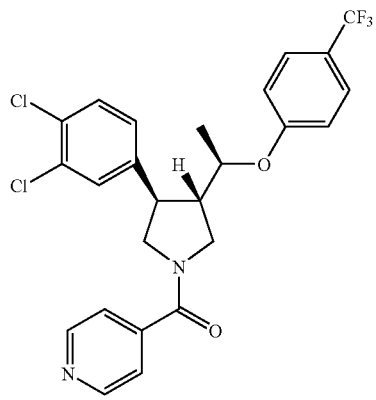

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: Isonicotinic acid (commercially available),
ES-MS m/e: 509.0 (M+H$^+$).

EXAMPLE 5

{(3RS,4SR)-3-(3,4-Dichloro-phenyl)-4-[(RS)-1-(4-trifluoromethyl-phenoxy)-ethyl]-pyrrolidin-1-yl}-(2-methoxy-pyrimidin-5-yl)-methanone

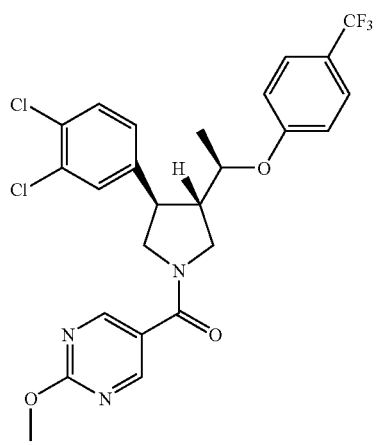

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: 2-Methoxy-pyrimidine-5-carboxylic acid (commercially available),
ES-MS m/e: 540.2 (M+H$^+$).

EXAMPLE 6

{(3RS,4SR)-3-(3,4-Dichloro-phenyl)-4-[(RS)-1-(4-trifluoromethyl-phenoxy)-ethyl]-pyrrolidin-1-yl}-(6-methyl-pyridin-3-yl)-methanone

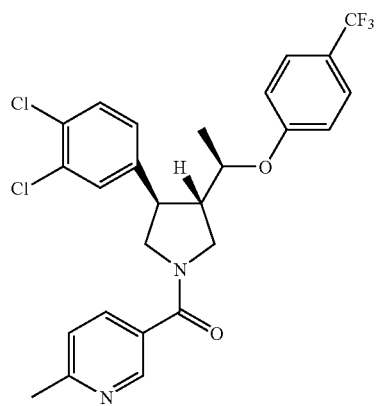

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: 6-Methyl-nicotinic acid (commercially available),
ES-MS m/e: 523.0 (M+H$^+$).

EXAMPLE 7

{(3RS,4SR)-3-(3,4-Dichloro-phenyl)-4-[(RS)-1-(4-trifluoromethyl-phenoxy)-ethyl]-pyrrolidin-1-yl}-(6-fluoro-pyridin-3-yl)-methanone

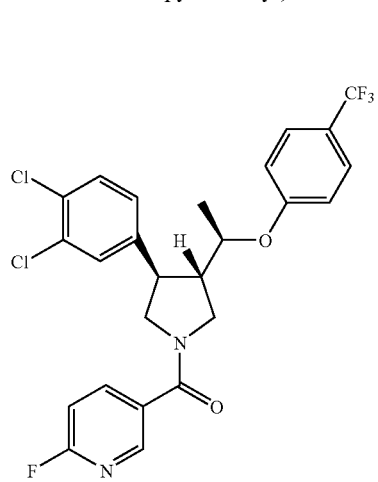

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: 6-Fluoro-nicotinic acid (commercially available),
ES-MS m/e: 527.1 (M+H$^+$).

EXAMPLE 8

{(3RS,4SR)-3-(3,4-Dichloro-phenyl)-4-[(RS)-1-(4-trifluoromethyl-phenoxy)-ethyl]-pyrrolidin-1-yl}-(2-methoxy-pyridin-4-yl)-methanone

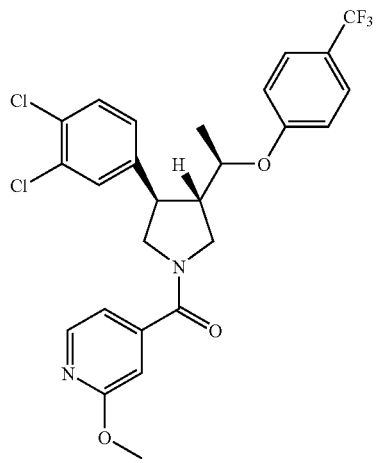

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: 2-Methoxy-isonicotinic acid (commercially available),
ES-MS m/e: 539.2 (M+H$^+$).

EXAMPLE 9

{(3RS,4SR)-3-(3,4-Dichloro-phenyl)-4-[(RS)-1-(4-trifluoromethyl-phenoxy)-ethyl]-pyrrolidin-1-yl}-(6-methoxy-pyridin-3-yl)-methanone

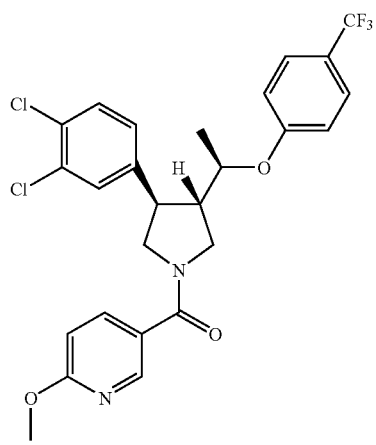

Coupling according to general procedure I:
Pyrrolidine intermediate: (3RS,4SR)-3-(3,4-Dichloro-phenyl)-4-[(RS)-1-(4-trifluoromethyl-phenoxy)-ethyl]-pyrrolidine (XII-B-1),
Carboxylic acid: 6-Methoxy-nicotinic acid (commercially available),
ES-MS m/e: 539.3 (M+H$^+$).

EXAMPLE 10

4-[(3SR,4RS)-3-[(RS)-1-(5-Chloro-pyridin-2-yloxy)-ethyl]-4-(3,4-dichloro-phenyl)-pyrrolidine-1-carbonyl]-benzonitrile

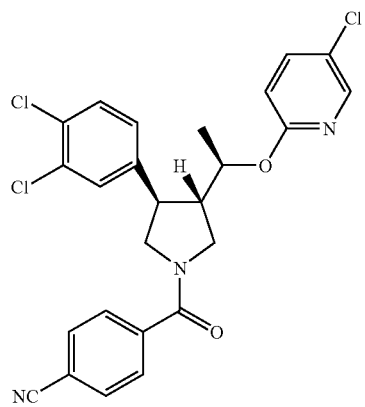

Coupling according to general procedure II:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Acid chlorid: 4-Cyano-benzoyl chloride (commercially available),
ES-MS m/e: 502.2 (M+H$^+$).

EXAMPLE 11

[(3SR,4RS)-3-[(RS)-1-(5-Chloro-pyridin-2-yloxy)-ethyl]-4-(3,4-dichloro-phenyl)-pyrrolidin-1-yl]-(6-methoxy-pyridin-3-yl)-methanone

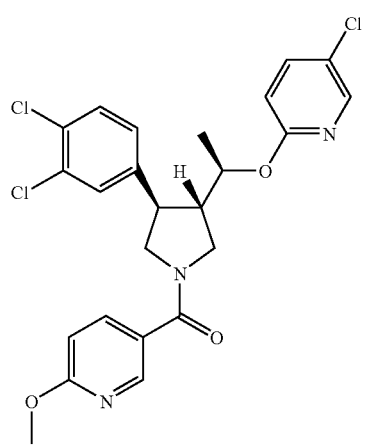

Coupling according to general procedure II:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Acid chlorid: 6-Methoxy-nicotinic acid (commercially available),
ES-MS m/e: 508.1 (M+H⁺).

EXAMPLE 12

[(3SR,4RS)-3-[(RS)-1-(5-Chloro-pyridin-2-yloxy)-ethyl]-4-(3,4-dichloro-phenyl)-pyrrolidin-1-yl]-(2-methoxy-pyrimidin-5-yl)-methanone

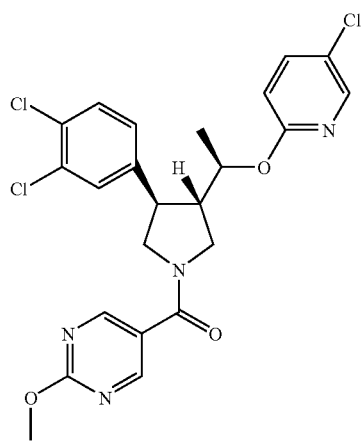

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2-Methoxy-pyrimidine-5-carboxylic acid (commercially available),
ES-MS m/e: 509.1 (M+H⁺).

EXAMPLE 13

[(3SR,4RS)-3-[(RS)-1-(5-Chloro-pyridin-2-yloxy)-ethyl]-4-(3,4-dichloro-phenyl)-pyrrolidin-1-yl]-(4-dimethylamino-phenyl)-methanone

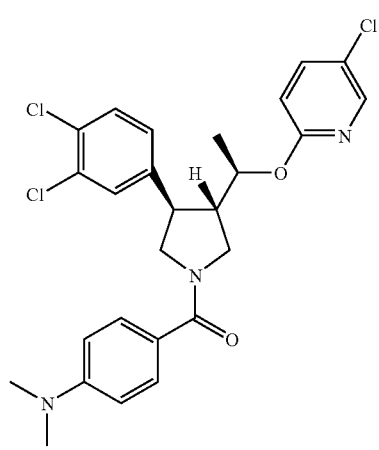

Coupling according to general procedure II:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Acid chlorid: 4-Dimethylamino-benzoyl chloride (commercially available),
ES-MS m/e: 519.8 (M+H⁺).

EXAMPLE 14

[(3SR,4RS)-3-[(RS)-1-(5-Chloro-pyridin-2-yloxy)-ethyl]-4-(3,4-dichloro-phenyl)-pyrrolidin-1-yl]-(6-fluoro-pyridin-3-yl)-methanone

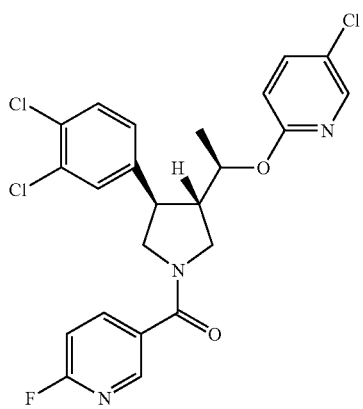

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 6-Fluoro-nicotinic acid (commercially available),
ES-MS m/e: 495.9 (M+H⁺).

EXAMPLE 15

[(3SR,4RS)-3-[(RS)-1-(5-Chloro-pyridin-2-yloxy)-ethyl]-4-(3,4-dichloro-phenyl)-pyrrolidin-1-yl]-(2-methyl-pyridin-4-yl)-methanone

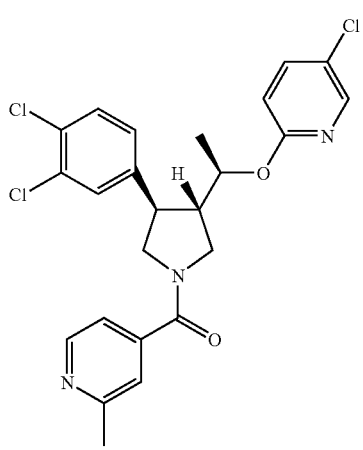

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 2-Methyl-isonicotinic acid (commercially available),
ES-MS m/e: 491.9 (M+H⁺).

EXAMPLE 16

[(3SR,4RS)-3-[(RS)-1-(5-Chloro-pyridin-2-yloxy)-ethyl]-4-(3,4-dichloro-phenyl)-pyrrolidin-1-yl]-(6-methyl-pyridin-3-yl)-methanone

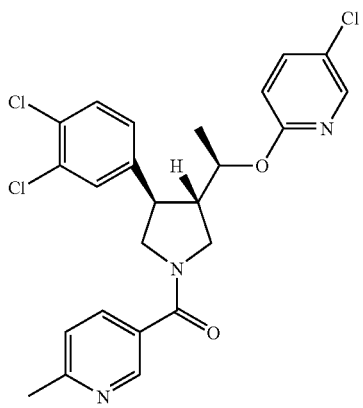

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 6-Methyl-nicotinic acid (commercially available),
ES-MS m/e: 491.9 (M+H⁺).

EXAMPLE 17

[(3SR,4RS)-3-[(RS)-1-(5-Chloro-pyridin-2-yloxy)-ethyl]-4-(3,4-dichloro-phenyl)-pyrrolidin-1-yl]-(2-methyl-pyrimidin-5-yl)-methanone

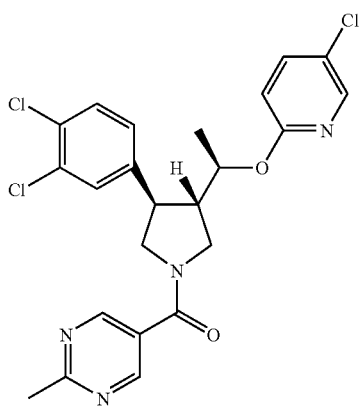

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2-Methyl-pyrimidine-5-carboxylic acid (commercially available),
ES-MS m/e: 492.8 (M+H⁺).

EXAMPLE 18

[(3SR,4RS)-3-[(RS)-1-(5-Chloro-pyridin-2-yloxy)-ethyl]-4-(3,4-dichloro-phenyl)-pyrrolidin-1-yl]-(2-methoxy-pyridin-4-yl)-methanone

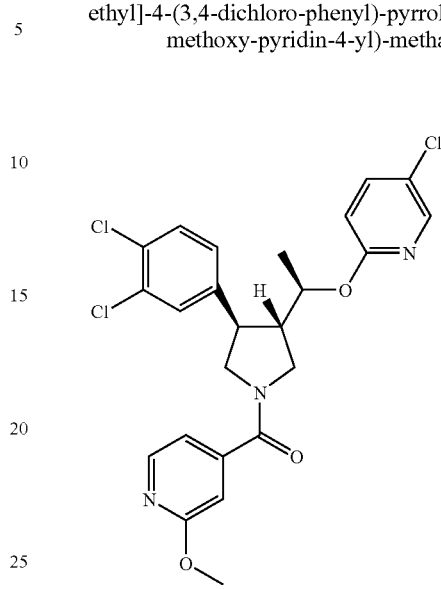

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2-Methoxy-isonicotinic acid (commercially available),
ES-MS m/e: 507.8 (M+H⁺).

EXAMPLE 19

[(3SR,4RS)-3-[(RS)-1-(5-Chloro-pyridin-2-yloxy)-ethyl]-4-(3,4-dichloro-phenyl)-pyrrolidin-1-yl]-(6-dimethylamino-pyridin-3-yl)-methanone

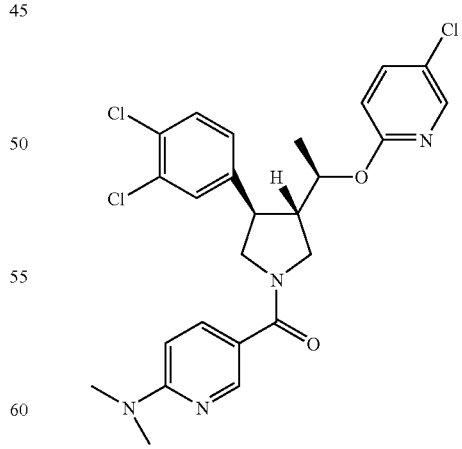

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 6-Dimethylamino-nicotinic acid (commercially available), ES-MS m/e: 519.2 (M+H$^+$).

EXAMPLE 20

(6-Amino-pyridin-3-yl)-[(3SR,4RS)-3-[(RS)-1-(5-chloro-pyridin-2-yloxy)-ethyl]-4-(3,4-dichloro-phenyl)-pyrrolidin-1-yl]-mthanone

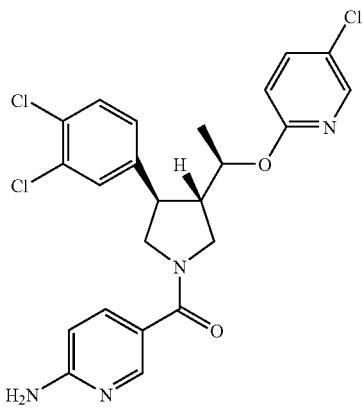

Coupling according to general procedure I:

Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 6-Amino-nicotinic acid (commercially available), ES-MS m/e: 493.2 (M+H$^+$).

EXAMPLE 21

[(3S,4R)-3-[(R)-1-(5-Chloro-pyridin-2-yloxy)-ethyl]-4-(3,4-dichloro-phenyl)-pyrrolidin-1-yl]-(6-methoxy-pyridin-3-yl)-methanone and

[(3R,4S)-3-[(S)-1-(5-Chloro-pyridin-2-yloxy)-ethyl]-4-(3,4-dichloro-phenyl)-pyrrolidin-1-yl]-(6-methoxy-pyridin-3-yl)-methanone The racemic mixture consisting of [(3S,4R)-3-[(R)-1-(5-Chloro-pyridin-2-yloxy)-ethyl]-4-(3,4-dichloro-phenyl)-pyrrolidin-1-yl]-(6-methoxy-pyridin-3-yl)-methanone and [(3R,4S)-3-[(S)-1-(5-Chloro-pyridin-2-yloxy)-ethyl]-4-(3,4-dichloro-phenyl)-pyrrolidin-1-yl]-(6-methoxy-pyridin-3-yl)-methanone were resolved by chiral preparative HPLC to give both enantiomers optically pure. ES-MS m/e: 508.1 (M+H$^+$).

EXAMPLE 22

{(3RS,4SR)-3-(3,4-Dichloro-phenyl)-4-[(SR)-1-(5-fluoro-pyrimidin-2-yloxy)-ethyl]-pyrrolidin-1-yl}-(6-methoxy-pyridin-3-yl)-methanone

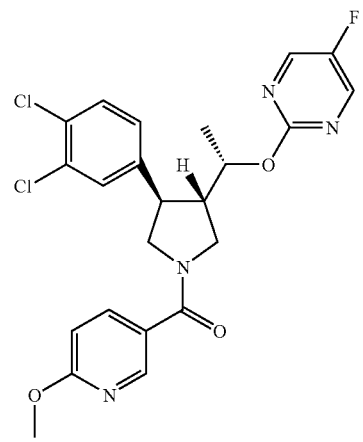

Mitsunobu reaction according to general procedure III:

Pyrrolidine intermediate: [(3RS,4SR)-3-(3,4-Dichloro-phenyl)-4-( (RS)-1-hydroxy-ethyl)-pyrrolidin-1-yl]-(6-methoxy-pyridin-3-yl)-methanone (XV-A-1), Pyrimidin-ol: 5-Fluoro-pyrimidin-2-ol (commercially available), ES-MS m/e: 490.9 (M+H$^+$).

EXAMPLE 23

{(3RS,4SR)-3-(3,4-Dichloro-phenyl)-4-[(SR)-1-(5-fluoro-pyridin-2-yloxy)-ethyl]-pyrrolidin-1-yl}-(6-methoxy-pyridin-3-yl)-methanone

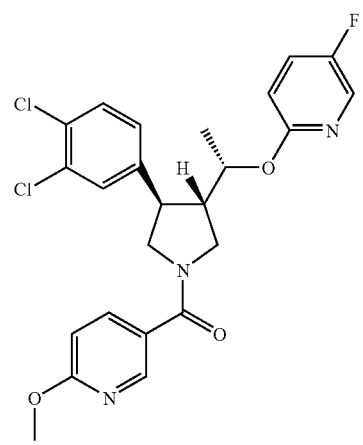

Mitsunobu reaction according to general procedure III:

Pyrrolidine intermediate: [(3RS,4SR)-3-(3,4-Dichloro-phenyl)-4-( (RS)-1-hydroxy-ethyl)-pyrrolidin-1-yl]-(6-methoxy-pyridin-3-yl)-methanone (XV-A-1), Pyridin-ol: 5-Fluoro-pyridin-2-ol (commercially available),
ES-MS m/e: 490.0 (M+H⁺).

EXAMPLE 24

{(3RS,4SR)-3-(3,4-Dichloro-phenyl)-4-[(SR)-1-(5-methyl-pyridin-2-yloxy)-ethyl]-pyrrolidin-1-yl}-(6-methoxy-pyridin-3-yl)-methanone

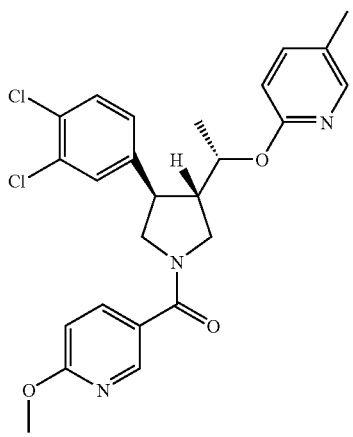

Mitsunobu reaction according to general procedure III:
Pyrrolidine intermediate: [(3RS,4SR)-3-(3,4-Dichloro-phenyl)-4-( (RS)-1-hydroxy-ethyl)-pyrrolidin-1-yl]-(6-methoxy-pyridin-3-yl)-methanone (XV-A-1),
Pyridin-ol: 5-Methyl-pyridin-2-ol (commercially available),
ES-MS m/e: 486.0 (M+H⁺).

EXAMPLE 25

{(3RS,4SR)-3-(3,4-Dichloro-phenyl)-4-[(RS)-1-(5-fluoro-pyrimidin-2-yloxy)-ethyl]-pyrrolidin-1-yl}-(6-methoxy-pyridin-3-yl)-methanone

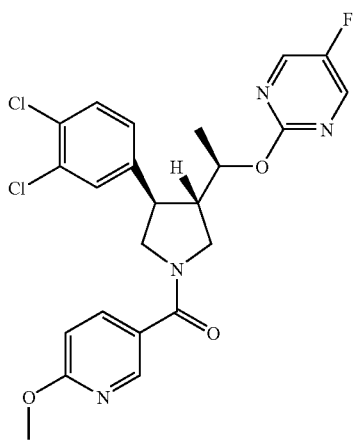

Mitsunobu reaction according to general procedure III:
Pyrrolidine intermediate: [(3RS,4SR)-3-(3,4-Dichloro-phenyl)-4-((SR)-1-hydroxy-ethyl)-pyrrolidin-1-yl]-(6-methoxy-pyridin-3-yl)-methanone (XV-B-1),
Pyrimidin-ol: 5-Fluoro-pyrimidin-2-ol (commercially available),
ES-MS m/e: 491.0 (M+H⁺).

EXAMPLE 26

{(3RS,4SR)-3-(3,4-Dichloro-phenyl)-4-[(RS)-1-(5-fluoro-pyridin-2-yloxy)-ethyl]-pyrrolidin-1-yl}-(6-methoxy-pyridin-3-yl)-methanone

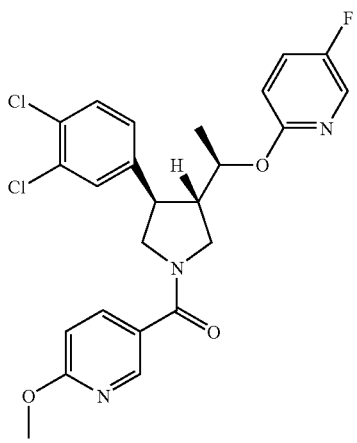

Mitsunobu reaction according to general procedure III:
Pyrrolidine intermediate: [(3RS,4SR)-3-(3,4-Dichloro-phenyl)-4-((SR)-1-hydroxy-ethyl)-pyrrolidin-1-yl]-(6-methoxy-pyridin-3-yl)-methanone (XV-B-1),
Pyridin-ol: 5-Fluoro-pyridin-2-ol (commercially available),
ES-MS m/e: 490.9 (M+H⁺).

EXAMPLE 27

[(3SR,4RS)-3-[(RS)-1-(5-Chloro-pyridin-2-yloxy)-ethyl]-4-(3,4-dichloro-phenyl)-pyrrolidin-1-yl]-(5-chloro-thiophen-2-yl)-methanone

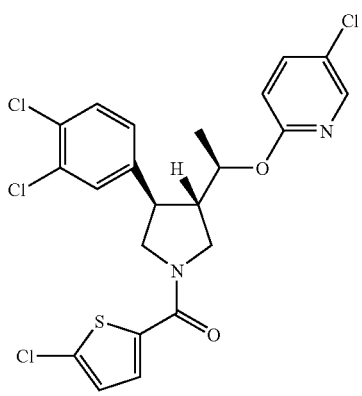

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 5-Chloro-thiophene-2-carboxylic acid (commercially available),
ES-MS m/e: 516.7 (M+H⁺).

EXAMPLE 28

[(3SR,4RS)-3-[(RS)-1-(5-Chloro-pyridin-2-yloxy)-ethyl]-4-(3,4-dichloro-phenyl)-pyrrolidin-1-yl]-(2,5-dimethyl-furan-3-yl)-methanone

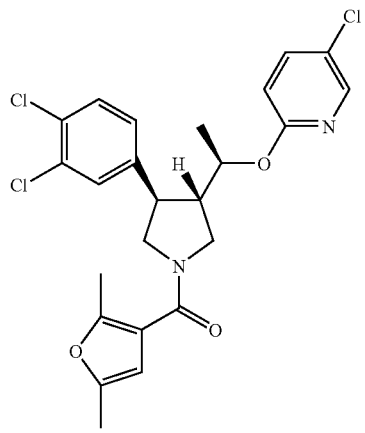

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2,5-Dimethyl-furan-3-carboxylic acid (commercially available),
ES-MS m/e: 492.9 (M+H$^+$).

EXAMPLE 29

[(3SR,4RS)-3-[(RS)-1-(5-Chloro-pyridin-2-yloxy)-ethyl]-4-(3,4-dichloro-phenyl)-pyrrolidin-1-yl]-isoxazol-5-yl-methanone

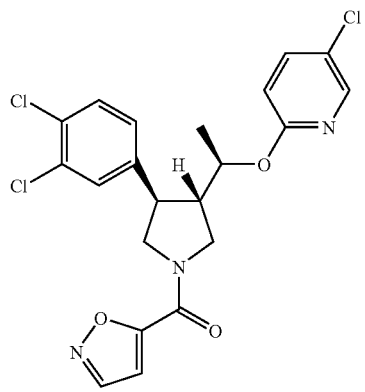

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: Isoxazole-5-carboxylic acid (commercially available),
ES-MS m/e: 468.2 (M+H$^+$).

EXAMPLE 30

{5-[(3SR,4RS)-3-[(RS)-1-(5-Chloro-pyridin-2-yloxy)-ethyl]-4-(3,4-dichloro-phenyl)-pyrrolidine-1-carbonyl]-furan-2-yl}-acetonitrile

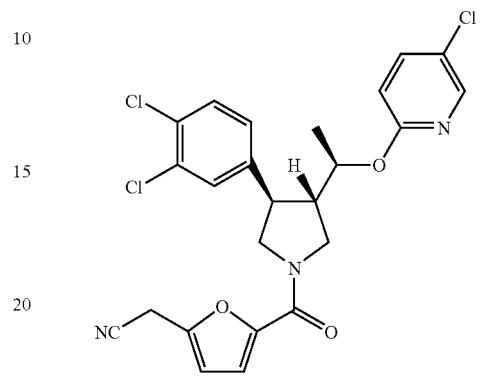

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 5-Cyanomethyl-furan-2-carboxylic acid (commercially available),
ES-MS m/e: 505.9 (M+H$^+$).

EXAMPLE 31

[(3SR,4RS)-3-[(RS)-1-(5-Chloro-pyridin-2-yloxy)-ethyl]-4-(3,4-dichloro-phenyl)-pyrrolidin-1-yl]-(1-cyclopropyl-2,5-dimethyl-1H-pyrrol-3-yl)-methanone

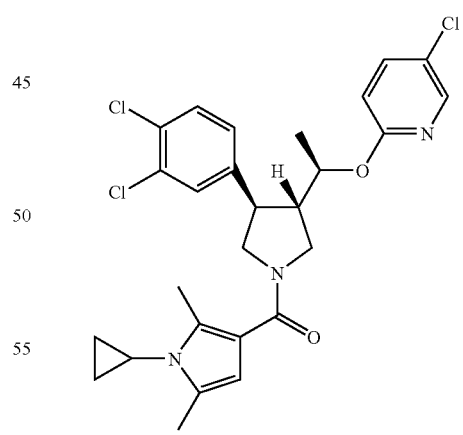

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 1-Cyclopropyl-2,5-dimethyl-1H-pyrrole-3-carboxylic acid (commercially available),
ES-MS m/e: 533.8 (M+H$^+$).

EXAMPLE 32

[(3SR,4RS)-3-[(RS)-1-(5-Chloro-pyridin-2-yloxy)-ethyl]-4-(3,4-dichloro-phenyl)-pyrrolidin-1-yl]-(5-methoxy-thiophen-2-yl)-methanone

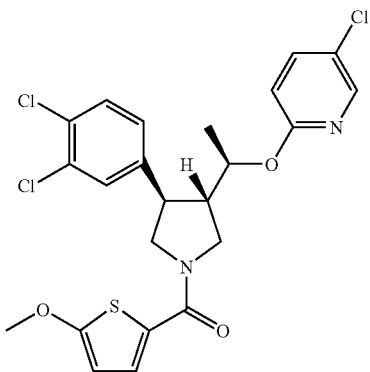

Coupling according to general procedure I:

Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 5-Methoxy-thiophene-2-carboxylic acid (commercially available), ES-MS m/e: 510.9 (M+H$^+$).

EXAMPLE 33

[(3SR,4RS)-3-[(RS)-1-(5-Chloro-pyridin-2-yloxy)-ethyl]-4-(3,4-dichloro-phenyl)-pyrrolidin-1-yl]-(2-chloro-thiazol-5-yl)-methanone

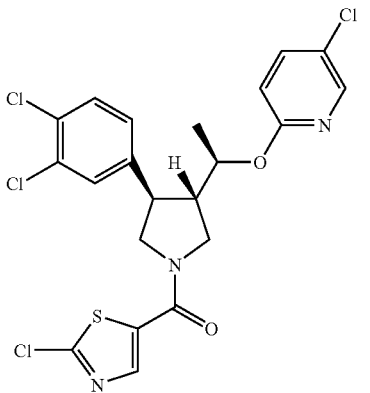

Coupling according to general procedure I:

Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 2-Chloro-thiazole-5-carboxylic acid (commercially available), ES-MS m/e: 517.8 (M+H$^+$).

EXAMPLE 34

6-{(RS)-1-[(3SR,4RS)-4-(3,4-Dichloro-phenyl)-1-(6-methoxy-pyridine-3-carbonyl)-pyrrolidin-3-yl]-ethoxy}-nicotinonitrile

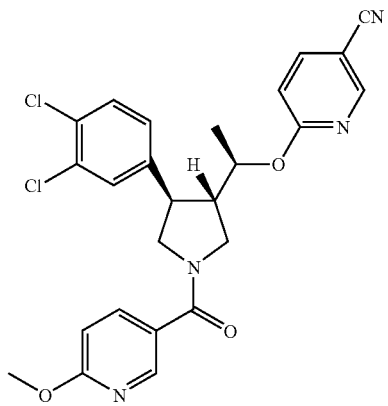

Mitsunobu reaction according to general procedure III:

Pyrrolidine intermediate: [(3RS,4SR)-3-(3,4-Dichloro-phenyl)-4-((SR)-1-hydroxy-ethyl)-pyrrolidin-1-yl]-(6-methoxy-pyridin-3-yl)-methanone (XV-B-1), Pyridin-ol: 6-Hydroxy-nicotinonitrile (commercially available), ES-MS m/e: 497.0 (M+H$^+$).

EXAMPLE 35

5-[(3SR,4RS)-3-[(RS)-1-(5-Chloro-pyridin-2-yloxy)-ethyl]-4-(3,4-dichloro-phenyl)-pyrrolidine-1-carbonyl]-pyridine-2-carbonitrile

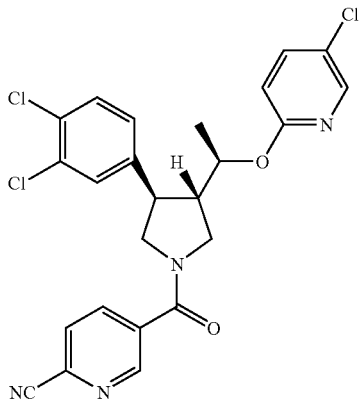

Coupling according to general procedure I:

Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 6-Cyano-nicotinic acid (commercially available), ES-MS m/e: 503.1 (M+H$^+$).

EXAMPLE 36

6-{(SR)-1-[(3RS,4SR)-4-(3,4-Dichloro-phenyl)-1-(2,4-dimethyl-pyrimidine-5-carbonyl)-pyrrolidin-3-yl]-ethoxy}-nicotinonitrile

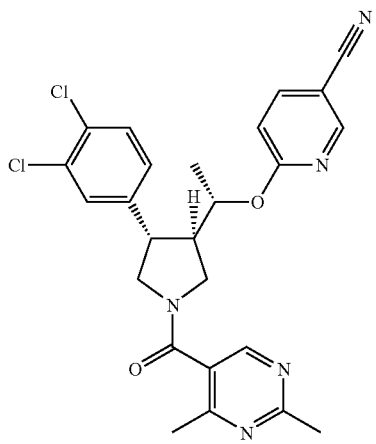

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 2,4-Dimethyl-pyrimidine-5-carboxylic acid (commercially available),
ES-MS m/e: 496.3 (M+H$^+$).

EXAMPLE 37

[(3SR,4RS)-3-[(RS)-1-(5-Chloro-pyridin-2-yloxy)-ethyl]-4-(3,4-dichloro-phenyl)-pyrrolidin-1-yl]-(2,4-dimethyl-pyrimidin-5-yl)-methanone

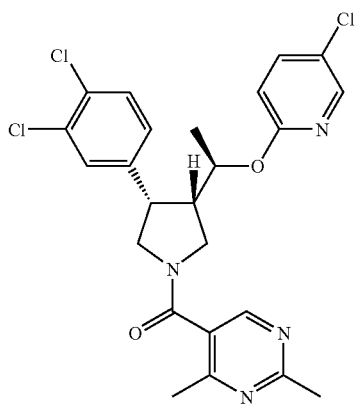

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2,4-Dimethyl-pyrimidine-5-carboxylic acid (commercially available),
ES-MS m/e: 507.2 (M+H$^+$).

EXAMPLE 38

N-{5-[(3SR,4RS)-3-[(RS)-1-(5-Chloro-pyridin-2-yloxy)-ethyl]-4-(3,4-dichloro-phenyl)-pyrrolidine-1-carbonyl]-pyridin-2-yl}-acetamide

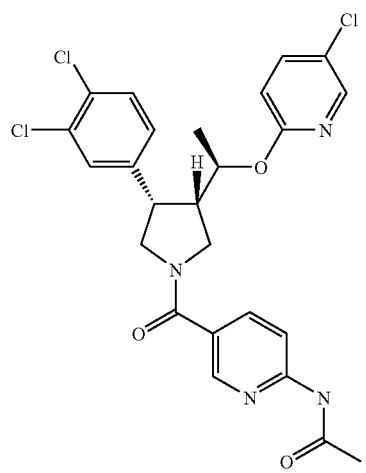

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 6-Acetylamino-nicotinic acid (commercially available),
ES-MS m/e: 354.1 (M+H$^+$).

EXAMPLE 39

[(3SR,4RS)-3-[(RS)-1-(5-Chloro-pyridin-2-yloxy)-ethyl]-4-(3,4-dichloro-phenyl)-pyrrolidin-1-yl]-(6-dimethylaminomethyl-pyridin-3-yl)-methanone

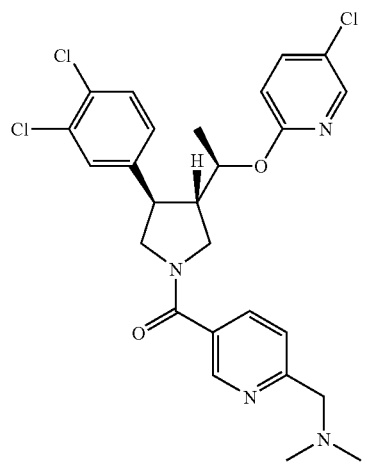

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 6-Dimethylaminomethyl-nicotinic acid (described herein after),
ES-MS m/e: 535.1 (M+H⁺).

6-Dimethylaminomethyl-nicotinic acid

1ˢᵗ step: To a stirred suspension of 6-methylnicotinic acid (commercially available) (500 mg, 3.64 mmol) in THF (14 mL) at RT, was added 1,3-dibromo-5,5-dimethylhydantoin (DDH) (1.06 g, 3.71 mmol). Stirring was continued over night and concentrated under vacuo. Column chromatography (SiO₂, CH₂Cl₂/MeOH: 8/2) yielded 410 mg (52%) of 6-bromomethyl-nicotinic acid as a light orange solid. ES-MS m/e: 214.2-216.3 (M+H⁺).

2ⁿᵈ step: To a stirred solution of 6-bromomethyl-nicotinic acid (350 mg, 1.62 mmol) in EtOH (3 mL) was added a solution of dimethyl-amine in EtOH (2 mL, 30% solution). Stirring was continued for 1 hour, concentrated under vacuo. Column chromatography (SiO₂, CH₂Cl₂/MeOH: 8/2, aq. NH₃ 1%) yielded 205 mg (70%) of 6-dimethylaminomethyl-nicotinic acid as a light brown solid. ES-MS m/e: 181.1 (M+H⁺).

EXAMPLES 40 & 41

[(3R,4S)-3-[(S)-1-(5-Chloro-pyridin-2-yloxy)-ethyl]-4-(3,4-dichloro-phenyl)-pyrrolidin-1-yl]-(2-methyl-pyrimidin-5-yl)-methanone and

[(3S,4R)-3-[(R)-1-(5-Chloro-pyridin-2-yloxy)-ethyl]-4-(3,4-dichloro-phenyl)-pyrrolidin-1-yl]-(2-methyl-pyrimidin-5-yl)-methanone

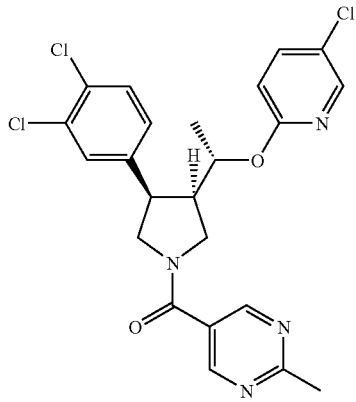

The two optically pure enantiomeres were obtained with a preparative chiral HPLC separation of the racemic mixture prepared from:

Coupling according to general procedure I:
Pyrrolidine intermediate: 5-Chloro-2-{(RS)-1-[(3SR, 4RS)-4-(3,4-dichloro-phenyl)-pyrrolidin-3-yl]-ethoxy}-pyridine (XII-B-2), Carboxylic acid: 2-Methyl-pyrimidine-5-carboxylic acid (commercially available),
ES-MS m/e: 492.8 (M+H⁺). Same MS spectra for both enantiomers.

EXAMPLE 42

[(3SR,4RS)-3-[(RS)-1-(5-Chloro-pyridin-2-yloxy)-ethyl]-4-(3,4-dichloro-phenyl)-pyrrolidin-1-yl]-(4-dimethylaminomethyl-phenyl)-methanone

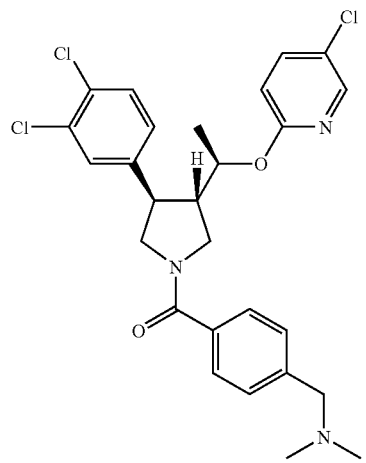

Coupling according to general procedure I:
Pyrrolidine intermediate: 5-Chloro-2-{(RS)-1-[(3SR, 4RS)-4-(3,4-dichloro-phenyl)-pyrrolidin-3-yl]-ethoxy}-pyridine (XII-B-2),
Carboxylic acid: 4-Dimethylaminomethyl-benzoic acid (commercially available),
ES-MS m/e: 533.8 (M+H⁺).

EXAMPLE 43

6-{(SR)-1-[(3RS,4SR)-4-(3,4-Dichloro-phenyl)-1-(6-dimethylaminomethyl-pyridine-3-carbonyl)-pyrrolidin-3-yl]-ethoxy}-nicotinonitrile

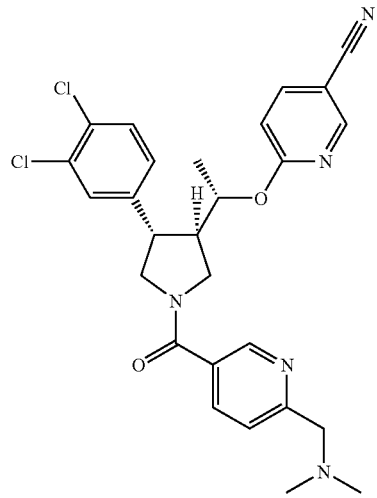

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Dimethylaminomethyl-nicotinic acid (described herein above),
ES-MS m/e: 525.5 (M+H$^+$).

EXAMPLE 44

[(3S,4R)-3-[(R)-1-(5-Chloro-pyridin-2-yloxy)-ethyl]-4-(3,4-dichloro-phenyl)-pyrrolidin-1-yl]-[4-(2-dimethylamino-ethyl)-phenyl]-methanone

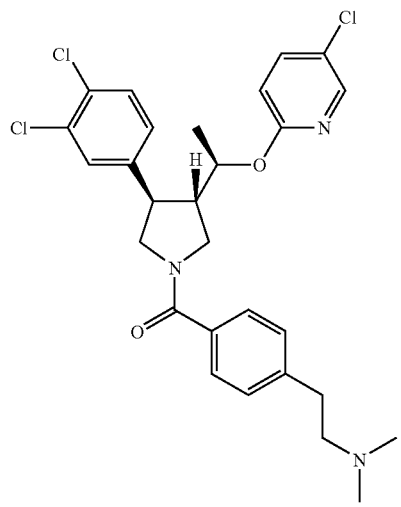

Coupling according to general procedure I:
Pyrrolidine intermediate: 5-Chloro-2-{(RS)-1-[(3SR, 4RS)-4-(3,4-dichloro-phenyl)-pyrrolidin-3-yl]-ethoxy}-pyridine (XII-B-2),
Carboxylic acid: 4-(2-Dimethylamino-ethyl)-benzoic acid (described in EP 529858 A1),
ES-MS m/e: 547.8 (M+H$^+$).

EXAMPLE 45

[(3SR,4RS)-3-[(RS)-1-(5-Chloro-pyridin-2-yloxy)-ethyl]-4-(3,4-dichloro-phenyl)-pyrrolidin-1-yl]-(6-methylsulfanyl-pyridin-3-yl)-methanone

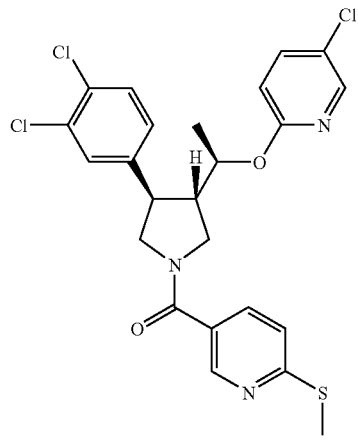

Coupling according to general procedure I:
Pyrrolidine intermediate: 5-Chloro-2-{(RS)-1-[(3SR, 4RS)-4-(3,4-dichloro-phenyl)-pyrrolidin-3-yl]-ethoxy}-pyridine (XII-B-2),
Carboxylic acid: 6-Methylsulfanyl-nicotinic acid (commercially available),
ES-MS m/e: 523.1 (M+H$^+$).

EXAMPLE 46

[(3SR,4RS)-3-[(RS)-1-(5-Chloro-pyridin-2-yloxy)-ethyl]-4-(3,4-dichloro-phenyl)-pyrrolidin-1-yl]-[6-(2-pyrrolidin-1-yl-ethyl)-pyridin-3-yl]-methanone

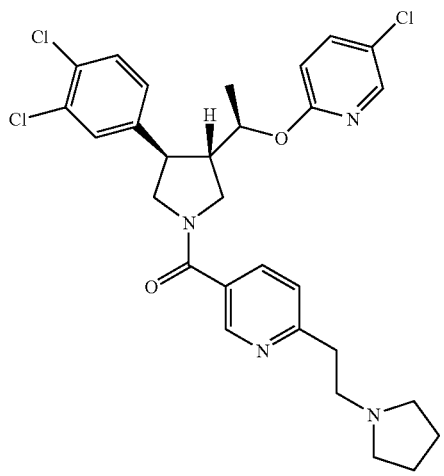

Coupling according to general procedure I:
Pyrrolidine intermediate: 5-Chloro-2-{(RS)-1-[(3SR, 4RS)-4-(3,4-dichloro-phenyl)-pyrrolidin-3-yl]-ethoxy}-pyridine (XII-B-2),
Carboxylic acid: 6-(2-Pyrrolidin-1-yl-ethyl)-nicotinic acid (commercially available),
ES-MS m/e: 573.9 (M+H$^+$).

EXAMPLE 47

[(3SR,4RS)-3-[(RS)-1-(5-Chloro-pyridin-2-yloxy)-ethyl]-4-(3,4-dichloro-phenyl)-pyrrolidin-1-yl]-(6-methanesulfonyl-pyridin-3-yl)-methanone

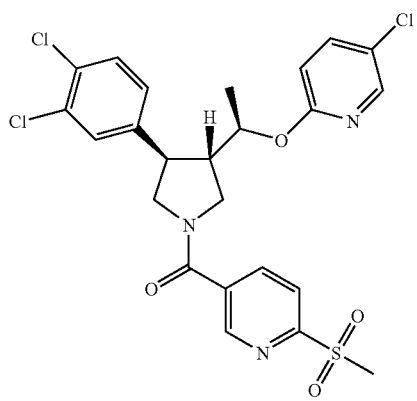

To a stirred solution of [(3SR,4RS)-3-[(RS)-1-(5-Chloro-pyridin-2-yloxy)-ethyl]-4-(3,4-dichloro-phenyl)-pyrrolidin-1-yl]-(6-methylsulfanyl-pyridin-3-yl)-methanone (described herein above) (35 mg, 0.067 mmol) in CH$_2$Cl$_2$ (3 mL) at RT was added mCPBA (33 mg, 0.19 mmol). After 2 hours, an aqeous solution of Na$_2$S$_2$O$_3$ (50 mg in 1 mL H$_2$O) was added. The organic layer was washed with aq. NaHCO$_3$ saturated and dried over Na$_2$SO$_4$. The organic phases were concentrated under vacuo and column chromatography (SiO$_2$, EtOAc) afforded 25 mg (67%) of the title compound as a white solid. ES-MS m/e: 554.9 (M+H$^+$).

EXAMPLE 48

[(3SR,4RS)-3-[(RS)-1-(5-Chloro-pyridin-2-yloxy)-ethyl]-4-(3,4-dichloro-phenyl)-pyrrolidin-1-yl]-(2-methylsulfanyl-pyrimidin-5-yl)-methanone

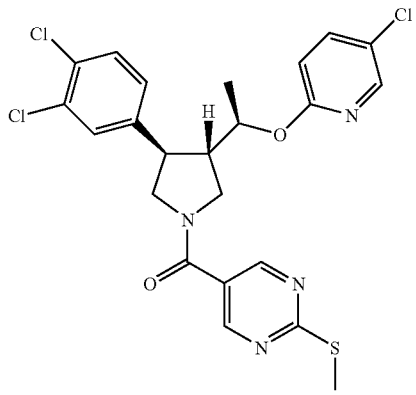

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2-Methylsulfanyl-pyrimidine-5-carboxylic acid (commercially available), ES-MS m/e: 525.3 (M+H$^+$).

EXAMPLE 49

4-[(3SR,4RS)-3-[(RS)-1-(5-Chloro-pyridin-2-yloxy)-ethyl]-4-(3,4-dichloro-phenyl)-pyrrolidin-1-carbonyl]-benzonitrile

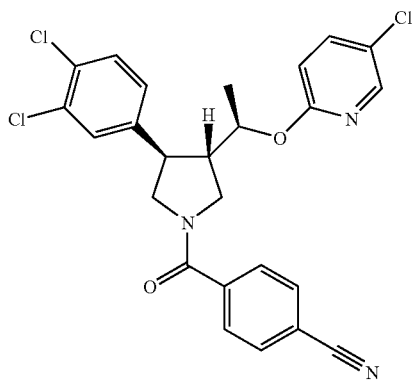

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 4-Cyano-benzoic acid (commercially available),
ES-MS m/e: 488.2 (M+H$^+$).

EXAMPLE 50

5-[(3S,4R)-3-[(R)-1-(5-Chloro-pyridin-2-yloxy)-ethyl]-4-(3,4-dichloro-phenyl)-pyrrolidine-1-carbonyl]-pyrimidine-2-carbonitrile

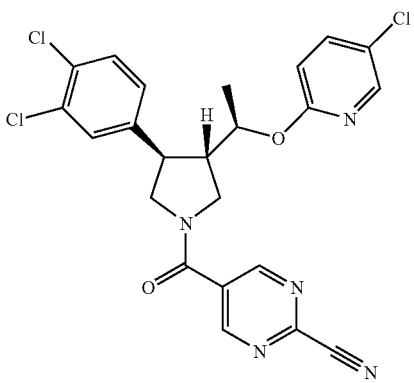

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 2-Cyano-pyrimidine-5-carboxylic acid (prepared from the corresponding commercially available methyl ester by standard hydrolysis),
ES-MS m/e: 504.1 (M+H$^+$).

EXAMPLE 51

[(3SR,4RS)-3-[(RS)-1-(5-Chloro-pyridin-2-yloxy)-ethyl]-4-(3,4-dichloro-phenyl)-pyrrolidin-1-yl]-(2-methanesulfonyl-pyrimidin-5-yl)-methanone

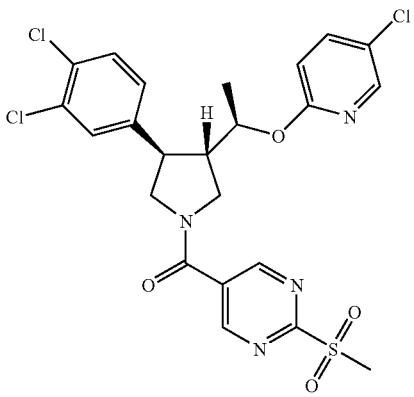

Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2), Carboxylic acid: 2-Methanesulfonyl-pyrimidine-5-carboxylic acid (commercially available), ES-MS m/e: 555.8 (M+H+).

EXAMPLE 52

6-{(SR)-1-[(3RS,4SR)-4-(3,4-Dichloro-phenyl)-1-(6-cyano-pyridine-3-carbonyl)-pyrrolidin-3-yl]-ethoxy}-nicotinonitrile

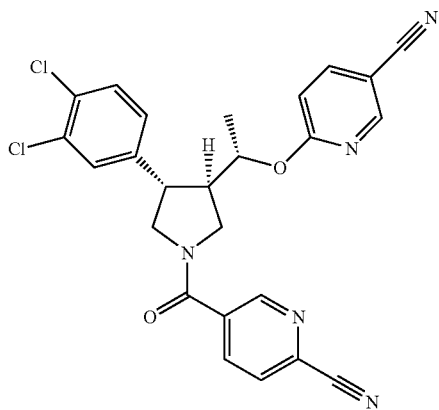

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Cyano-nicotinic acid (commercially available),
ES-MS m/e: 492.3 (M+H+).

EXAMPLES 53 & 54

5-[(3R,4S)-3-[(S)-1-(5-Chloro-pyridin-2-yloxy)-ethyl]-4-(3,4-dichloro-phenyl)-pyrrolidine-1-carbonyl]-pyridine-2-carbonitrile and 5-[(3S,4R)-3-[(R)-1-(5-Chloro-pyridin-2-yloxy)-ethyl]-4-(3,4-dichloro-phenyl)-pyrrolidine-1-carbonyl]-pyridine-2-carbonitrile

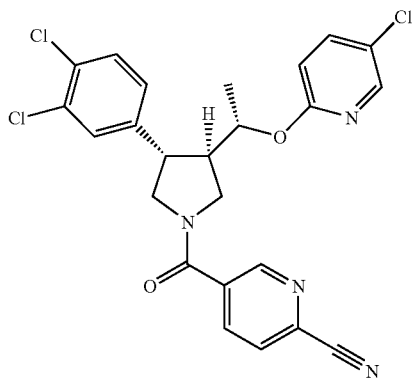

The two optically pure enantiomeres were obtained with a preparative chiral HPLC separation of the racemic mixture prepared from:
Coupling according to general procedure I:
Pyrrolidine intermediate: 5-Chloro-2-{(RS)-1-[(3SR,4RS)-4-(3,4-dichloro-phenyl)-pyrrolidin-3-yl]-ethoxy}-pyridine (XII-B-2),
Carboxylic acid: 6-Cyano-nicotinic acid (commercially available),
ES-MS m/e: 504.1 (M+H+). Same MS spectra for both enantiomers.

EXAMPLE 55

4-{(3SR,4RS)-3-(3,4-Dichloro-phenyl)-4-[(SR)-1-(5-trifluoromethyl-pyridin-2-yloxy)-ethyl]-pyrrolidine-1-carbonyl}-benzonitrile

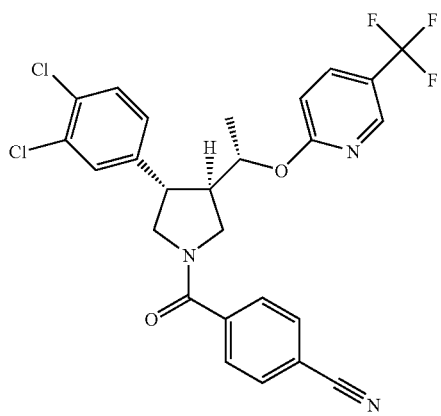

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 4-Cyano-benzoic acid (commercially available),
ES-MS m/e: 534.4 (M+H+).

EXAMPLE 56

5-{(3SR,4RS)-3-(3,4-Dichloro-phenyl)-4-[(SR)-1-(5-trifluoromethyl-pyridin-2-yloxy)-ethyl]-pyrrolidine-1-carbonyl}-pyridine-2-carbonitrile

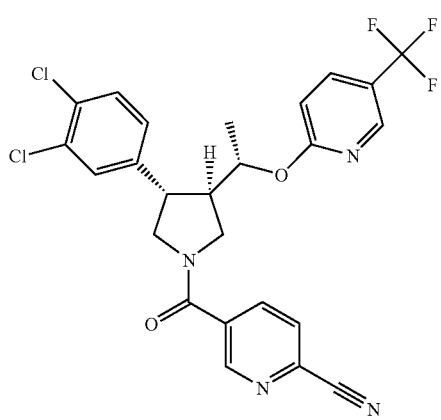

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 6-Cyano-nicotinic acid (commercially available),
ES-MS m/e: 535.6 (M+H⁺).

EXAMPLE 57

6-{(SR)-1-[(3RS,4SR)-4-(3,4-Dichloro-phenyl)-1-(2-methyl-pyrimidine-5-carbonyl)-pyrrolidin-3-yl]-ethoxy}-nicotinonitrile

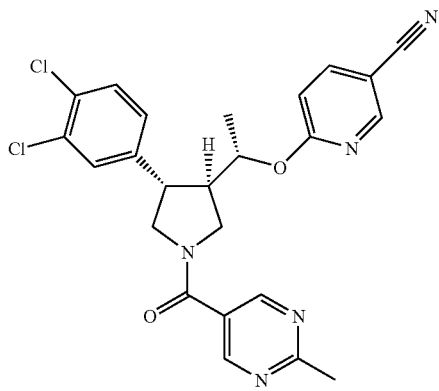

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 2-Methyl-pyrimidine-5-carboxylic acid (commercially available),
ES-MS m/e: 484.2 (M+H⁺).

EXAMPLE 58

5-[(3RS,4SR)-3-[(SR)-1-(5-Cyano-pyridin-2-yloxy)-ethyl]-4-(3,4-dichloro-phenyl)-pyrrolidine-1-carbonyl]-pyridine-2-sulfonic acid dimethylamide

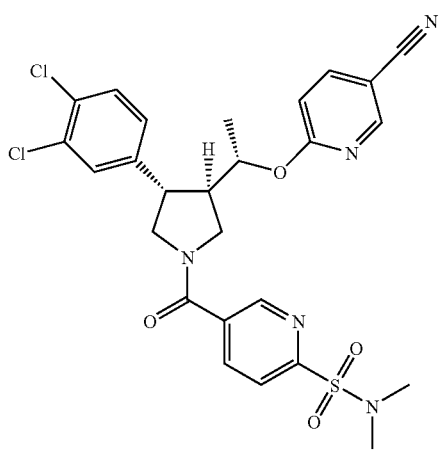

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Dimethylsulfamoyl-nicotinic acid (described herein after), 6-Dimethylsulfamoyl-nicotinic acid 1$^{st}$ step: To a stirred solution of 6-sulfamoyl-nicotinic acid methyl ester (250 mg, 1.15 mmol) in DMF (10 mL) at 0° C. was added NaH (53 mg, 55%, 1.20 mmol). After 10 minutes, MeI (0.079 mL, 1.26 mL) was added. Stirring was continued for one hour before the reaction was quenched upon addition of H$_2$O. The product was extracted with EtOAc, the combined organic layers were dried over Na$_2$SO$_4$ and concentrated under vacuo. Column chromatography (SiO$_2$, EtOAc/H, 1/2) afforded 51 mg of the title compound (19%) as a white solid.

EXAMPLE 59

6-{(SR)-1-[(3RS,4SR)-4-(3,4-Dichloro-phenyl)-1-(4-oxazol-5-yl-benzoyl)-pyrrolidin-3-yl]-ethoxy}-nicotinonitrile

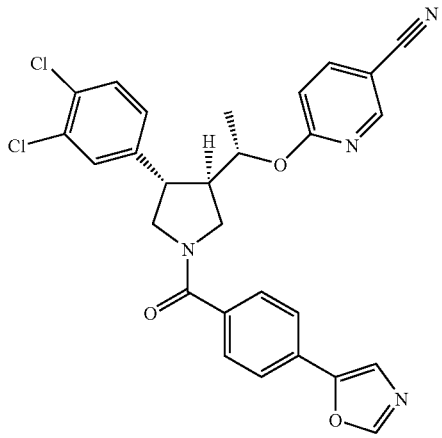

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-Oxazol-5-yl-benzoic acid (commercially available),
ES-MS m/e: 534.8 (M+H⁺).

EXAMPLE 60

6-((SR)-1-{(3RS,4SR)-4-(3,4-Dichloro-phenyl)-1-[4-(3-methyl-[1,2,4]oxadiazol-5-yl)-benzoyl]-pyrrolidin-3-yl}-ethoxy)-nicotinonitrile

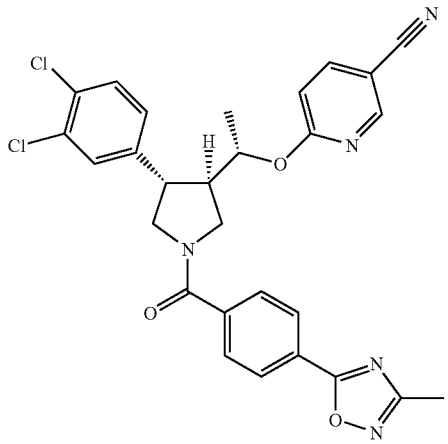

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-(3-Methyl-[1,2,4]oxadiazol-5-yl)-benzoic acid (commercially available),
ES-MS m/e: 549.8 (M+H$^+$).

EXAMPLE 61

6-((SR)-1-{(3RS,4SR)-4-(3,4-Dichloro-phenyl)-1-[4-(5-methyl-[1,2,4]oxadiazol-3-yl)-benzoyl]-pyrrolidin-3-yl}-ethoxy)-nicotinonitrile

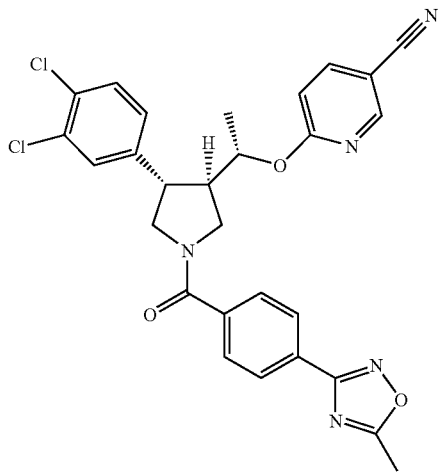

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-(5-Methyl-[1,2,4]oxadiazol-3-yl)-benzoic acid (commercially available),
ES-MS m/e: 550.0 (M+H$^+$).

EXAMPLE 62

6-((SR)-1-{(3RS,4SR)-4-(3,4-Dichloro-phenyl)-1-[4-(3-ethyl-[1,2,4]oxadiazol-5-yl)-benzoyl]-pyrrolidin-3-yl}-ethoxy)-nicotinonitrile

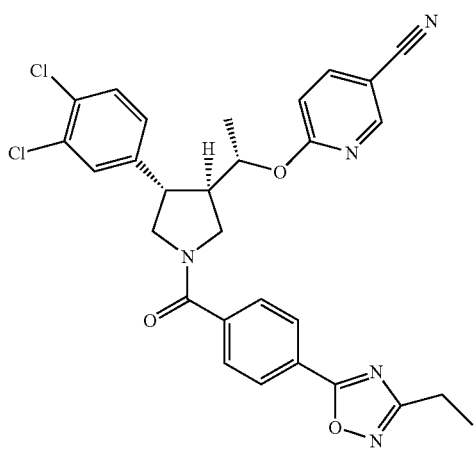

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-(3-Ethyl-[1,2,4]oxadiazol-5-yl)-benzoic acid (commercially available),
ES-MS m/e: 563.9 (M+H$^+$).

EXAMPLE 63

6-{(SR)-1[-(3RS,4SR)-4-(3,4-Dichloro-phenyl)-1-(4-[1,3,4]oxadiazol-2-yl-benzoyl)-pyrrolidin-3-yl]-ethoxy}-nicotinonitrile

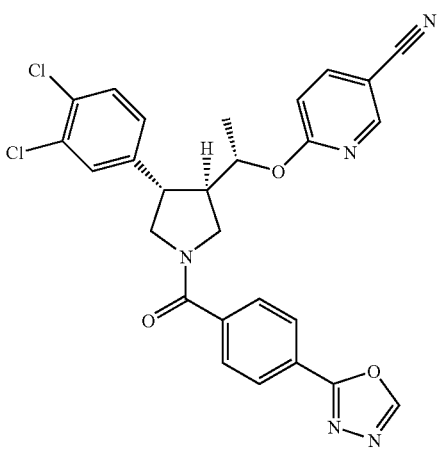

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-[1,3,4] Oxadiazol-2-yl-benzoic acid (commercially available),
ES-MS m/e: 535.7M+H$^+$).

EXAMPLE 64

6-((SR)-1-{(3RS,4SR)-4-(3,4-Dichloro-phenyl)-1-[4-(2-methyl-imidazol-1-yl)-benzoyl]-pyrrolidin-3-yl}-ethoxy)-nicotinonitrile

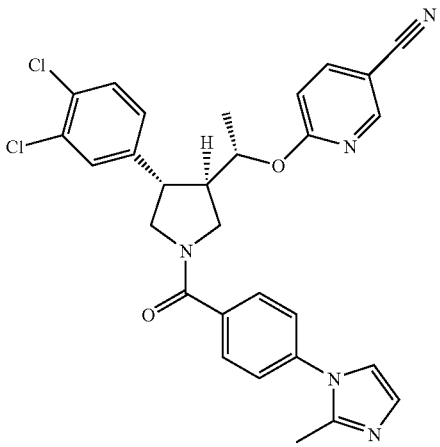

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-(2-Methyl-imidazol-1-yl)-benzoic acid (commercially available),
ES-MS m/e: 547.8 (M+H$^+$).

EXAMPLE 65

6-{(SR)-1-[(3RS,4SR)-4-(3,4-Dichloro-phenyl)-1-(6-pyrazol-1-yl-pyridine-3-carbonyl)-pyrrolidin-3-yl]-ethoxy}-nicotinonitrile

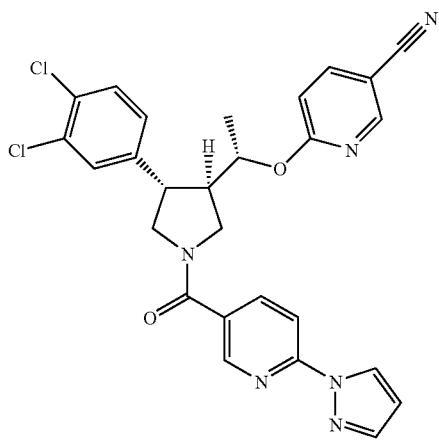

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Pyrazol-1-yl-nicotinic acid (commercially available),
ES-MS m/e: 534.9 (M+H$^+$).

EXAMPLE 66

6-{(SR)-1-[(3RS,4SR)-4-(3,4-Dichloro-phenyl)-1-(6-methanesulfonyl-pyridine-3-carbonyl)-pyrrolidin-3-yl]-ethoxy}-nicotinonitrile

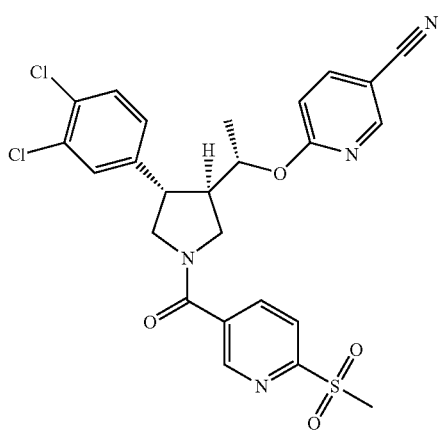

An amid coupling according to general procedure I, between the pyrrolidine intermediate 6-{(SR)-1-[(3RS,4SR)-4-(3,4-dichloro-phenyl)-pyrrolidin-3-yl]-ethoxy}-nicotinonitrile (XII-B-3) and the carboxylic acid 6-methylsulfanyl-nicotinic acid (commercially available), afforded the corresponding amid. The crude product was dissolved in CH$_2$Cl$_2$ and mCPBA (1.4 eq.) was added. Stirring was continued for 2 hours at RT, before the reaction was quenched upon addition of aq. Na$_2$S$_2$O$_3$, and then the organic phase was washed with aq. NaOH. The organic phase was dried over Na$_2$SO$_4$ and concentrated under vacuo. Column chromatography afforded 22 mg (58%) of the title compound as a white solid. ES-MS m/e: 545.1 (M+H$^+$).

EXAMPLE 67

6-{(SR)-1-[(3RS,4SR)-1-(4-Cyano-2-fluoro-benzoyl)-4-(3,4-dichloro-phenyl)-pyrrolidin-3-yl]-ethoxy}-nicotinonitrile

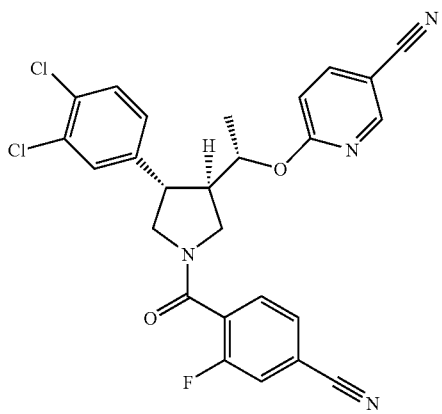

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-Cyano-2-fluoro-benzoic acid (commercially available),
ES-MS m/e: 509.1 (M+H$^+$).

EXAMPLE 68

6-{(SR)-1-[(3RS,4SR)-4-(3,4-Dichloro-phenyl)-1-(6-methyl-pyridine-3-carbonyl)-pyrrolidin-3-yl]-ethoxy}-nicotinonitrile

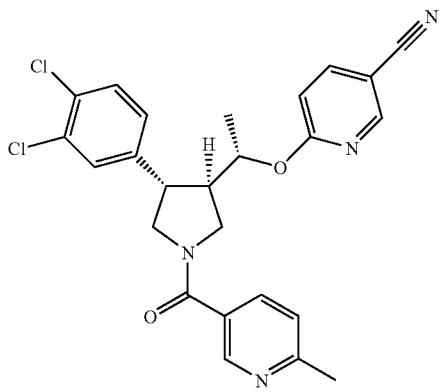

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Methyl-nicotinic acid (commercially available), ES-MS m/e: 481.2 (M+H⁺).

EXAMPLE 69

6-{(SR)-1-[(3RS,4SR)-1-(1H-Benzoimidazole-5-carbonyl)-4-(3,4-dichloro-phenyl)-pyrrolidin-3-yl]-ethoxy}-nicotinonitrile

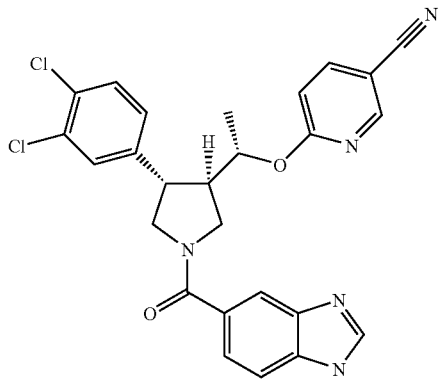

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 1H-Benzoimidazole-5-carboxylic acid (commercially available), ES-MS m/e: 506.1 (M+H⁺).

EXAMPLE 70

6-{(SR)-1-[(3RS,4SR)-4-(3,4-Dichloro-phenyl)-1-(2-methoxy-pyrimidine-5-carbonyl)-pyrrolidin-3-yl]-ethoxy}-nicotinonitrile

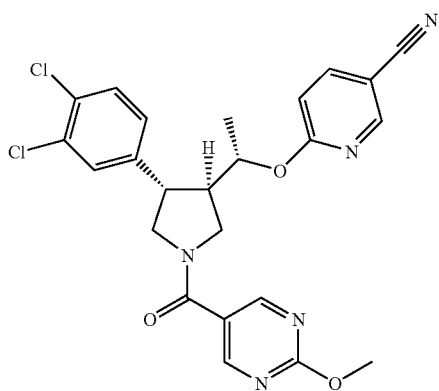

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 2-Methoxy-pyrimidine-5-carboxylic acid (commercially available), ES-MS m/e: 498.2 (M+H⁺).

EXAMPLE 71

6-{(SR)-1-[(3RS,4SR)-4-(3,4-Dichloro-phenyl)-1-(6-imidazol-1-yl-pyridine-3-carbonyl)-pyrrolidin-3-yl]-ethoxy}-nicotinonitrile

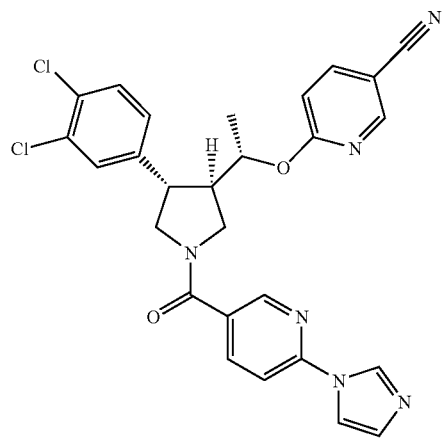

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Imidazol-1-yl-nicotinic acid (commercially available), ES-MS m/e: 533.1 M+H⁺).

EXAMPLE 72

6-{(SR)-1-[(3RS,4SR)-4-(3,4-Dichloro-phenyl)-1-(6-trifluoromethyl-pyridine-3-carbonyl)-pyrrolidin-3-yl]-ethoxy}-nicotinonitrile

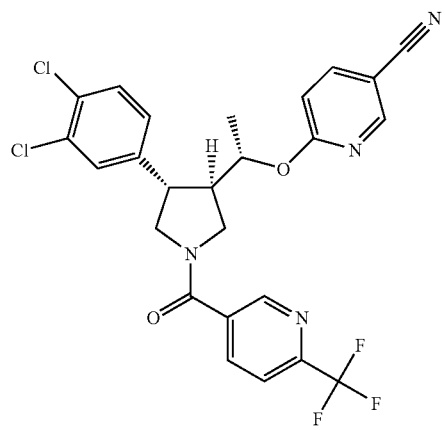

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 6-Trifluoromethyl-nicotinic acid (commercially available), ES-MS m/e: 535.1 M+H⁺.

EXAMPLE 73

6-{(SR)-1-[(3RS,4SR)-4-(3,4-Dichloro-phenyl)-1-(5-methyl-pyridine-3-carbonyl)-pyrrolidin-3-yl]-ethoxy}-nicotinonitrile

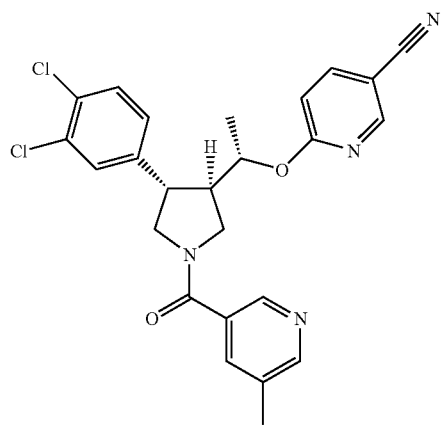

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 5-Methyl-nicotinic acid (commercially available), ES-MS m/e: 481.1 (M+H⁺).

EXAMPLE 74

6-{(SR)-1-[(3RS,4SR)-4-(3,4-Dichloro-phenyl)-1-(5-fluoro-pyridine-3-carbonyl)-pyrrolidin-3-yl]-ethoxy}-nicotinonitrile

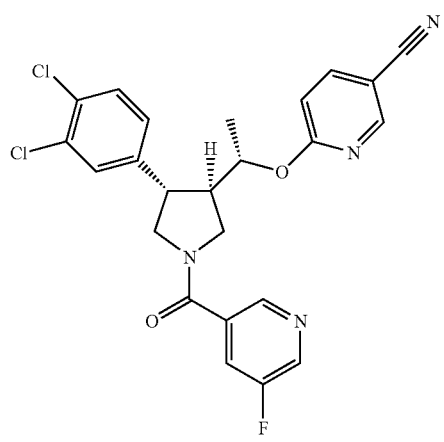

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 5-Fluoro-nicotinic acid (commercially available), ES-MS m/e: 485.4 (M+H⁺).

EXAMPLE 75

6-{(SR)-1-[(3RS,4SR)-4-(3,4-Dichloro-phenyl)-1-(6-fluoro-pyridine-3-carbonyl)-pyrrolidin-3-yl]-ethoxy}-nicotinonitrile

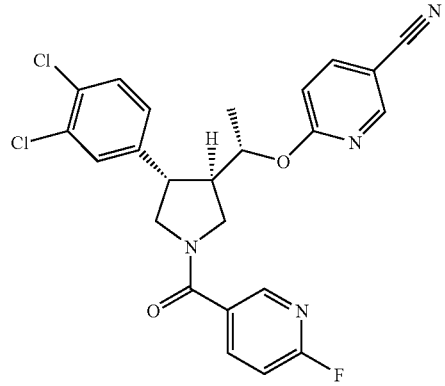

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Fluoro-nicotinic acid (commercially available), ES-MS m/e: 485.4 (M+H⁺).

EXAMPLE 76

6-((SR)-1-{(3RS,4SR)-4-(3,4-Dichloro-phenyl)-1-[6-(2,2,2-trifluoro-ethoxy)-pyridine-3-carbonyl]-pyrrolidin-3-yl}-ethoxy)-nicotinonitrile

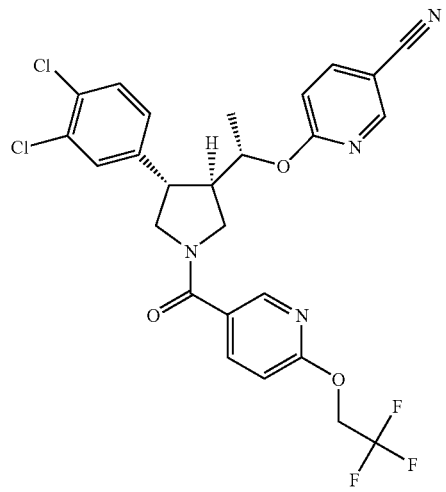

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 6-(2,2,2-Trifluoro-ethoxy)-nicotinic acid (commercially available), ES-MS m/e: 565.2 (M+H⁺).

EXAMPLE 77

6-{(SR)-1-[(3RS,4SR)-4-(3,4-Dichloro-phenyl)-1-(pyridazine-4-carbonyl)-pyrrolidin-3-yl]-ethoxy}-nicotinonitrile

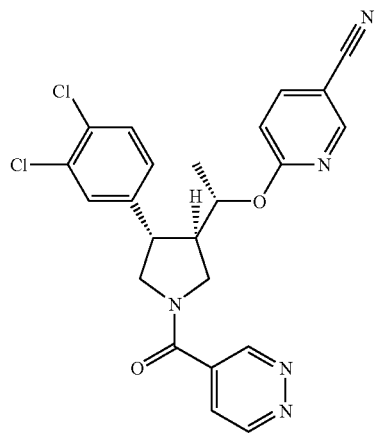

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: Pyridazine-4-carboxylic acid (commercially available), ES-MS m/e: 468.1 (M+H⁺).

EXAMPLE 78

6-{(SR)-1-[(3RS,4SR)-1-(3-Chloro-6-methyl-pyridazine-4-carbonyl)-4-(3,4-dichloro-phenyl)-pyrrolidin-3-yl]-ethoxy}-nicotinonitrile

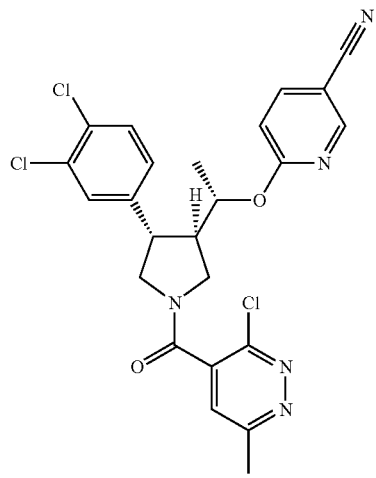

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 3-Chloro-6-methyl-pyridazine-4-carboxylic acid (commercially available), ES-MS m/e: 518.0 (M+H⁺).

EXAMPLE 79

{(3SR,4RS)-3-(3,4-Dichloro-phenyl)-4-[(SR)-1-(5-trifluoromethyl-pyridin-2-yloxy)-ethyl]-pyrrolidin-1-yl}-(2-methyl-pyrimidin-5-yl)-methanone

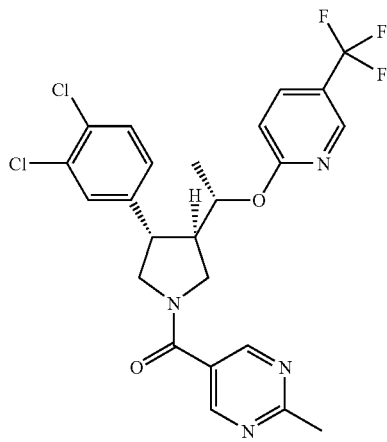

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 2-Methyl-pyrimidine-5-carboxylic acid (commercially available),
ES-MS m/e: 525.2 (M+H⁺).

EXAMPLE 80

{(3SR,4RS)-3-(3,4-Dichloro-phenyl)-4-[(SR)-1-(5-trifluoromethyl-pyridin-2-yloxy)-ethyl]-pyrrolidin-1-yl}-(6-pyrazol-1-yl-pyridin-3-yl)-methanone

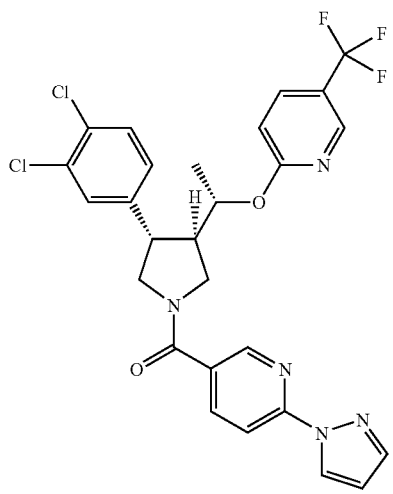

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 6-Pyrazol-1-yl-nicotinic acid (commercially available),
ES-MS m/e: 576.3 (M+H⁺).

EXAMPLE 81

(6-Chloro-pyridin-3-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone

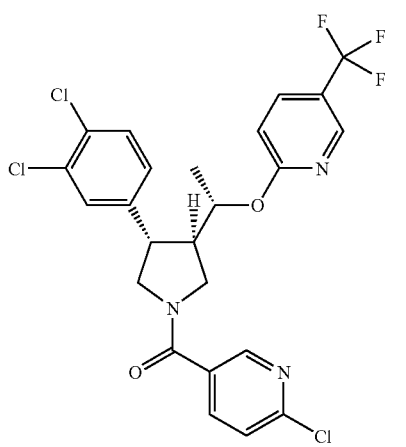

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 6-Chloro-nicotinic acid (commercially available), ES-MS m/e: 546.1 (M+H⁺).

EXAMPLE 82

(2-Chloro-pyridin-4-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone

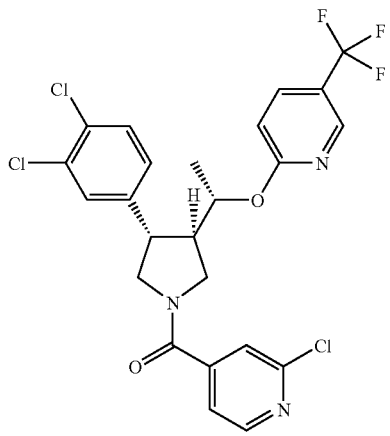

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 2-Chloro-isonicotinic acid (commercially available), ES-MS m/e: 544.0 M+H⁺).

EXAMPLE 83

{(3SR,4RS)-3-(3,4-Dichloro-phenyl)-4-[(SR)-1-(5-trifluoromethyl-pyridin-2-yloxy)-ethyl]-pyrrolidin-1-yl}-[4-(3-methyl-[1,2,4]oxadiazol-5-yl)-phenyl]-methanone

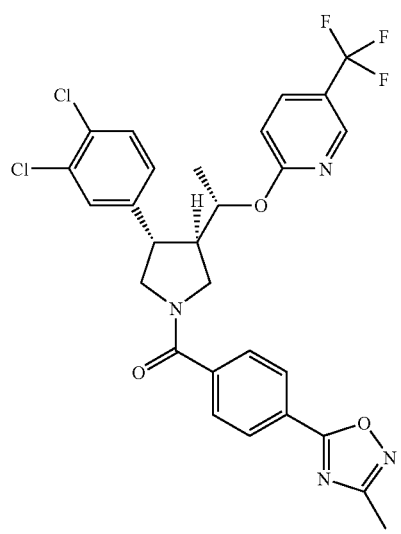

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 4-(3-Methyl-[1,2,4]oxadiazol-5-yl)-benzoic acid (commercially available), ES-MS m/e: 591.3 (M+H⁺).

EXAMPLE 84

6-{(S)-1[-(3R,4S)-1-(2-Cyclopropyl-pyrimidine-5-carbonyl)-4-(3,4-dichloro-phenyl)-pyrrolidin-3-yl]-ethoxy}-nicotinonitrile

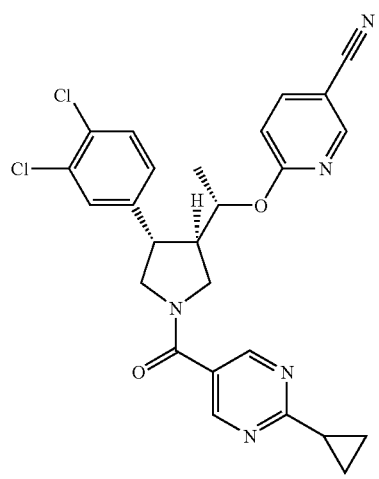

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 2-Cyclopropyl-pyrimidine-5-carboxylic acid (commercially available), ES-MS m/e: 508.2 (M+H$^+$).

EXAMPLE 85

(2-Cyclopropyl-pyrimidin-5-yl)-{(3SR,4RS)-3-(3,4-dichloro-phenyl)-4-[(SR)-1-(5-trifluoromethyl-pyridin-2-yloxy)-ethyl]-pyrrolidin-1-yl}-methanone

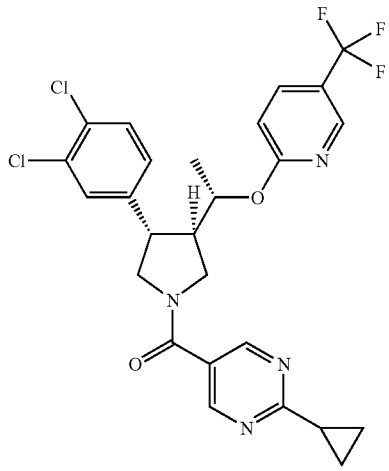

Coupling according to general procedure I:
Pyrrolidine intermediate: 2-{(SR)-1-[(3RS,4SR)-4-(3,4-Dichloro-phenyl)-pyrrolidin-3-yl]-ethoxy}-5-trifluoromethyl-pyridine (XII-B-4)
Carboxylic acid: 2-Cyclopropyl-pyrimidine-5-carboxylic acid (commercially available), ES-MS m/e: 551.2 (M+H$^+$).

EXAMPLE 86

6-{(SR)-1-[(3RS,4SR)-4-(3,4-Dichloro-phenyl)-1-(6-ethyl-5-methyl-pyridine-3-carbonyl)-pyrrolidin-3-yl]-ethoxy}-nicotinonitrile

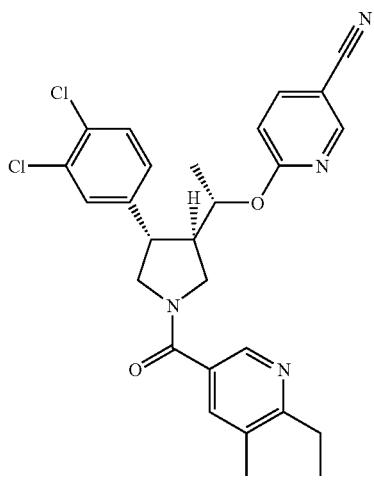

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Ethyl-5-methyl-nicotinic acid (described in J. Het. Chem. 1987, 24(2), 351-5), ES-MS m/e: 509.3 (M+H$^+$).

EXAMPLE 87

[(3RS,4SR)-3-[(RS)-1-(5-Chloro-pyridin-2-yloxy)-2-hydroxy-ethyl]-4-(3,4-dichloro-phenyl)-pyrrolidin-1-yl]-(2-methyl-pyrimidin-5-yl)-methanone

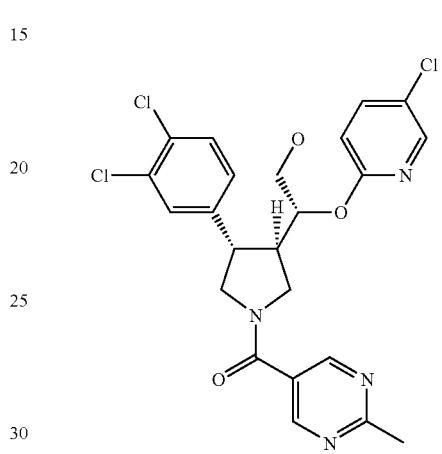

a) (3RS,4SR)-1-Benzyl-4-(3,4-dichloro-phenyl)-pyrrolidine-3-carboxylic acid

To a solution of N-(methoxymethyl)-N-(phenylmethyl)-N-(trimethylsilyl)methylamine (16.87 g, 0.071 mol) and (E)-3-(3,4-Dichloro-phenyl)-acrylic acid (7.71g, 0.036 mol) in THF (50 mL) was added trifluoroacetic acid (0.19 mL, 0.002 mol) at 0° C. The mixture was gradually warmed to room temperature and stirred overnight. It was then diluted with n-heptane (250 mL). The resulted white precipitation was collected and washed with heptane affording 11.6 g (94%) of the title compound as a white solid. ES-MS m/e: 350.2 (M+H$^+$).

b) (3RS,4SR)-1-Benzyl-4-(3,4-dichloro-phenyl)-pyrrolidine-3-carboxylic acid methoxy-methyl-amide To a solution of N,O-dimethylhydroxylamine hydrochloride (0.41 g, 4.2 mmol) and 1.23 g (3.5 mmol) of (3RS,4SR)-1-Benzyl-4-(3,4-dichloro-phenyl)-pyrrolidine-3-carboxylic acid in DMF (20 mL) at RT was added Hunig base (1.79 ml, 10.5 mmol) and HATU (1.468 g, 3.9 mmol) and stirring was continued for one hour. The reaction mixture was diluted with ethyl acetate and washed with aq. ammonium chloride solution three times. The separated organic layer was washed with brine and dried on Na$_2$SO$_4$ and concentrated under vacuo yielding 1.36 g (99%) of the title compound as a light yellow oil. ES-MS m/e: 393.1 (M+H$^+$).

c) (3RS,4SR)-1-Benzyl-4-(3,4-dichloro-phenyl)-pyrrolidine-3-carbaldehyde

To a solution of (3RS,4SR)-1-benzyl-4-(3,4-dichloro-phenyl)-pyrrolidine-3-carboxylic acid methoxy-methyl-amide (3A) 6.58 g (0.017 mol) dissolved in THF (100 mL) was added 16 mL (0.017 mol) of lithiumaluminiumhydride (1.0M in THF) dropwise at 0° C. and stirred for one hour. The reaction was quenched by aq. ammonium chloride solution and extracted with ethylacetate twice. The combined organic layers were dried on anhydrous sodium sulfate and concentrated in vaccuo. The residue was purified by silica gel column chromatography eluted by a mixture of heptane and ethyl acetate (3:2) yielding 5.21 g (93%) of the title compound as a light yellow oil. ES-MS m/e: 334.2 (M+H$^+$).

d) (3SR,4RS)-1-Benzyl-3-(3.4-dichloro-phenyl)-4-vinyl-pyrrolidine

To a suspension of methyltriphenylphosphonium iodide (5.53 g, 0.0136 mol) in THF (50 mL) was added n-BuLi (1.6N in heptane, 6.5 mL, 0.0104 mol) dropwise at 0° C. and stirred for one hour. To this reaction mixture was added a solution of (3RS,4SR)-1-benzyl-4-(3,4-dichloro-phenyl)-pyrrolidine-3-carbaldehyde 2.68 g (0.008 mol) in THF (15 mL) dropwise at 0° C. and stirred for another one hour. The reaction was quenched by aq. ammonium chloride solution and extracted with ethylacetate. The separated organic layer was dried on anhydrous sodium sulfate and concentrated in vaccuo. The residue was purified by silica gel column chromatography eluted by a mixture of heptane and ethyl acetate (4: 1) yielding 2.12 g (80%) of the title compound as a light yellow oil. ES-MS m/e: 332.1 (M+H$^+$).

e) (SR)-1-[(3RS,4SR)-1-Benzyl-4-(3,4-dichloro-phenyl)-pyrrolidin-3-yl]-2-(tert-butyl-dimethyl-silanyloxy)-ethanol and (RS)-1-[(3RS,4SR)-1-Benzyl-4-(3,4-dichloro-phenyl)-pyrrolidin-3-yl]-2-(tert-butyl-dimethyl-silanyloxy)-ethanol To a solution of OsO$_4$ (73 mg, 0.3 mmol) in MeCN (3 mL), t-BuOH (4.5 mL) and water (1.5 mL) was added NMO (aq. 50% solution, 0.42 mL, 2 mmol) and (3SR,4RS)-1-benzyl-3-(3,4-dichloro-phenyl)-4-vinyl-pyrrolidine (331 mg, 1.0 mmol) as solution of MeCN (4 mL) at room temperature. The whole mixture was vigorously stirred over night. The reaction was quenched by an addition of sat. aq. Na$_2$SO$_2$ solution. The mixture was then concentrated in vacuo, followed by dilution with AcOEt, and washed with brine. The separated aqueous phase was extracted with AcOEt twice. The combined organic phase were dried over Na$_2$SO$_4$. The residue was purified by silica gel column chromatography eluted by DCM to aceton yielding 255 mg (70%) of a mixture of the diastereomeric diols as a light yellow oil. ES-MS m/e: 366.0 (M+H$^+$).

The residue was dissolved in DCM (10 mL) followed by additions of TBDMSCl (133 mg, 0.86 mmol), Hunig base (0.205 mL, 1.21 mmol) and DMAP (20 mg, 0.16 mmol) subsequently at room temperature, and the resulted mixture was stirred overnight. The reaction mixture was diluted with ethyl acetate and washed with aq. ammonium chloride solution three times. The separated organic phase was dried over sodium sulfate and concentrated in vaccuo after filtration. The residue was purified by silica gel column chromatography eluted with a mixture of heptane and ethyl acetate (4:1 to 3:1) yielding 124 mg (32%) of (SR)-1-[(3RS,4SR)-1-benzyl-4-(3, 4-dichloro-phenyl)-pyrrolidin-3-yl]-2-(tert-butyl-dimethyl-silanyloxy)-ethanol and 156 mg (40%) of (RS)-1-[(3RS, 4SR)-1-benzyl-4-(3,4-dichloro-phenyl)-pyrrolidin-3-yl]-2-(tert-butyl-dimethyl-silanyloxy)-ethanol (6A-2) as a light brown oil. ES-MS m/e: 480.2 (M+H$^+$).

f) 2-[(RS)-1-[(3RS,4SR)-1-Benzyl-4-(3,4-dichloro-phenyl)-pyrrolidin-3-yl]-2-(tert-butyl-dimethyl-silanyloxy)-ethoxy]-5-chloro-pyridine (RS)-1-[(3SR,4RS)-1-Benzyl-4-(3,4-dichloro-phenyl)-pyrrolidin-3-yl]-2-(tert-butyl-dimethyl-silanyloxy)-ethanol (123 mg. 0.256 mmol) and PPh$_3$ (PPh$_3$ polymer bound, 3 mmol PPh$_3$/g resin) (125 mg, 0.38 mmol) were suspended in THF (3 mL). To the mixture were added 5-chloro-pyridin-2-ol (50 mg, 0.384 mmol) and then DBAD (0.088 g, 0.384 mmol). The reaction mixture was stirred at 45° C. over night. The mixture was diluted with ethyl acetate and filtered on celite and concentrated under vacuo. The residue was purified by column chromatography (SiO$_2$, EtOAc/H, 1:15) yielded 108 mg (72%) of the title compound as a colorless oil. ES-MS m/e: 593.3 (M+H$^+$).

g) 2-{(RS)-2-(tert-Butyl-dimethyl-silanyloxy)-1-[(3RS,4SR)-4-(3,4-dichloro-phenyl)-pyrrolidin-3-yl]-ethoxy}-5-chloro-pyridine To a solution of 2-[(RS)-1-[(3RS,4SR)-1-benzyl-4-(3,4-dichloro-phenyl)-pyrrolidin-3-yl]-2-(tert-butyl-dimethyl-silanyloxy)-ethoxy]-5-chloro-pyridine (7A-1) 108 mg (0.182 mmol) dissolved in toluene (2 mL) was added 0.059 mL (0.547 mmol) of 1-chloroethyl chloroformate and 0.093 mL (0.547 mmol) of Hunig base subsequently, and the mixture was heated at 100° C. for 40 minutes, then concentrated in vaccuo. The residue was dissolved in methanol (5 mL) and heated at reflux temperature for 30 minutes. The mixture was concentrated in vacuo and diluted with ethyl acetate, then washed with aq. sodium bicarbonate solution twice. The combined organic layers was dried over sodium sulfate and concentrated in vaccuo after filtration. The residue was purified by silica gel column chromatography (DCM/MeOH 10:1 to 4:1) yielding 0.047 g (51%) of the title compound as a light brown oil. ES-MS m/e: 501.2 (M+H$^+$).

h) [(3RS,4SR)-3-[(RS)-2-(tert-Butyl-dimethyl-silanyloxy)-1-(5-chloro-pyridin-2-yloxy)-ethyl]-4-(3,4-dichloro-phenyl)-pyrrolidin-1-yl]-(2-methyl-pyrimidin-5-yl)-methanone To a solution of 2-{(RS)-2-(tert-Butyl-dimethyl-silanyloxy)-1-[(3RS,4SR)-4-(3,4-dichloro-phenyl)-pyrrolidin-3-yl]-ethoxy}-5-chloro-pyridine (8A-1) (220 mg) in DMF (12 mL) at −20° C. were added Hunig base (0.132 mL, 0.78 mmol) and then HATU (202 mg). The mixture was diluted with ethyl acetate and washed with aq.ammonium chloride solution three times and aq. sodium bicarbonate solution. The separated organic phase was dried over sodium sulfate and concentrated in vaccuo after filtration. The residue was purified by TLC (SiO$_2$, MeOH/DCM, 1:20) yielded 24 mg (40%) of the title compound as a light yellow oil. ES-MS m/e: 623.1 M+H$^+$).

i) [(3RS,4SR)-3-[(RS)-1-(5-Chloro-pyridin-2-yloxy)-2-hydroxy-ethyl]-4-(3,4-dichloro-phenyl)-pyrrolidin-1-yl]-(2-methyl-pyrimidin-5-yl)-methanone To a solution of [(3RS,4SR)-3-[(RS)-2-(tert-butyl-dimethyl-silanyloxy)-1-(5-chloro-pyridin-2-yloxy)-ethyl]-4-(3, 4-dichloro-phenyl)-pyrrolidin-1-yl]-(6-methyl-pyridazin-4-yl)-methanone 0.024 g (0.038 mmol) dissolved in THF (4 mL) was added 0.05 mL of TBAF (1.0M in THF). The reaction mixture was stirred for 30 minutes at room temperature.

The mixture was diluted with ethyl acetate and washed with water and aq. sodium bicarbonate solution subsequently. The separated organic phase was dried over sodium sulfate and concentrated in vaccuo after filtration. The residue was purified by TLC (SiO$_2$, MeOH/DCM, 1:10) yielded 18 mg (93%) of the title compound as a light yellow oil. ES-MS m/e: 509.2 (M+H$^+$).

EXAMPLE 88

[(3RS,4SR)-3-[(SR)-1-(5-Chloro-pyridin-2-yloxy)-2-hydroxy-ethyl]-4-(3,4-dichloro-phenyl)-pyrrolidin-1-yl]-(2-methyl-pyrimidin-5-yl)-methanone

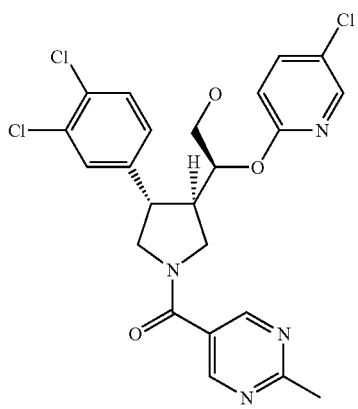

a) 2-[(SR)-1-[(3RS,4SR)-1-Benzyl-4-(3,4-dichloro-phenyl)-pyrrolidin-3-yl]-2-(tert-butyldimethyl-silanyloxy)-ethoxy]-5-chloro-pyridine (SR)-1-[(3SR,4RS)-1-Benzyl-4-(3,4-dichloro-phenyl)-pyrrolidin-3-yl]-2-(tert-butyl-dimethyl-silanyloxy)-ethanol (described herein above) (13.2 mg. 0.0275 mmol) and PPh$_3$ (PPh$_3$ polymer bound, 3 mmol PPh$_3$/g resin) (18 mg, 0.055 mmol) were suspended in THF (2 mL). To the mixture were added 5-chloro-pyridin-2-ol (7 mg, 0.055 mmol) and then DBAD (13 mg, 0.055 mmol). The reaction mixture was stirred at 40° C. over night. The mixture was diluted with ethyl acetate and filtered on celite and concentrated under vacuo. The residue was purified by TLC (SiO$_2$, EtOAc/H, 1:4) yielded 7.2 mg (44%) of the title compound as a colorless oil. ES-MS m/e: 593.3 (M+H$^+$).

b) 2-{(SR)-2-(tert-Butyl-dimethyl-silanyloxy)-1-[(3RS,4SR)-4-(3,4-dichloro-phenyl)-pyrrolidin-3-yl]-ethoxy}-5-chloro-pyridine The titled compound was obtained as a light brown oil from 2-[(SR)-1-[(3RS,4SR)-1-benzyl-4-(3,4-dichloro-phenyl)-pyrrolidin-3-yl]-2-(tert-butyl-dimethyl-silanyloxy)-ethoxy]-5-chloro-pyridine following the general procedure IV. ES-MS m/e: 501.1 (M+H$^+$)

c) [(3RS,4SR)-3-[(SR)-2-(tert-Butyl-dimethyl-silanyloxy)-1-(5-chloro-pyridin-2-yloxy)-ethyl]-4-(3,4-dichloro-phenyl)-pyrrolidin-1-yl]-(2-methyl-pyrimidin-5-yl)-methanone The titled compound was obtained as a light yellow oil starting from 2-{(SR)-2-(tert-butyl-dimethyl-silanyloxy)-1-[(3RS,4SR)-4-(3,4-dichloro-phenyl)-pyrrolidin-3-yl]-ethoxy}-5-chloro-pyridine (8A-2) following the general procedure I. ES-MS m/e: 623.1 (M+H$^+$).

d) [(3RS,4SR)-3-[(SR)-1-(5-Chloro-pyridin-2-yloxy)-2-hydroxy-ethyl]-4-(3,4-dichloro-phenyl-pyrrolidin-1-yl]-(2-methyl-pyrimidin-5-yl)-methanone To a solution of [(3RS,4SR)-3-[(SR)-2-(tert-butyl-dimethyl-silanyloxy)-1-(5-chloro-pyridin-2-yloxy)-ethyl]-4-(3,4-dichloro-phenyl)-pyrrolidin-1-yl]-(2-methyl-pyrimidin-5-yl)-methanone (10B) (3.9 mg, 0.0063 mmol) in THF (2 mL) was added TBAF (1.0M in THF, 0.01 mL, 0.01 mmol) at 0° C. The mixture was stirred for 1 hour, then quenched by an addition of aq.ammonium chloride solution and extracted with ethyl acetate. The separated organic layer was washed with brine, then dried over anhydrous sodium sulfate.

The titled compound was obtained as a light yellow oil (1.6 mg, 50% yield) after purification of the residue by TLC (SiO$_2$, DCM/MeOH 10:1). ES-MS m/e: 509.1 (M+H$^+$).

EXAMPLE 89

6-{(SR)-1-[(3RS,4SR)-4-(3,4-Dichloro-phenyl)-1-(6-methyl-pyridazine-4-carbonyl)-pyrrolidin-3-yl]-ethoxy}-nicotinonitrile

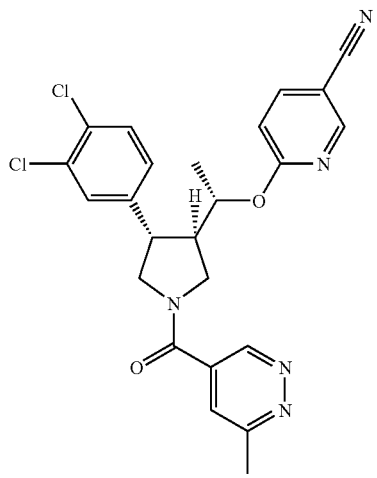

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 6-Methyl-pyridazine-4-carboxylic acid (described herein after),
ES-MS m/e: 482.3 (M+H$^+$).

6-Methyl-pyridazine-4-carboxylic acid

To a stirred solution of 3-chloro-6-methyl-pyridazine-4-carboxylic acid (500 mg, 2.89 mmol) in MeOH (50 mL) was added NaOH (395 mg, 9.85 mmol) in pellets, followed by 150 mg of Pd/C (10%). The reaction mixture was put under a H$_2$ atmosphere for 3 hours (atmospheric pressure). The reaction mixture was filtered on celite, acidified with aq. HCl (ph=6), and concentrated under vacuo. Column chromatography (SiO$_2$, CH$_2$Cl$_2$/MeOH 7/3) yielded 120 mg (29%) of 6-methyl-pyridazine-4-carboxylic acid as a brown solid.

EXAMPLE 90

{(3S,4R)-3-(4-Chloro-3-fluoro-phenyl)-4-[(S)-1-(5-chloro-pyridin-2-yloxy)-ethyl]-pyrrolidin-1-yl}-(2-methyl-pyrimidin-5-yl)-methanone

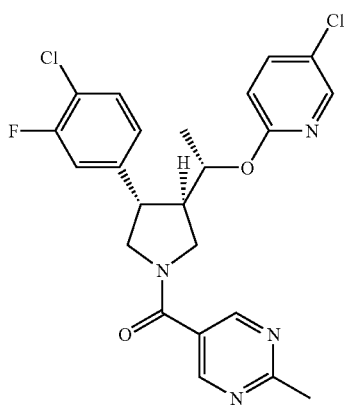

Coupling according to general procedure I:
Pyrrolidine intermediate: 5-Chloro-2-{(S)-1-[(3R,4S)-4-(4-chloro-3-fluoro-phenyl)-pyrrolidin-3-yl]-ethoxy}-pyridine (XII-B-9)
Carboxylic acid: 2-Methyl-pyrimidine-5-carboxylic acid (commercially available), ES-MS m/e: 475.3 (M+H$^+$).

EXAMPLE 91

6-{(S)-1-[(3R,4S)-4-(4-Chloro-3-fluoro-phenyl)-1-(2-methyl-pyrimidine-5-carbonyl)-pyrrolidin-3-yl]-ethoxy}-nicotinonitrile

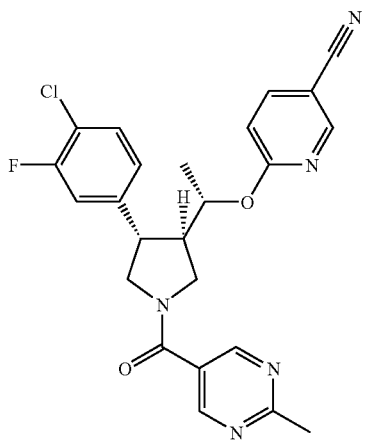

Coupling according to general procedure I:
Pyrrolidine intermediate: 6-{(S)-1-[(3R,4S)-4-(4-Chloro-3-fluoro-phenyl)-pyrrolidin-3-yl]-ethoxy}-nicotinonitrile (XII-B-10)
Carboxylic acid: 2-Methyl-pyrimidine-5-carboxylic acid (commercially available),
ES-MS m/e: 466.2 (M+H$^+$).

EXAMPLE 92

6-{(SR)-1-[(3RS,4SR)-4-(3,4-Dichloro-phenyl)-1-(4-methyl-pyridine-2-carbonyl)-pyrrolidin-3-yl]-ethoxy}-nicotinonitrile

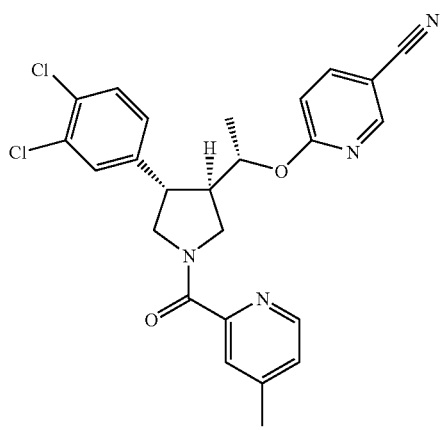

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 4-Methyl-pyridine-2-carboxylic acid (commercially available), ES-MS m/e: 481.1 (M+H$^+$).

EXAMPLE 93

6-{(SR)-1-[(3RS,4SR)-4-(3,4-Dichloro-phenyl)-1-(6-methyl-pyridine-2-carbonyl)-pyrrolidin-3-yl]-ethoxy}-nicotinonitrile

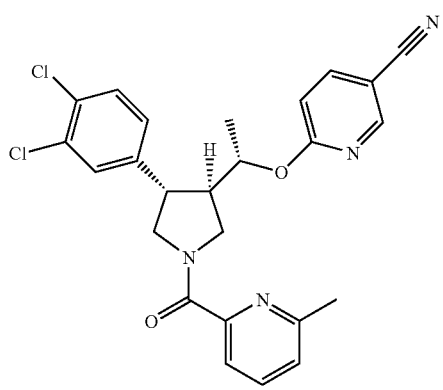

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 6-Methyl-pyridine-2-carboxylic acid (commercially available), ES-MS m/e: 481.2 (M+H⁺).

EXAMPLE 94

6-{(SR)-1-[(3RS,4SR)-4-(3,4-Dichloro-phenyl)-1-(pyrimidine-4-carbonyl)-pyrrolidin-3-yl]-ethoxy}-nicotinonitrile

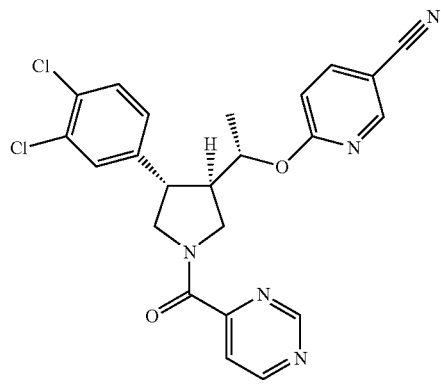

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: Pyrimidine-4-carboxylic acid (commercially available), ES-MS m/e: 468.1 M+H⁺).

EXAMPLE 95

6-{(SR)1-1[-(3RS,4SR)-4-(3,4-Dichloro-phenyl)-1-(2-methyl-pyrimidine-4-carbonyl)-pyrrolidin-3-yl]-ethoxy}-nicotinonitrile

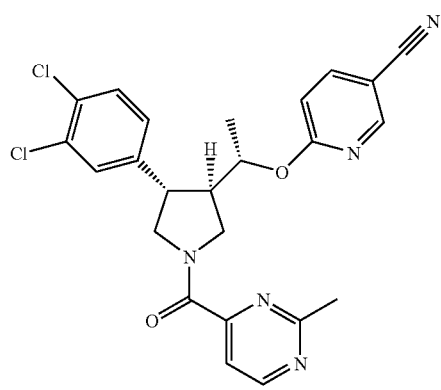

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 2-Methyl-pyrimidine-4-carboxylic acid (commercially available), ES-MS m/e: 482.2 (M+H⁺).

EXAMPLE 96

6-{(SR)-1-[(3RS,4SR)-4-(3,4-Dichloro-phenyl)-1-(pyrazine-2-carbonyl)-pyrrolidin-3-yl]-ethoxy}-nicotinonitrile

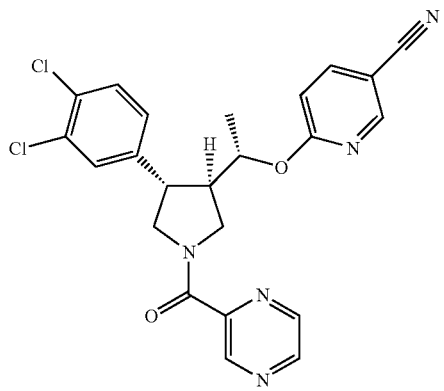

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: Pyrazine-2-carboxylic acid (commercially available), ES-MS m/e: 468.3 (M+H⁺).

EXAMPLE 97

6-{(SR)-1-[(3RS,4SR)-4-(3,4-Dichloro-phenyl)-1-(5-methyl-pyrazine-2-carbonyl)-pyrrolidin-3-yl]-ethoxy}-nicotinonitrile

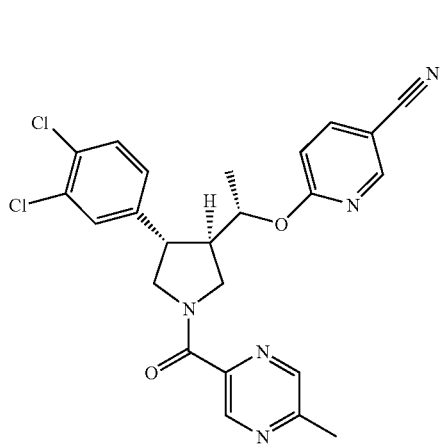

Coupling according to general procedure I:

Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)

Carboxylic acid: 5-Methyl-pyrazine-2-carboxylic (commercially available), ES-MS m/e: 482.3 (M+H⁺).

EXAMPLE 98

6-{(SR)-1-[(3RS,4SR)-1-(2-tert-Butyl-pyrimidine-5-carbonyl)-4-(3,4-dichloro-phenyl)-pyrrolidin-3-yl]-ethoxy}-nicotinonitrile

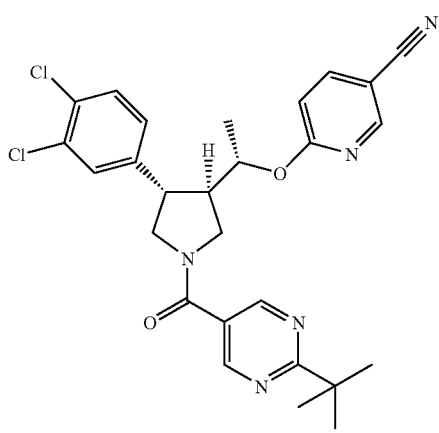

Coupling according to general procedure I:
Pyrrolidine intermediate: 6-{(SR)-1-[(3RS,4SR)-4-(3,4-Dichloro-phenyl)-pyrrolidin-3-yl]-ethoxy}-nicotinonitrile (XII-B-3)
Carboxylic acid: 2-tert-Butyl-pyrimidine-5-carboxylic acid (commercially available), ES-MS m/e: 524.2 (M+H⁺).

EXAMPLE 99

6-{(SR)-1[-(3RS,4SR)-4-(3,4-Dichloro-phenyl)-1-(2-methyl-pyrimidine-5-carbonyl)-pyrrolidin-3-yl]-propoxy}-nicotinonitrile

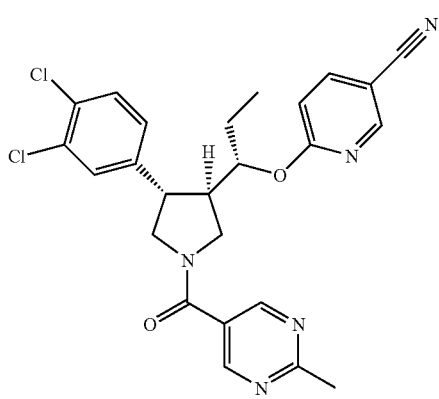

a) 1-[(3RS,4SR)-1-Benzyl-4-(3,4-dichloro-phenyl)-pyrrolidin-3-yl]-propan-1-one

To a solution of (3RS,4SR)-1-benzyl-4-(3,4-dichloro-phenyl)-pyrrolidine-3-carboxylic acid methoxy-methyl-amide (described herein above) 377 mg (0.959 mmol) dissolved in THF (4 mL) was added 0.676 mL (1.15 mmol) of ethyllithium (1.7M in dibutylether) dropwise at −78° C. and stirred for one hour. The reaction was quenched by aq. ammonium chloride solution and extracted with ethylacetate. The separated organic layer was dired on anhydrous sodium sulfate and concentrated in vaccuo. The residue was purified by silica gel column chromatography eluted by a mixture of heptane and ethyl acetate (10:1) yielding 212 mg (61%) of the title compound as a light yellow oil. ES-MS m/e: 362.2 (M+H⁺).

b) (RS)-1-[(3RS,4SR)-1-Benzyl-4-(3,4-dichloro-phenyl)1-pyrrolidin-3-yl]-propan-1-ol and (SR)-1-[(3RS,4SR)-1-Benzyl-4-(3,4-dichloro-phenyl)-pyrrolidin-3-yl]-propan-1-ol To a solution of 1-[(3RS,4SR)-1-benzyl-4-(3,4-dichloro-phenyl)-pyrrolidin-3-yl]-propan-1-one (211 mg, 0.5825 mmol) in THF (5 mL) was added LAH (1M in THF, 0.58 mL, 0.58 mmol) at 0° C. and stirred for 30 minutes. The reaction was quenched by an addition of aq. KF solution (135 mg in 0.5 mL of water). The mixture was stirred vigorously for 10 minutes followed by an addition of anhydrous sodium sulfate. The insoluves were removed by filtration through a cotton pad and the cake was washed with ethyl acetate. The filtrate was concentrated in vacuo and the residue was purified by silica gel column chromatography (heptane/ethyl acetate 3:1 to 1:1) yielding (RS)-1-[(3RS,4SR)-1-benzyl-4-(3,4-dichloro-phenyl)-pyrrolidin-3-yl]-propan-1-ol as a light yellow oil with ES-MS m/e: 364.1 (M'H⁺⁾ and ⁽SR⁾-1-[(3RS,4SR)-1-benzyl-4-(3,4-dichloro-phenyl)-pyrrolidin-3-yl]-propan-1-ol as a light yellow oil. ES-MS m/e: 364.1 (M+H⁺).

c) 6-{(SR)-1-[(3RS,4SR)-1-Benzyl-4-(3,4-dichloro-phenyl)-pyrrolidin-3-yl]-propoxy}-nicotinonitrile To a solution of (SR)-1-[(3RS,4SR)-1-benzyl-4-(3,4-dichloro-phenyl)-pyrrolidin-3-yl]-propan-1-ol (15.2 mg, 0.0417 mmol) and 6-chloro-nicotinonitrile (7 mg, 0.05 mmol) in 1 mL of DMF was added sodium hydride (60%, 10 mg, 0.25 mmol) at room temperature. The mixture was stirred over night and quenched by an addition of aq. ammonium chloride solution. The mixture was extracted with ethyl acetate and the separated organic layer was washed with water two times and brine subsequently.

The organic phase was dried over anhydrous sodium sulfate and concentrated in vaccuo after filtration. The residue was purified by TLC (heptane/ethyl acetate 2:1) yielding the title compound(12.4 mg, 64% yield) as a light yellow oil. ES-MS m/e: 466.1 (M+H⁺).

d) 6-{(SR)-1-[(3RS,4SR)-4-(3,4-Dichloro-phenyl)-pyrrolidin-3-yl]-propoxy}-nicotinonitrile The titled compound was obtained as a light yellow oil following the general procedure IV for debenzylation. ES-MS m/e: 376.1 (M+H⁺).

e) 6-{(SR)-1-[(3RS,4SR)-4-(3,4-Dichloro-phenyl)-1-(2-methyl-pyrimidine-5-carbonyl)-pyrrolidin-3-yl]-propoxy}-nicotinonitrile The titled compound was obtained as a light yellow oil following a general procedure I for amidation between 6-{(SR)-1-[(3RS,4SR)-4-(3,4-dichloro-phenyl)-pyrrolidin-3- yl]-propoxy}-nicotinonitrile and 2-methyl-pyrimidine-5-carboxylic acid. ES-MS m/e: 496.3 (M+H⁺).

EXAMPLE 100

6-{(RS)-1-[(3RS,4SR)-4-(3,4-Dichloro-phenyl)-1-(2-methyl-pyrimidine-5-carbonyl)-pyrrolidin-3-yl]-propoxy}-nicotinonitrile

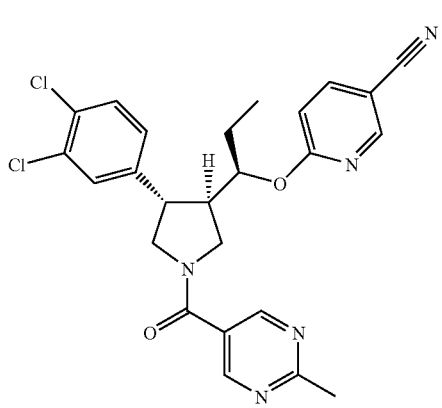

a) 6-{(RS)-1-[(3RS,4SR)-1-Benzyl-4-(3,4-dichloro-phenyl)-pyrrolidin-3-yl]-propoxy}-nicotinonitrile To a solution of (RS)-1-[(3RS,4SR)-1-benzyl-4-(3,4-dichloro-phenyl)-pyrrolidin-3-yl]-propan-1-ol (described herein above) (21.0 mg, 0.0576 mmol) and 6-chloro-nicotinonitrile (9.6 mg, 0.069 mmol) in 1 mL of DMF was added sodium hydride (60%, 10 mg, 0.25 mmol) at room temperature. The mixture was stirred over night and quenched by an addition of aq. ammonium chloride solution. The mixture was extracted with ethyl acetate and the separated organic layer was washed with water two times and brine subsequently. The organic phase was dried over anhydrous sodium sulfate and concentrated in vaccuo after filtration. The residue was purified by TLC (heptane/ethyl acetate 2:1) yielding the titled compound(19.6 mg, 73% yield) as a light yellow oil. ES-MS m/e: 466.1 (M+H⁺).

b) 6-{(RS)-1-[(3RS,4SR)-4-(3,4-Dichloro-phenyl)1-pyrrolidin-3-yl]-propoxy}-nicotinonitrile The titled compound was obtained as a light yellow oil following a general procedure IV for debenzylation. ES-MS m/e: 376.1 (M+H⁺).

c) 6-{(RS)-1-[(3RS,4SR)-4-(3,4-Dichloro-phenyl)-1-(2-methyl-pyrimidine-5-carbonyl)-pyrrolidin-3-yl]-propoxy}-nicotinonitrile The titled compound was obtained as a light yellow oil following the general procedure I for amidation between 6-{(RS)-1-[(3RS,4SR)-4-(3,4-dichloro-phenyl)-pyrrolidin-3-yl]-propoxy}-nicotinonitrile and 2-methyl-pyrimidine-5-carboxylic acid. ES-MS m/e: 496.3 (M+H⁺).

EXAMPLE 101

{(3S,4R)-3-(3-Chloro-4-fluoro-phenyl)-4-[(S)-1-(5-chloro-pyridin-2-yloxy)-ethyl]-pyrrolidin-1-yl}-(2-methyl-pyrimidin-5-yl)-methanone

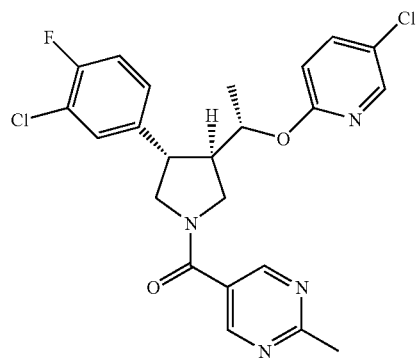

Coupling according to general procedure I:
Pyrrolidine intermediate: 5-Chloro-2-{(S)-1-[(3R,4S)-4-(3-chloro-4-fluoro-phenyl)-pyrrolidin-3-yl]-ethoxy}-pyridine (XII-B-5)
Carboxylic acid: 2-Methyl-pyrimidine-5-carboxylic acid (commercially available),
ES-MS m/e: 475.1 (M+H⁺).

EXAMPLE 102

6-{(S)-1-[(3R,4S)-4-(3-Chloro-4-fluoro-phenyl)-1-(2-methyl-pyrimidine-5-carbonyl)-pyrrolidin-3-yl]-ethoxy}-nicotinonitrile

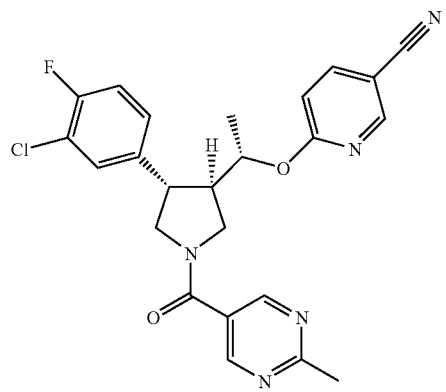

Coupling according to general procedure I:
Pyrrolidine intermediate: 6-{(S)-1-[(3R,4S)-4-(3-Chloro-4-fluoro-phenyl)-pyrrolidin-3-yl]-ethoxy}-nicotinonitrile (XII-B-6)
Carboxylic acid: 2-Methyl-pyrimidine-5-carboxylic acid (commercially available),
ES-MS m/e: 466.2 (M+H⁺).

EXAMPLE 103

[(3R,4S)-3-[(S)-1-(5-Chloro-pyridin-2-yloxy)-ethyl]-4-(3,4-difluoro-phenyl)-pyrrolidin-1-yl]-(2-methyl-pyrimidin-5-yl)-methanone

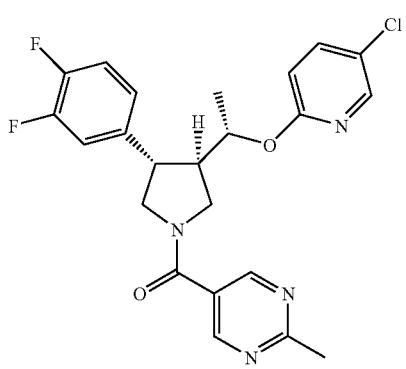

Coupling according to general procedure I:
Pyrrolidine intermediate: 5-Chloro-2-{(S)-1-[(3R,4S)-4-(3,4-difluoro-phenyl)-pyrrolidin-3-yl]-ethoxy}-pyridine (XII-B-7)
Carboxylic acid: 2-Methyl-pyrimidine-5-carboxylic acid (commercially available),
ES-MS m/e: 459.2 (M+H$^+$).

EXAMPLE 104

[(3R,4S)-3-[(S)-1-(5-Chloro-pyridin-2-yloxy)-ethyl]-4-(3,4-difluoro-phenyl)-pyrrolidin-1-yl]-(6-methyl-pyridazin-4-yl)-methanone

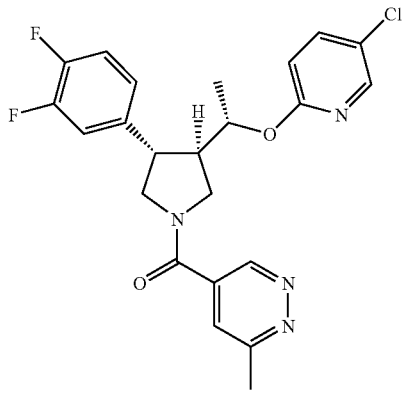

Coupling according to general procedure I:
Pyrrolidine intermediate: 5-Chloro-2-{(S)-1-[(3R,4S)-4-(3,4-difluoro-phenyl)-pyrrolidin-3-yl]-ethoxy}-pyridine (XII-B-7)
Carboxylic acid: 6-Methyl-pyridazine-4-carboxylic acid (described herein above),
ES-MS m/e: 459.3 (M+H$^+$).

EXAMPLE 105

6-{(S)-1-[(3R,4S)-4-(3,4-Difluoro-phenyl)-1-(2-methyl-pyrimidine-5-carbonyl)-pyrrolidin-3-yl]-ethoxy}-nicotinonitrile

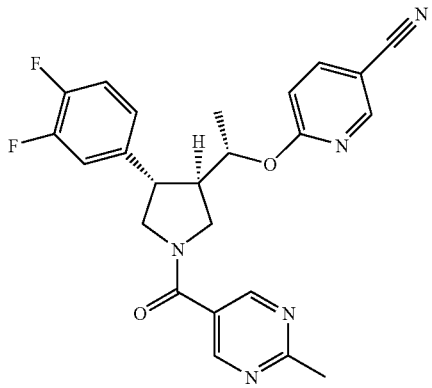

Coupling according to general procedure I:
Pyrrolidine intermediate: 6-{(S)-1-[(3R,4S)-4-(3,4-Difluoro-phenyl)-pyrrolidin-3-yl]-ethoxy}-nicotinonitrile (XII-B-8)
Carboxylic acid: 2-Methyl-pyrimidine-5-carboxylic acid (commercially available),
ES-MS m/e: 450.2 (M+H$^+$).

EXAMPLE 106

6-{(S)-1-[(3R,4S)-4-(3,4-Difluoro-phenyl)-1-(6-methyl-pyridazine-4-carbonyl)-pyrrolidin-3-yl]-ethoxy}-nicotinonitrile

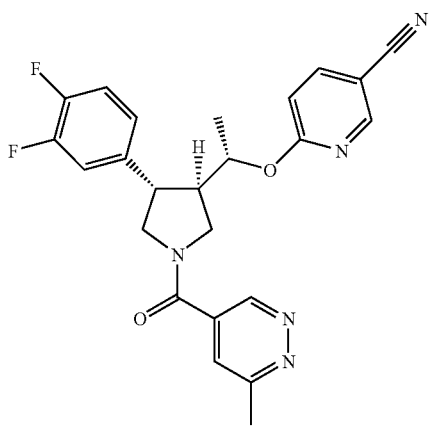

Coupling according to general procedure I:
Pyrrolidine intermediate: 6-{(S)-1-[(3R,4S)-4-(3,4-Difluoro-phenyl)-pyrrolidin-3-yl]-ethoxy}-nicotinonitrile (XII-B-8)
Carboxylic acid: 6-Methyl-pyridazine-4-carboxylic acid (described herein above),
ES-MS m/e: 450.1 (M+H$^+$).

EXAMPLE 107

{(3S,4R)-3-(4-Chloro-3-fluoro-phenyl)-4-[(S)-1-(5-chloro-pyridin-2-yloxy)-ethyl]-pyrrolidin-1-yl}-(6-methyl-pyridazin-4-yl)-methanone

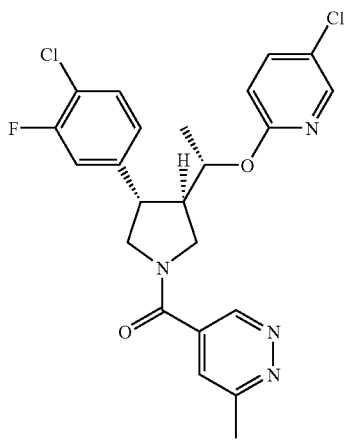

Coupling according to general procedure I:
Pyrrolidine intermediate: 5-Chloro-2-{(S)-1-[(3R,4S)-4-(4-chloro-3-fluoro-phenyl)-pyrrolidin-3-yl]-ethoxy}-pyridine (XII-B-9)
Carboxylic acid: 6-Methyl-pyridazine-4-carboxylic acid (described herein above),
ES-MS m/e: 475.0 (M+H$^+$).

EXAMPLE 108

{(3S,4R)-3-(4-Chloro-phenyl)-4-[(S)-1-(5-chloro-pyridin-2-yloxy)-ethyl]-pyrrolidin-1-yl}-(6-methyl-pyridazin-4-yl)-methanone

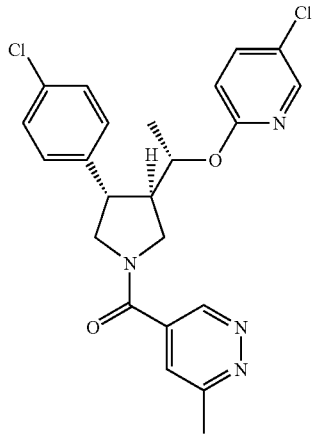

Coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (XII-B-11)
Carboxylic acid: 6-Methyl-pyridazine-4-carboxylic acid (described herein above),
ES-MS m/e: 457.2 (M+H$^+$).

EXAMPLE 109

{(3S,4R)-3-(4-Chloro-phenyl)-4-[(S)-1-(5-chloro-pyridin-2-yloxy)-ethyl]-pyrrolidin-1-yl}-(2-methyl-pyrimidin-5-yl)-methanone

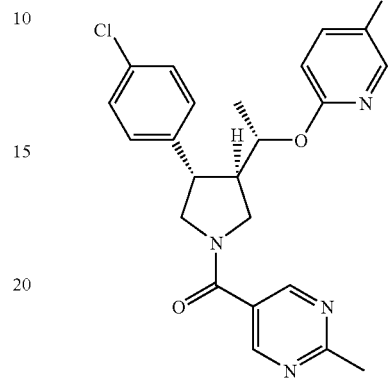

Coupling according to general procedure I:
Pyrrolidine intermediate: 5-Chloro-2-{(S)-1-[(3R,4S)-4-(4-chloro-phenyl)-pyrrolidin-3-yl]-ethoxy}-pyridine (XII-B-11)
Carboxylic acid: 2-Methyl-pyrimidine-5-carboxylic acid (commercially available),
ES-MS m/e: 457.3 (M+H$^+$).

EXAMPLE 110

{(3SR,4RS)-3-(3,4-Dichloro-phenyl)-4-[(SR)-1-(5-ethynyl-pyridin-2-yloxy)-ethyl]-pyrrolidin-1-yl}-(6-methyl-pyridazin-4-yl)-methanone

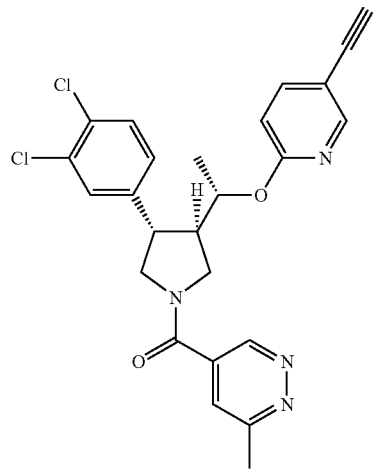

a) 2-{(SR)-1-[(3RS,4SR)-1-Benzyl-4-(3,4-dichloro-phenyl)-pyrrolidin-3-yl]-ethoxy}-5-bromo-pyridine The titled compound was obtained as a light yellow oil following a general procedure for Mitsunobu reaction between (SR)-1-[(3SR,4RS)-1-benzyl-4-(3,4-dichloro-phenyl)-pyrrolidin-3-yl]-ethanol (described herein above) and 5-bromo-pyridin-2-ol. ES-MS m/e: 507.0 (M+H⁺).

b) 2-{(SR)-1-[(3RS,4SR)-1-Benzyl-4-(3,4-dichloro-phenyl)-pyrrolidin-3-yl]-ethoxy}-5-trimethylsilanyl-ethynyl-pyridine To a suspension of 2-{(SR)-1-[(3RS,4SR)-1-benzyl-4-(3,4-dichloro-phenyl)-pyrrolidin-3-yl]-ethoxy}-5-bromo-pyridine (128 mg, 0.253 mmol) and bis(triphenylphosphine) palladium(II) chloride (53 mg, 0.076 mmol) and triphenylphosphine (16.6 mg, 0.0632 mmol) and CuI (11 mg, 0.0578 mmol) in THF (3 mL) and diethylamine (1.5 mL) was added ethynyltrimethylsilane (0.108 mL, 0.759 mmol) under Ar. The mixture was heated at 85° C. over night. The reaction mixture was diluted with ethyl acetate and washed with aq.ammonium chloride solution two times. The separated organic phase was dried over anhydrous sodium sulfate and concentrated in vaccuo after filtration. The residue was purified by silica gel column chromatography (DCM) yielding 89.5 mg (68%) of the titled compound as a light yellow oil. ES-MS m/e: 523.3 (M+H⁺).

c) 2-{(SR)-1-[(3RS,4SR)-4-(3,4-Dichloro-phenyl)-pyrrolidin-3-yl]-ethoxy}-5-ethynyl-pyridine The titled compound was obtained as a light yellow oil following a general procedure IV for debenzylation reaction. Concomitant desylilation took place. ES-MS m/e: 361.1 (M+H⁺).

d) {(3SR,4RS)-3-(3,4-Dichloro-phenyl)-4-[(SR)-1-(5-ethynyl-pyridin-2-yloxy)-ethyl]-pyrrolidin-1-yl}-(6-methyl-pyridazin-4-yl)-methanone The titled compound was obtained as a white foam following a general I procedure for amidation reaction between 2-{(SR)-1-[(3RS,4SR)-4-(3,4-dichloro-phenyl)-pyrrolidin-3-yl]-ethoxy}-5-ethynyl-pyridine and 6-methyl-pyridazine-4-carboxylic acid. ES-MS m/e: 481.2 (M+H⁺).

EXAMPLE 111

6-{(S)-1-[(3R,4S)-4-(4-Chloro-phenyl)-1-(6-methyl-pyridazine-4-carbonyl)-pyrrolidin-3-yl]-ethoxy}-nicotinonitrile

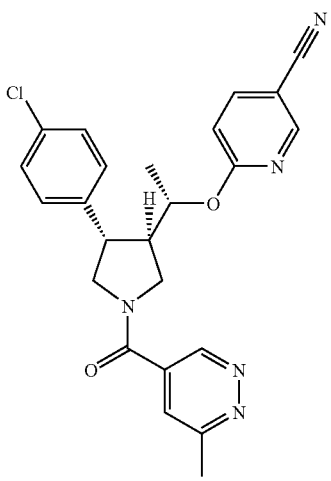

Coupling according to general procedure I:
Pyrrolidine intermediate: 6-{(S)-1-[(3R,4S)-4-(4-Chloro-phenyl)-pyrrolidin-3-yl]-ethoxy}-nicotinonitrile (XII-B-12)
Carboxylic acid: 6-Methyl-pyridazine-4-carboxylic acid (described herein above),
ES-MS m/e: 448.1 (M+H⁺).

EXAMPLE 112

[(3R,4S)-3-[(R)-1-(5-Chloro-pyridin-2-yloxy)-2-hydroxy-ethyl]-4-(3,4-dichloro-phenyl)-pyrrolidin-1-yl]-(6-methyl-pyridazin-4-yl)-methanone

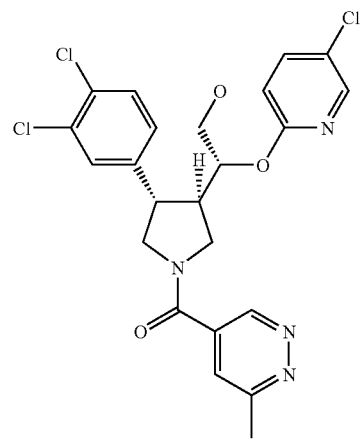

a) (S)-4-Benzyl-3-[(3R,4S)-1-benzyl-4-(3,4-dichloro-phenyl)-pyrrolidine-3-carbonyl]-oxazolidin-2-one and (S)-4-Benzyl-3-[(3S,4R)-1-benzyl-4-(3,4-dichloro-phenyl)-pyrrolidine-3-carbonyl]-oxazolidin-2-one To a solution of (3RS,4SR)-1-benzyl-4-(3,4-dichloro-phenyl)-pyrrolidine-3-carboxylic acid (described herein above) (13.39 g, 0.038 mol) in THF (200 mL) at −20° C. were added triethylamine (13.32 mL, 0.096 mol) and pivaloyl chloride (11.76 mL, 0.096 mol) subsequently. Stirring was continued for two hours at the same temperature, and to this mixture were added (S)-4-benzyl-oxazolidin-2-one (8.13 g, 0.046 mol) and lithium chloride (1.94 g, 0.046 mol). The reaction mixture was gradually warmed to room temperature and stirred overnight. The reaction mixture was diluted with ethyl acetate and washed with water two times and saturated sodiumbicarbonate. The separated organic phase was dried on Na₂SO₄ and concentrated under vacuo. The two diastereoisomeres were separated by column chromatography (SiO₂, EtOAc/H, 1:2) to yield (S)-4-benzyl-3-[(3R,4S)-1-benzyl-4-(3,4-dichloro-phenyl)-pyrrolidine-3-carbonyl]-oxazolidin-2-one 9.47 g (49%) as a white solid ES-MS m/e: 509.3 (M+H⁺) and (S)-4-benzyl-3-[(3S,4R)-1-benzyl-4-(3,4-dichloro-phenyl)-pyrrolidine-3-carbonyl]-oxazolidin-2-one 9.40 g (48%) as a white solid ES-MS m/e: 509.3 (M+H⁺).

b) (3R,4S)-1-Benzyl-4-(3,4-dichloro-phenyl)-pyrrolidine-3-carboxylic acid methoxy-methyl-amide To a suspension of N,O-dimethylhydroxylamine hydrochloride (3.61 g, 0.037 mol) in DCM (40 mL) at RT was added trimethylaluminium (2.0M solution in heptane, 18.5 ml, 0.037 mol) dropwise and stirring was continued for one hour. To this mixture was added a solution of (S)-4-benzyl-3-[(3R,4S)-1-benzyl-4-(3,4-dichloro-phenyl)-pyrrolidine-3-carbonyl]-oxazolidin-2-one (9.47 g, 0.0186 mol) in DCM (50 mL) over 10 minutes. Stirring was continued for three hours. The reaction was quenched by an addition of aq. Potassium sodium tartarate solution and extracted with ethyl acetate. The separated organic layer was washed with brine and dried on $Na_2SO_4$ and concentrated under vacuo. Purification by column chromatography ($SiO_2$, EtOAc/H, 2:3) yielded 6.58 g (90%) of the title compound as a light yellow oil. ES-MS m/e: 393.1 $(M+H^+)$.

c) (3R,4S)-1-Benzyl-4-(3,4-dichloro-phenyl)-pyrrolidine-3-carbaldehyde

To a solution of (3R,4S)-1-benzyl-4-(3,4-dichloro-phenyl)-pyrrolidine-3-carboxylic acid methoxy-methyl-amide 6.58 g (0.017 mol) dissolved in THF (100 mL) was added 16 mL (0.017 mol) of lithiumaluminiumhydride (1.0M in THF) dropwise at 0° C. and stirred for one hour. The reaction was quenched by aq. ammonium chloride solution and extracted with ethylacetate twice. The combined organic layers were dired on anhydrous sodium sulfate and concentrated in vaccuo. The residue was purified by silica gel column chromatography eluted by a mixture of heptane and ethyl acetate (3:2) yielding 5.21 g (93%) of the title compound as a light yellow oil. ES-MS m/e: 334.2 $(M+H^+)$. compound as a light yellow oil. ES-MS m/e: 393.1 $(M+H^+)$.

d) (3S,4R)-1-Benzyl-3-(3,4-dichloro-phenyl)-4-vinyl-pyrrolidine

To a suspension of methyltriphenylphosphonium iodide (5.53 g, 0.0136 mol) in THF (50 mL) was added n-BuLi (1.6N in heptane, 6.5 mL, 0.0104 mol) dropwise at 0° C. and stirred for one hour. To this reaction mixture was added a solution of (3R,4S)-1-benzyl-4-(3,4-dichloro-phenyl)-pyrrolidine-3-carbaldehyde 2.68 g (0.008 mol) in THF (15 mL) dropwise at 0° C. and stirred for another one hour. The reaction was quenched by aq. ammonium chloride solution and extracted with ethylacetate. The separated organic layer was dired on anhydrous sodium sulfate and concentrated in vaccuo. The residue was purified by silica gel column chromatography eluted by a mixture of heptane and ethyl acetate (4:1) yielding 2.12 g (80%) of the title compound as a light yellow oil. ES-MS m/e: 332.1 $(M+H^+)$.

f) (S)-1-[(3R,4S)-1-Benzyl-4-(3,4-dichloro-phenyl)-pyrrolidin-3-yl]-2-(tert-butyl-dimethyl-silanyloxy)-ethanol $(DHQ)_2PHAL$ (452 mg, 0.6 mmol) was dissolved in MeCN (20 mL), t-BuOH (28 mL) and water (12 mL). To the solution was added $OsO_4$ (73 mg, 0.3 mmol) and the resulted mixture was stirred for 30 minutes. To the solution were added NMO (aq. 50% solution, 1.47 mL, 7 mmol) and (3S, 4R)-1-benzyl-3-(3,4-dichloro-phenyl)-4-vinyl-pyrrolidine (1.93 g, 5.8 mmol) as a solution of MeCN (20 mL) at room temperature. The whole mixture was vigorously stirred for 80 minutes. The reaction was quenched by an addition of sat. aq. $Na_2SO_3$ solution (10ml). The mixture was then concentrated in vaccuo, followed by dilution with AcOEt, and washed with brine. The separated aqueous phase was extracted with AcOEt twice. The combined organic phases were dried over $Na_2SO_4$. The residue was purified by silica gel column chromatography eluted by DCM to aceton yielding 1.85 g of a mixture of the diols as a light yellow oil. ES-MS m/e: 366.0 $(M+H^+)$.

The residue was dissolved in DCM (30 mL) followed by additions of TBDMSCl (915 mg, 6 mmol), Hunig base (1.29 mL, 8 mmol) and DMAP (124 mg) subsequently at room temperature, and the resulted mixture was stirred overnight. The reaction mixture was diluted with ethyl acetate and washed with aq. ammonium chloride solution three times. The separated organic phase was dried over sodium sulfate and concentrated in vaccuo after filtration. The residue was purified by silica gel column chromatography eluted with a mixture of heptane and ethyl acetate (4:1 to 3:1) yielding 1.64 g (67%) of the title compound as a light brown oil. ES-MS m/e: 480.2 $(M+H^+)$.

g) 2-[(R)-1-[(3R,4S)-1-Benzyl-4-(3,4-dichloro-phenyl)-pyrrolidin-3-yl]-2-(tert-butyl-dimethyl-silanyloxy)-ethoxy]-5-chloro-pyridine (S)-1-[(3R,4S)-1-Benzyl-4-(3,4-dichloro-phenyl)-pyrrolidin-3-yl]-2-(tert-butyl-dimethyl-silanyloxy)-ethanol (17) and $PPh_3$ ($PPh_3$ polymer bound, 3 mmol $PPh_3$/g resin) (614 mg, 1.87 mmol) were suspended in THF (10 mL). To the mixture were added 5-chloro-pyridin-2-ol (0.243 g, 1.87 mmol) and then DBAD (0.431 g, 1.87 mmol). The reaction mixture was stirred at 45° C. over night. The mixture was diluted with ethyl acetate and filtered on celite and concentrated under vacuo. The residue was purified by column chromatography ($SiO_2$, EtOAc/H, 1:15) yielded 571 mg (77%) of the title compound as a colorless oil. ES-MS m/e: 593.3 $(M+H^+)$.

h) 2-{(R)-2-(tert-Butyl-dimethyl-silanyloxy)-1-[(3R,4S)-4-(3,4-dichloro-phenyl)-pyrrolidin-3-yl]-ethoxy}-5-chloro-pyridine To a solution of 2-[(R)-1-[(3R,4S)-1-benzyl-4-(3,4-dichloro-phenyl)-pyrrolidin-3-yl]-2-(tert-butyl-dimethyl-silanyloxy)-ethoxy]-5-chloro-pyridine 570 mg (0.96 mmol) dissolved in toluene (4 mL) was added 0.31 mL (2.89 mmol) of 1-chloroethyl chloroformate and 0.491 mL (2.89 mmol) of Hunig base subsequently, and the mixture was heated at 100° C. for 40 minutes, then concentrated in vaccuo. The residue was dissolved in methanol (5 mL) and stirred at room temperature over night. The mixture was concentrated in vaccuo and diluted with ethyl acetate, then washed with aq. sodium bicarbonate solution twice. The separated organic layer was dried over sodium sulfate and concentrated in vaccuo after filtration yielded 0.40 g (83%) of the title compound as a light brown oil. ES-MS m/e: 501.2 $(M+H^+)$.

i) [(3R,4S)-3-[(R)-2-(tert-Butyl-dimethyl-silanyloxy)-1-(5-chloro-pyridin-2-yloxy)-ethyl]-4-(3,4-dichloro-phenyl)-pyrrolidin-1-yl]-(6-methyl-pyridazin-4-yl)-methanone To a solution of 2-{(R)-2-(tert-butyl-dimethyl-silanyloxy)-1-[(3R,4S)-4-(3,4-dichloro-phenyl)-pyrrolidin-3-yl]-ethoxy}-5-chloro-pyridine (220 mg) in DMF (12 mL) at −20° C. were added Hunig base (0.132 mL, 0.78 mmol) and then HATU (202 mg) and then 6-methyl-pyridazine-4-carboxylic acid (0.78 mmol, described herein above). The mixture was diluted with ethyl acetate and washed with aq.ammonium chloride solution three times and aq. sodium bicarbonate solution. The separated organic phase was dried over sodium sulfate and concentrated in vaccuo after filtration. The residue was purified by TLC (SiO$_2$, MeOH/DCM, 1:10) yielded 74 mg (27%) of the title compound as a light yellow oil. ES-MS m/e: 623.3 (M+H$^+$).

j) [(3R,4S)-3-[(R)-1-(5-Chloro-pyridin-2-yloxy)-2-hydroxy-ethyl]-4-(3,4-dichloro-phenyl)-pyrrolidin-1-yl]-(2-methyl-pyrimidin-5-yl)-methanone To a solution of [(3R,4S)-3-[(R)-2-(tert-butyl-dimethyl-silanyloxy)-1-(5-chloro-pyridin-2-yloxy)-ethyl]-4-(3,4-dichloro-phenyl)-pyrrolidin-1-yl]-(6-methyl-pyridazin-4-yl)-methanone (0.074 g, 0.119 mmol) dissolved in THF (4 mL) was added 0.014 mL (0.24 mmol) of acetic acid and 0.119 mL of TBAF (1.0M in THF). The reaction mixture was stirred over night at room temperature. The mixture was diluted with ethyl acetate and washed with water and aq. sodium bicarbonate solution subsequently. The separated organic phase was dried over sodium sulfate and concentrated in vaccuo after filtration. The residue was purified by TLC (SiO$_2$, MeOH/DCM, 1:10) yielded 55 mg (91%) of the title compound as a light yellow oil. ES-MS m/e: 507.1 (M+H$^+$).

EXAMPLE 113

[(3R,4S)-3-[(S)-1-(5-Chloro-pyridin-2-yloxy)-ethyl]-4-(3,4-difluoro-phenyl)-pyrrolidin-1-yl]-(3,6-dimethyl-pyridazin-4-yl)-methanone

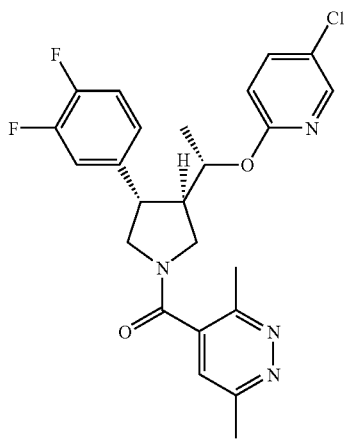

Coupling according to general procedure I:
Pyrrolidine intermediate: 5-Chloro-2-{(S)-1-[(3R,4S)-4-(3,4-difluoro-phenyl)-pyrrolidin-3-yl]-ethoxy}-pyridine (XII-B-7)

Carboxylic acid: 3,6-Dimethyl-pyridazine-4-carboxylic acid (prepared by hydrolysis of the commercially available ethyl ester), ES-MS m/e: 473.1 (M+H$^+$).

EXAMPLE 114

6-{(S)-1-[(3R,4S)-4-(3,4-Difluoro-phenyl)-1-(3,6-dimethyl-pyridazine-4-carbonyl)-pyrrolidin-3-yl]-ethoxy}-nicotinonitrile

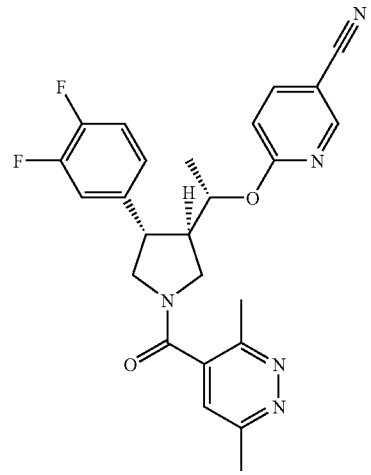

Coupling according to general procedure I:
Pyrrolidine intermediate: 6-{(S)-1-[(3R,4S)-4-(3,4-Difluoro-phenyl)-pyrrolidin-3-yl]-ethoxy}-nicotinonitrile (XII-B-8)
Carboxylic acid: 3,6-Dimethyl-pyridazine-4-carboxylic acid (prepared by hydrolysis of the commercially available ethyl ester), ES-MS m/e: 464.2 (M+H$^+$).

EXAMPLE 115

[(3R,4S)-3-[(S)-1-(5-Chloro-pyridin-2-yloxy)-ethyl]-4-(4-fluoro-phenyl)-pyrrolidin-1-yl]-(6-methyl-pyridazin-4-yl)-methanone

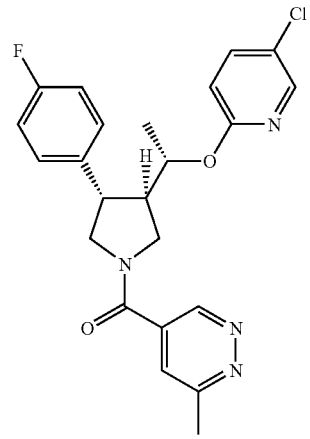

Coupling according to general procedure I:
Pyrrolidine intermediate: 5-Chloro-2-{(S)-1-[(3R,4S)-4-(4-fluoro-phenyl)-pyrrolidin-3-yl]-ethoxy}-pyridine (XII-B-13)
Carboxylic acid: 6-Methyl-pyridazine-4-carboxylic acid (described herein above),
ES-MS m/e: 441.2 (M+H⁺).

EXAMPLE 116

[(3R,4S)-3-[(R)-1-(5-Chloro-pyridin-2-yloxy)-2-hydroxy-ethyl]-4-(3,4-difluoro-phenyl)-pyrrolidin-1-yl]-(6-methyl-pyridazin-4-yl)-methanone

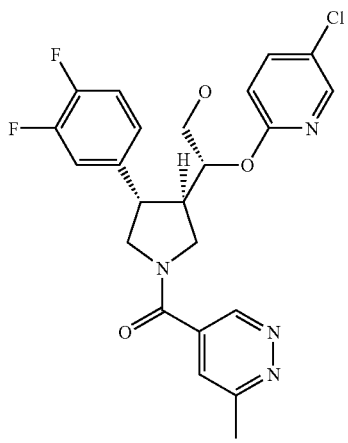

a) (3RS,4SR)-1-Benzyl-4-(3,4-difluoro-phenyl)-pyrrolidine-3-carboxylic acid

To a solution of N-(methoxymethyl)-N-(phenylmethyl)-N-(trimethylsilyl)methylamine (48.3 g, 204 mmol) and (E)-3-(3,4-difluoro-phenyl)-acrylic acid (15 g, 81.5 mmol) in THF (200 mL) was added trifluoroacetic acid (0.312 mL, 0.0041 mol) at 0° C. The mixture was gradually warmed to room temperature and stirred overnight. It was then concentrated in vaccuo and the residue was diluted with n-heptane (500 mL) followed by vigorous stirring for 1 hour. The resulted white precipitation was collected and washed with heptane affording 26 g (100%) of the title compound as a white solid. MS m/e: 318.1 (M+H⁺).

b) (S)-4-Benzyl-3-[(3R,4S)-1-benzyl-4-(3,4-difluoro-phenyl)-pyrrolidine-3-carbonyl]-oxazolidin-2-one To a solution of (3RS,4SR)-1-benzyl-4-(3,4-difluoro-phenyl)-pyrrolidine-3-carboxylic acid (25 g, 78.8 mmol) in THF (350 mL) at -20° C. were added triethylamine (27.45 mL, 197 mmol) and pivaloyl chloride (24.2 mL, 197 mmol) subsequently. Stirring was continued for two hours at the same temperature, and to this mixture were added (S)-4-Benzyl-oxazolidin-2-one (14.7 g, 82.7 mmol) and lithium chloride (3.67 g, 86.7 mmol). The reaction mixture was gradually warmed to room temperature and stirred overnight. The reaction mixture was diluted with ethyl acetate and washed with water two times and saturated sodiumbicarbonate. The separated organic phase was dried on Na₂SO₄ and concentrated under vacuo. The two diastereoisomeres were separated by column chromatography (SiO₂, EtOAc/H, 15:85) to yield (S)-4-benzyl-3-[(3R,4S)-1-benzyl-4-(3,4-difluoro-phenyl)-pyrrolidine-3-carbonyl]-oxazolidin-2-one 18 g (48%) as awhite solid. MS m/e: 477.1 (M+H⁺).

c) (3R,4S)-1-Benzyl-4-(3,4-difluoro-phenyl)-pyrrolidine-3-carboxylic acid methoxy-methyl-amide To a suspension of N,O-dimethylhydroxylamine hydrochloride (7.82 g, 80.6 mmol) in DCM (130 mL) at RT was added trimethylaluminium (2.0M solution in heptane, 40.3 ml, 80.6 mmol) dropwise and stirring was continued for one hour. To this mixture was added a solution of (S)-4-benzyl-3-[(3R,4S)-1-benzyl-4-(3,4-difluoro-phenyl)-pyrrolidine-3-carbonyl]-oxazolidin-2-one (19.2 g, 40.3 mmol) in DCM (100 mL) over 10 minutes. Stirring was continued for three hours. The reaction was quenched by an addition of aq. Potassium sodium tartarate solution and extracted with ethyl acetate. The separated organic layer was washed with brine and dried on Na₂SO₄ and concentrated under vacuo. Its purification by column chromatography (SiO₂, EtOAc/H, 15:85) yielded 13 g (90%) of the title compound as a light yellow oil. ES-MS m/e: 361.2 (M+H⁺).

d) (3R,4S)-1-Benzyl-4-(3,4-difluoro-phenyl)-pyrrolidine-3-carbaldehyde

To a solution of (3R,4S)-1-benzyl-4-(3,4-difluoro-phenyl)-pyrrolidine-3-carboxylic acid methoxy-methyl-amide 3.24 g (9 mmol) dissolved in THF (60 mL) was added 9 mL (9 mmol) of lithiumaluminiumhydride (1.0M in THF) dropwise at 0° C. and stirred for one hour. The reaction was quenched by aq. ammonium chloride solution and extracted with ethylacetate twice. The combined organic layers were dired on anhydrous sodium sulfate and concentrated in vaccuo. The residue was purified by silica gel column chromatography eluted by a mixture of heptane and ethyl acetate (3:2) yielding 2.7 g (99%) of the title compound as a light yellow oil. ES-MS m/e: 302.1 (M+H⁺).

e) (3S,4R)-1-Benzyl-3-(3,4-difluoro-phenyl)-4-vinyl-pyrrolidine

To a suspension of methyltriphenylphosphonium iodide (6.35 g, 15.6 mmol) in THF (60 mL) was added n-BuLi (1.6N in heptane, 7.4 mL, 0.0119 mol) dropwise at 0° C. and stirred for one hour. To this reaction mixture was added a solution of (3R,4S)-1-benzyl-4-(3,4-difluoro-phenyl)-pyrrolidine-3-carbaldehyde 2.77 g (9.2 mmol) in THF (15 mL) dropwise at 0° C. and stirred for another one hour. The reaction was quenched by aq. ammonium chloride solution and extracted with ethylacetate. The separated organic layer was dired on anhydrous sodium sulfate and concentrated in vaccuo. The residue was purified by silica gel column chromatography eluted by a mixture of heptane and ethyl acetate (7:3) yielding 1.7 g (62%) of the title compound as a light yellow oil ES-MS m/e: 300.1 (M+H⁺).

f) (S)-1-[(3R,4S)-1-Benzyl-4-(3,4-difluoro-phenyl)-pyrrolidin-3-yl]-2-(tert-butyl-dimethyl-silanyloxy)-ethanol (DHQ)₂PHAL (178 mg, 0.2 mmol) was dissolved in MeCN (20 mL), t-BuOH (28 mL) and water (12 mL). To the solution was added OsO₄ (29 mg, 0.114 mmol) and the resulted mixture was stirred for 30 minutes. To the solution were added NMO (aq. 50% solution, 1.44 mL, 7 mmol) and (3S,4R)-1-benzyl-3-(3,4-difluoro-phenyl)-4-vinyl-pyrrolidine (1.707 g, 6 mmol) as a solution of MeCN (20 mL) at room temperature. The whole mixture was vigorously stirred for 3 hours. The reaction was quenched by an addition of sat. aq. Na$_2$SO$_3$ solution (10 ml). The mixture was then concentrated in vaccuo, followed by dilution with AcOEt, and washed with brine. The separated aqueous phase was extracted with AcOEt twice. The combined organic phasese were dried over Na$_2$SO$_4$. The residue was purified by silica gel column chromatography eluted by DCM to aceton yielding 1.97 g of a mixture of the diols as a light yellow oil. ES-MS m/e: 334.2 (M+H$^+$).

The residue was dissolved in DCM (10 mL) followed by additions of TBDMSCl (1.247 g, 8 mmol), Hunig base (2 mL, 12 mmol) and DMAP (144 mg, 1 mmol) subsequently at room temperature, and the resulted mixture was stirred overnight. The reaction mixture was diluted with ethyl acetate and washed with aq. ammonium chloride solution three times. The separated organic phase was dried over sodium sulfate and concentrated in vaccuo after filtration. The residue was purified by silica gel column chromatography eluted with a mixture of heptane and ethyl acetate (4:1) yielding 1.49 g (56%) of the titled compound as a light yellow oil. ES-MS m/e: 448.3 (M+H$^+$).

g) 2-[(R)-1-[(3R,4S)-1-Benzyl-4-(3,4-difluoro-phenyl)-pyrrolidin-3-yl]-2-(tert-butyl-dimethyl-silanyloxy)-ethoxy]-5-chloro-pyridine The titled compound was prepared following the general procedure for Mitsunobu reaction using (S)-1-[(3R,4S)-1-benzyl-4-(3,4-difluoro-phenyl)-pyrrolidin-3-yl]-2-(tert-butyl-dimethyl-silanyloxy)-ethanol and 5-Chloro-pyridin-2-ol. ES-MS m/e: 559.2 (M+H$^+$).

h) 2-{(R)-2-(tert-Butyl-dimethyl-silanyloxy)-1-[(3R,4S)-4-(3,4-difluoro-phenyl)-pyridin-3-yl]-ethoxy}-5-chloro-pyridine The titled compound was prepared following a general procedure IV for debenzylation reaction. ES-MS m/e: 469.2 (M+H$^+$).

i) [(3R,4S)-3-[(R)-2-(tert-Butyl-dimethyl-silanyloxy)-1-(5-chloro-pyridin-2-yloxy)-ethyl]-4-(3,4-difluoro-phenyl)-pyrrolidin-1-yl]-(6-methyl-pyridazin-4-yl)-methanone The titled compound was prepared following a general procedure I for amidation between 2-{(R)-2-(tert-butyl-dimethyl-silanyloxy)-1-[(3R,4S)-4-(3,4-difluoro-phenyl)-pyrrolidin-3-yl]-ethoxy}-5-chloro-pyridine and 6-Methyl-pyridazine-4-carboxylic acid. ES-MS m/e: 589.1 (M+H$^+$).

j) [(3R,4S)-3-[(R)-1-(5-Chloro-pyridin-2-yloxy)-2-hydroxy-ethyl]-4-(3,4-difluoro-phenyl)-pyrrolidin-1-yl]-(2-methyl-pyrimidin-5-yl)-methanone To a solution of [(3R,4S)-3-[(R)-2-(tert-butyl-dimethyl-silanyloxy)-1-(5-chloro-pyridin-2-yloxy)-ethyl]-4-(3,4-difluoro-phenyl)-pyrrolidin-1-yl]-(6-methyl-pyridazin-4-yl)-methanone (0.050 g, 0.085 mmol) dissolved in THF (4 mL) was added 0.10 mL of TBAF (1.0M in THF). The reaction mixture was stirred over night at room temperature. The mixture was diluted with ethyl acetate and washed with water and aq. sodium bicarbonate solution subsequently. The separated organic phase was dried over sodium sulfate and concentrated in vaccuo after filtration. The residue was purified by TLC (SiO$_2$, MeOH/DCM, 1:10) yielded 40 mg (84%) of the title compound as a light yellow oil. ES-MS m/e: 475.1 (M+H$^+$).

EXAMPLE 117

[(3RS,4SR)-3-[(SR)-1-(5-Chloro-pyridin-2-yloxy)-ethyl]-4-(2,4-difluoro-phenyl)-pyrrolidin-1-yl]-(6-methyl-pyridazin-4-yl)-methanone

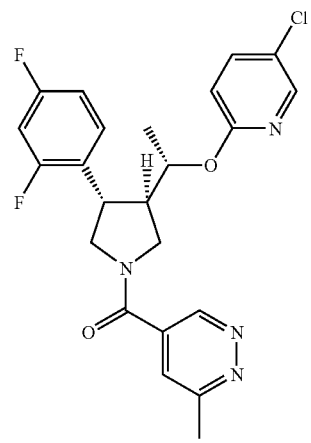

Coupling according to general procedure I:
Pyrrolidine intermediate: 5-Chloro-2-{(RS)-1-[(3SR,4RS)-4-(2,4-difluoro-phenyl)-pyrrolidin-3-yl]-ethoxy}-pyridine (XII-B-14)
Carboxylic acid: 6-Methyl-pyridazine-4-carboxylic acid (described herein above), ES-MS m/e: 459.3 (M+H$^+$).

EXAMPLE 118

[(3R,4S)-3-[(S)-1-(5-Chloro-pyridin-2-yloxy)-ethyl]-4-(2,4-difluoro-phenyl)-pyrrolidin-1-yl]-(2-methyl-pyrimidin-5-yl)-methanone

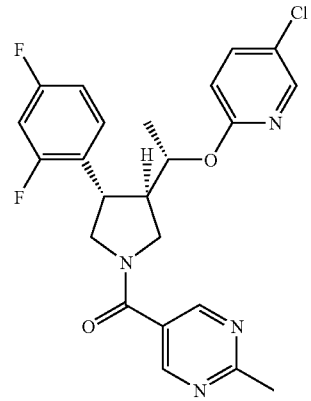

Coupling according to general procedure I:
Pyrrolidine intermediate: 5-Chloro-2-{(RS)-1-[(3SR,4RS)-4-(2,4-difluoro-phenyl)-pyrrolidin-3-yl]-ethoxy}-pyridine (XII-B-14)

Carboxylic acid: 2-Methyl-pyrimidine-5-carboxylic acid (commercially available),
ES-MS m/e: 459.3 (M+H+).

EXAMPLE 119

{(3S,4R)-3-(4-Chloro-phenyl)-4-[(S)-1-(5-trifluoromethyl-pyridin-2-yloxy)-ethyl]-pyrrolidin-1-yl}-(6-methyl-pyridazin-4-yl)-methanone

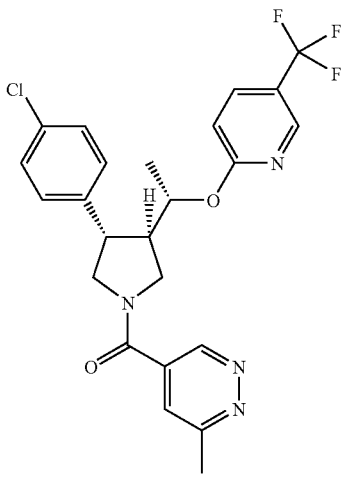

Coupling according to general procedure I:
Pyrrolidine intermediate: 2-{(S)-1-[(3R,4S)-4-(4-Chlorophenyl)-pyrrolidin-3-yl]-ethoxy}-5-trifluoromethyl-pyridine (XII-B-15)
Carboxylic acid: 6-Methyl-pyridazine-4-carboxylic acid (commercially available),
ES-MS m/e: 491.2(M+H+).

The invention claimed is:
1. A compound of formula I

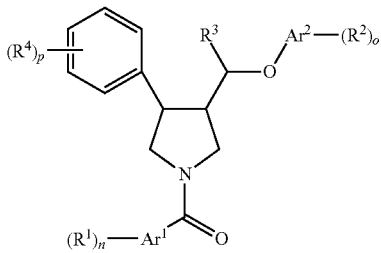

wherein
Ar$^1$ is pyridinyl;
Ar$^2$ is pyridinyl;
R$^1$ is hydrogen,
  halogen,
  lower alkyl,
  lower alkoxy,
  lower alkyl substituted by halogen,
  lower alkoxy substituted by halogen,
  S-lower alkyl,
  —S(O)$_2$-lower alkyl,
  —S(O)$_2$-di-lower alkyl amino,
  —(CH$_2$)$_q$R,
  cyano,
  amino,
  mono or di-lower alkyl amino,
  NHC(O)-lower alkyl, or
  cycloalkyl
wherein R is cyano, di-lower alkyl amino or pyrrolidin-1-yl;
R$^2$ is hydrogen, halogen, lower alkyl, lower alkyl substituted by halogen or cyano;
R$^3$ is hydrogen or lower alkyl or CH$_2$OH;
R$^4$ is hydrogen, halogen, lower alkyl, lower alkyl substituted by halogen or cyano;
n is 1, 2 or 3; in case n is 2 or 3, each R$^1$ is the same or different;
o is 1, 2 or 3; in case o is 2 or 3, each R$^2$ is the same or different;
p is 1, 2 or 3; in case p is 2 or 3, each R$^4$ is the same or different; and
q is 1 or 2;
or a pharmaceutically active salt thereof, diastereoisomer, enantiomer or racemic or non-racemic mixture thereof.
2. A compound of claim 1, wherein Ar$^1$ is pyridine-4-yl.
3. A compound of claim 2, selected from the group consisting of
[(3SR,4RS)-3-[(RS)-1-(5-chloro-pyridin-2-yloxy)-ethyl]-4-(3,4-dichloro-phenyl)-pyrrolidin -1-yl]-(2-methyl-pyridin-4-yl)-methanone and
(2-chloro-pyridin-4-yl)-{(3SR,4RS)-3-(3,4-dichloro-phenyl)-4-[(SR)-1-(5-trifluoromethyl -pyridin-2-yloxy)-ethyl]-pyrrolidin-1-yl}-methanone.
4. A compound of claim 1, wherein Ar$^1$ is pyridine-3-yl.
5. A compound of claim 4, selected from the group consisting of
[(3SR,4RS)-3-[(RS)-1-(5-chloro-pyridin-2-yloxy)-ethyl]-4-(3,4-dichloro-phenyl)-pyrrolidin -1-yl]-(6-methyl-pyridin-3-yl)-methanone,
[(3SR,4RS)-3-[(RS)-1-(5-chloro-pyridin-2-yloxy)-ethyl]-4-(3,4-dichloro-phenyl)-pyrrolidin -1-yl]-(6-dimethylamino-pyridin-3-yl)-methanone,
[(3S,4R)-3-[(R)-1-(5-chloro-pyridin-2-yloxy)-ethyl]-4-(3,4-dichloro-phenyl)-pyrrolidin-1-yl]-(6-methoxy-pyridin-3-yl)-methanone,
[(3R,4S)-3-[(S)-1-(5-chloro-pyridin-2-yloxy)-ethyl]-4-(3,4-dichloro-phenyl)-pyrrolidin-1-yl]-(6-methoxy-pyridin-3-yl)-methanone,
5-[(3SR,4RS)-3-[(RS)-1-(5-chloro-pyridin-2-yloxy)-ethyl]-4-(3,4-dichloro-phenyl) -pyrrolidine-1-carbonyl]-pyridine-2-carbonitrile,
[(3SR,4RS)-3-[(RS)-1-(5-chloro-pyridin-2-yloxy)-ethyl]-4-(3,4-dichloro-phenyl)-pyrrolidin -1-yl]-(6-dimethylaminomethyl-pyridin-3-yl)-methanone,
[(3SR,4RS)-3-[(RS)-1-(5-chloro-pyridin-2-yloxy)-ethyl]-4-(3,4-dichloro-phenyl)-pyrrolidin -1-yl]-(6-methylsulfanyl-pyridin-3-yl)-methanone, and
5-[(3S,4R)-3-[(R)-1-(5-chloro-pyridin-2-yloxy)-ethyl]-4-(3,4-dichloro-phenyl)-pyrrolidine-1 -carbonyl]-pyridine-2-carbonitrile.
6. A compound of claim 4, which is
5-[(3RS,4SR)-3-[(SR)-1-(5-cyano-pyridin-2-yloxy)-ethyl]-4-(3,4-dichloro-phenyl) -pyrrolidine-1-carbonyl]-pyridine-2-sulfonic acid dimethylamide.
7. The compound of formula I, wherein
Ar$^1$ is pyridinyl;
Ar$^2$ is pyridinyl;
R$^1$ is hydrogen, halogen, lower alkyl, lower alkoxy, cyano, amino, mono or di-lower alkyl amino, cycloalkyl or is lower alkyl substituted by halogen, cyano or amino;

$R^2$ is hydrogen, halogen, lower alkyl, cyano or is lower alkyl substituted by halogen or cyano;
$R^3$ is hydrogen or lower alkyl;
$R^4$ is hydrogen, lower alkyl or halogen;
n is 1, 2 or 3; in case n is 2 or 3, each $R^1$ is the same or different;
o is 1, 2 or 3; in case o is 2 or 3, each $R^2$ is the same or different; and
p is 1, 2 or 3; in case p is 2 or 3, each $R^4$ is the same or different;
or to a pharmaceutically active salt thereof.

8. A pharmaceutical composition comprising a therapeutically effective amount of a compound of formula I

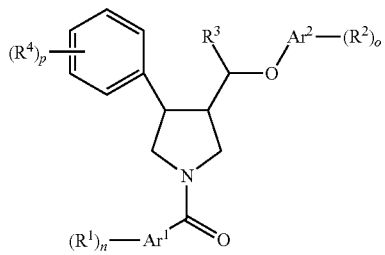

I wherein
Ar$^1$ is pyridinyl;
Ar$^2$ is pyridinyl;
$R^1$ is hydrogen,
halogen,
lower alkyl,
lower alkoxy,
lower alkyl substituted by halogen,
lower alkoxy substituted by halogen,
S-lower alkyl,
—S(O)$_2$-lower alkyl,
—S(O)$_2$-di-lower alkyl amino,
—(CH$_2$)$_q$R,
cyano,
amino,
mono or di-lower alkyl amino,
NHC(O)-lower alkyl, or
cycloalkyl
wherein R is cyano, di-lower alkyl amino or pyrrolidin-1-yl;
$R^2$ is hydrogen, halogen, lower alkyl, lower alkyl substituted by halogen or cyano;
$R^3$ is hydrogen or lower alkyl or CH$_2$OH;
$R^4$ is hydrogen, halogen, lower alkyl, lower alkyl substituted by halogen or cyano;
n is 1, 2 or 3; in case n is 2 or 3, each $R^1$ is the same or different;
o is 1, 2 or 3; in case o is 2 or 3, each $R^2$ is the same or different;
p is 1, 2 or 3; in case p is 2 or 3, each $R^4$ is the same or different; and
q is 1 or 2;
or a pharmaceutically active salt thereof, diastereoisomer enantiomer or racemic or non-racemic mixture thereof and a pharmaceutically acceptable carrier.

* * * * *

UNITED STATES PATENT AND TRADEMARK OFFICE
CERTIFICATE OF CORRECTION

PATENT NO. : 8,012,998 B2
APPLICATION NO. : 12/185157
DATED : September 6, 2011
INVENTOR(S) : Jablonski et al.

It is certified that error appears in the above-identified patent and that said Letters Patent is hereby corrected as shown below:

Title Page and col. 1, line 1 and 2;

• The Title reads: "PYRROLIDINE ARYL-ETHER AS NK-3 RECEPTOR ANTAGONISTS".
The Title should read -- PYRROLIDINE ARYL-ETHER AS NK3 RECEPTOR ANTAGONISTS --.

Title Page, item (73);

•The Assignee information reads: "Hoffmann—LA Roche Inc., Nutley, NJ (US)".
The Assignee information should read -- Hoffmann-La Roche Inc., Nutley, NJ (US) --.

Signed and Sealed this
Twenty-fifth Day of October, 2011

David J. Kappos
*Director of the United States Patent and Trademark Office*